US010702246B2

(12) United States Patent
Tsushima

(10) Patent No.: US 10,702,246 B2
(45) Date of Patent: Jul. 7, 2020

(54) ULTRASOUND DIAGNOSTIC APPARATUS AND AN ULTRASOUND SIGNAL PROCESSING METHOD

(71) Applicant: Konica Minolta, Inc., Chiyoda-ku, Tokyo (JP)

(72) Inventor: Mineo Tsushima, Kyoto (JP)

(73) Assignee: Konica Minolta, Inc., Tokyo (JP)

( * ) Notice: Subject to any disclaimer, the term of this patent is extended or adjusted under 35 U.S.C. 154(b) by 325 days.

(21) Appl. No.: 15/942,634

(22) Filed: Apr. 2, 2018

(65) Prior Publication Data

US 2018/0303461 A1    Oct. 25, 2018

(30) Foreign Application Priority Data

Apr. 24, 2017 (JP) ................. 2017-085699

(51) Int. Cl.
*A61B 8/00* (2006.01)
*A61B 8/08* (2006.01)
*G01S 7/52* (2006.01)
*G01S 15/89* (2006.01)

(52) U.S. Cl.
CPC ............. *A61B 8/5207* (2013.01); *A61B 8/54* (2013.01); *G01S 7/52047* (2013.01); *G01S 7/52087* (2013.01); *G01S 15/8997* (2013.01); *A61B 8/4477* (2013.01); *A61B 8/5284* (2013.01)

(58) Field of Classification Search
CPC ........... A61B 8/00; A61B 8/5207; A61B 8/54; A61B 8/4477
See application file for complete search history.

(56) References Cited

PUBLICATIONS

Nikolov et al., "Virtual ultrasound sources in high resolution ultrasound imaging," Proceedings of SPIE, vol. 4687, pp. 395-405 (2002).

*Primary Examiner* — Joseph M Santos Rodriguez
(74) *Attorney, Agent, or Firm* — BakerHostetler

(57) ABSTRACT

An ultrasound diagnostic apparatus that transmits an ultrasound beam using an ultrasound probe including transducers and generates acoustic line signal subframe data, includes: a transmitter that causes transmission transducer arrays to transmit the ultrasound beam; a receiver that generates a reception signal sequence; and a delay-and-sum part that performs delay-and-sum operation, wherein the receiver includes part receivers, the delay-and-sum part includes: part delay-and-sum parts that perform delay-and-sum to generate an acoustic line signal so as to generate acoustic line signal partial subframe data; part folding parts that extract an acoustic line signal sequence and arrange the acoustic line signals to generate acoustic line signal partial subframe folded data; a main summing part that sums the acoustic line signal partial subframe folded data to generate acoustic line signal subframe folded data; and a re-sequence part that re-sequences the acoustic line signals to generate the acoustic line signal subframe data.

10 Claims, 26 Drawing Sheets

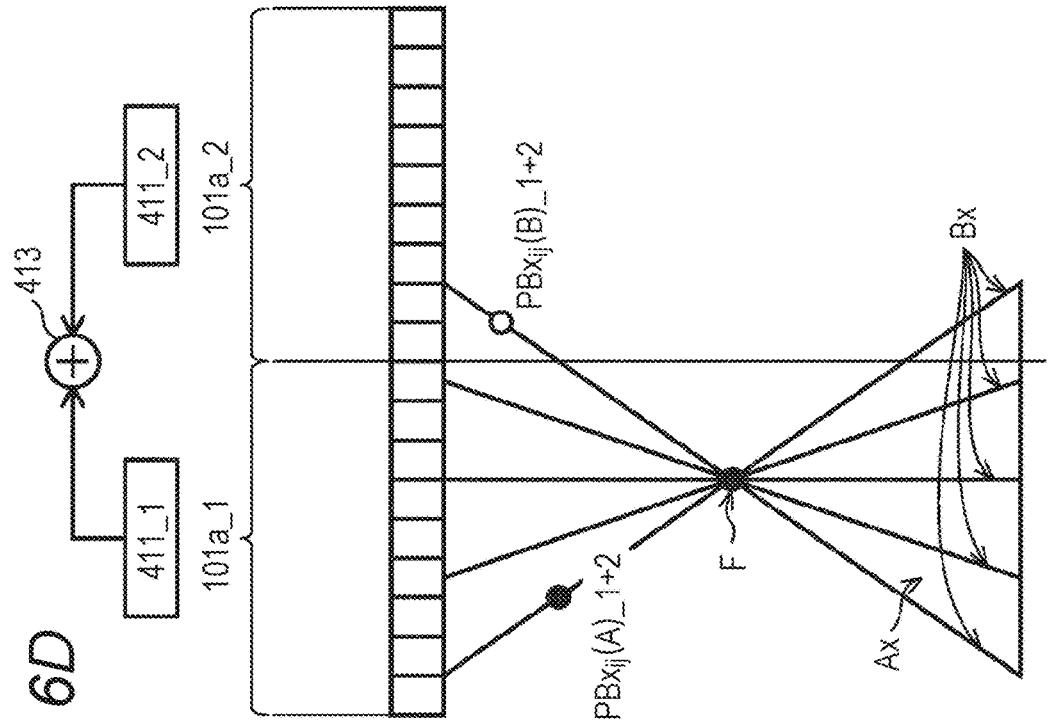
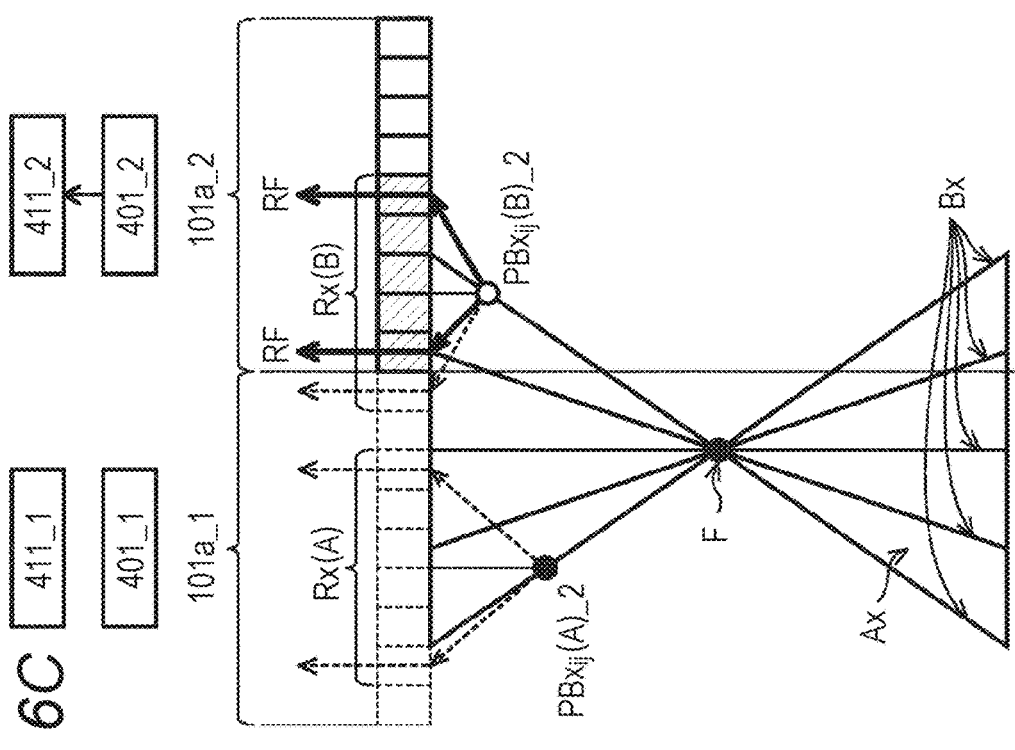

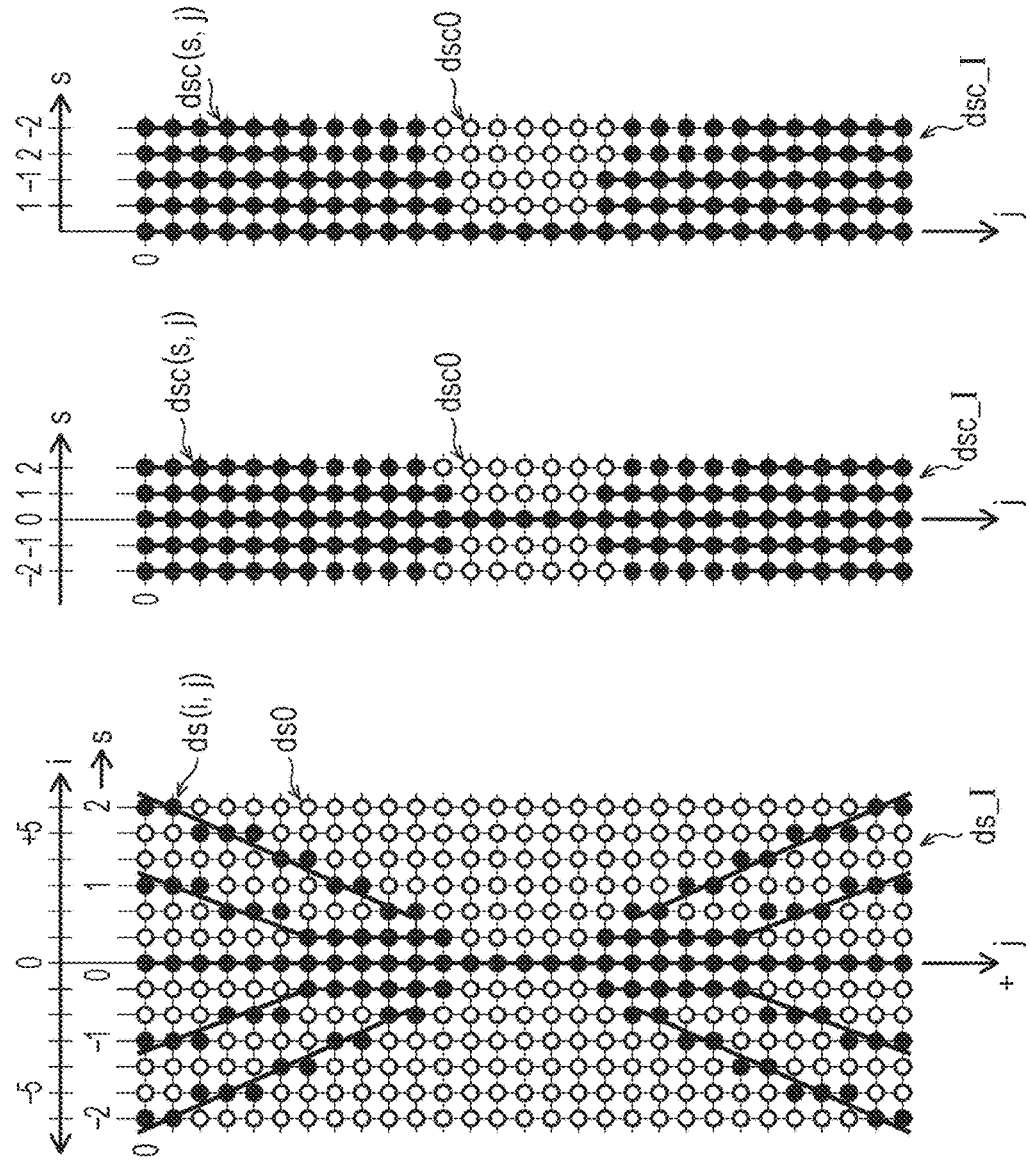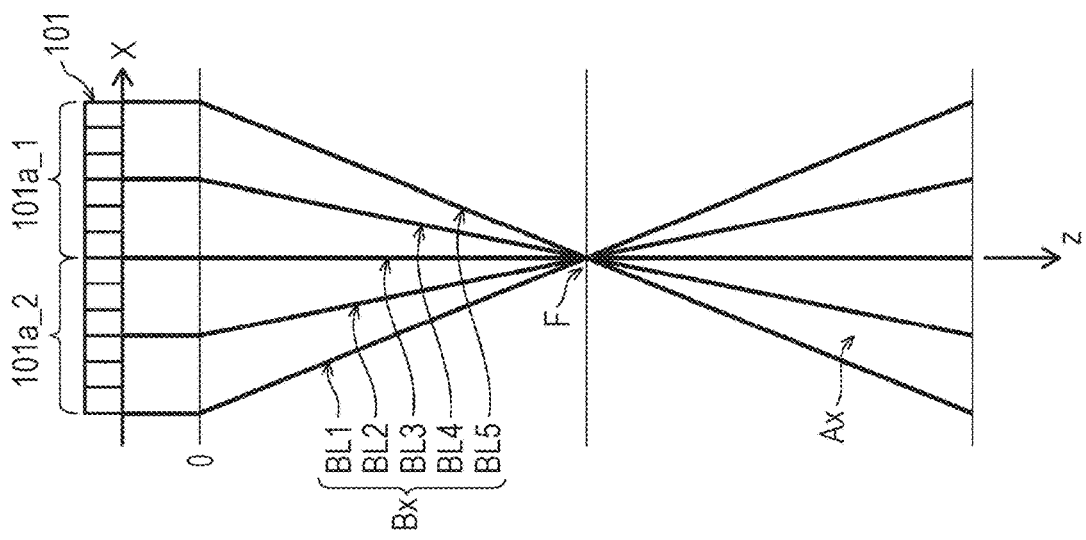

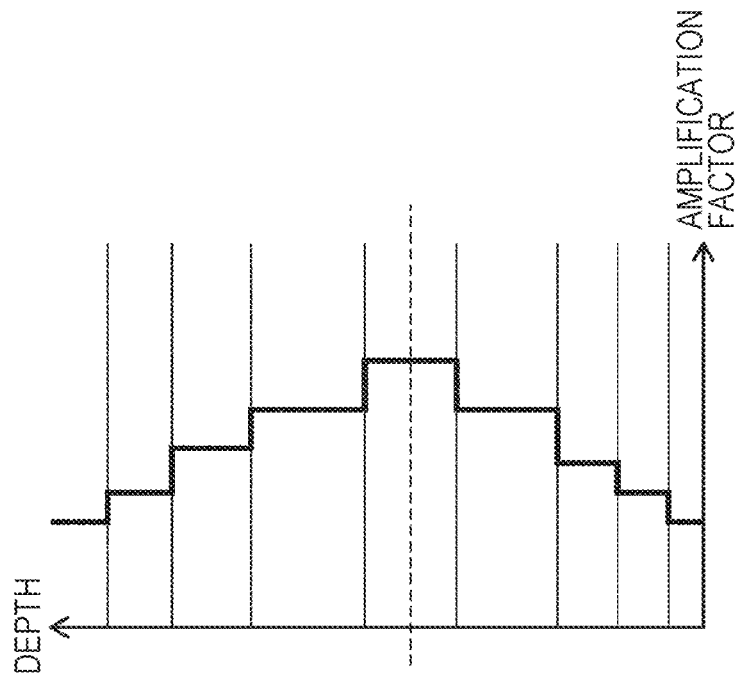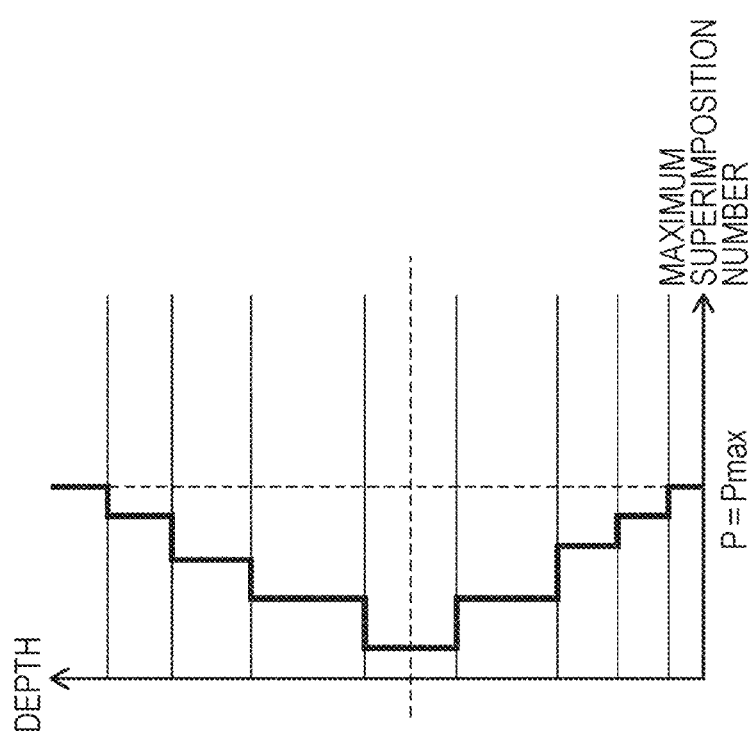

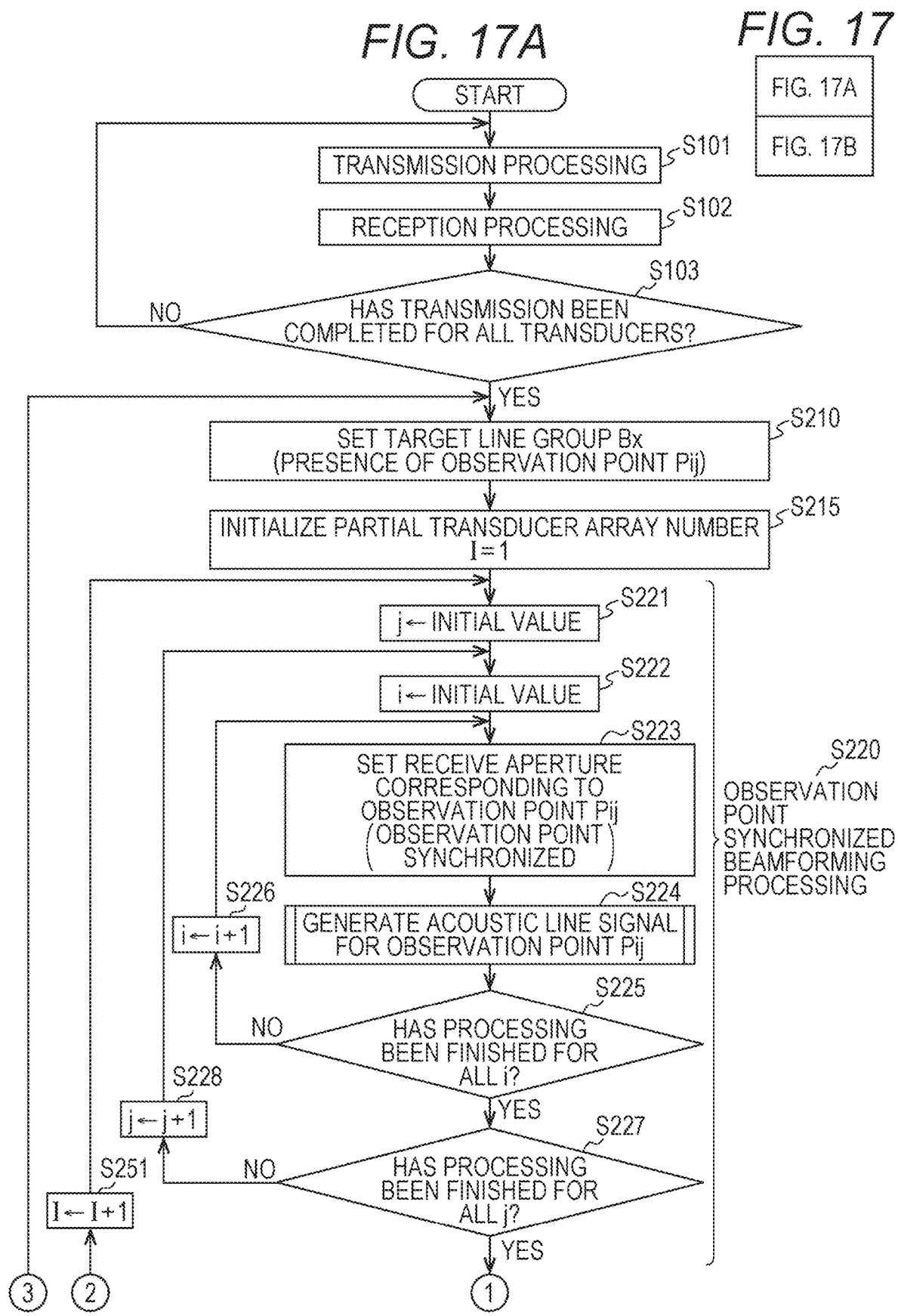

ULTRASOUND DIAGNOSTIC APPARATUS AND AN ULTRASOUND SIGNAL PROCESSING METHOD

The entire disclosure of Japanese patent Application No. 2017-085699, filed on Apr. 24, 2017, is incorporated herein by reference in its entirety.

BACKGROUND

Technological Field

The present disclosure relates to an ultrasound signal processing method and an ultrasound diagnostic apparatus using the ultrasound signal processing method, and particularly relates to a receive beamforming processing method in an ultrasound signal processing method.

Description of the Related Art

The ultrasound diagnostic apparatus transmits ultrasound waves to the inside of a subject from the ultrasound probe, receives a reflected wave of the ultrasound wave generated from a difference in acoustic impedance in the tissue of the subject, generates an ultrasound tomographic image illustrating the shape of an internal tissue of the subject on the basis of an obtained electric signal and displays the image.

A conventional ultrasound diagnostic apparatus uses a method referred to as a delay-and-sum (delay-and-sum) method as a receive beamforming method based on a received reflected wave (for example, Masayasu Ito, Tsuyoshi Mochizuki, "Ultrasound diagnostic apparatus" published by Corona Publishing Co., Ltd., Aug. 26, 2002 (P42-P45)). This method transmits ultrasound beams from a plurality of transducers so as to focus at a certain depth of the subject to generate an acoustic line signal on a central axis of the ultrasound beam. This leads to a problem of low utilization efficiency of ultrasound waves applied on portions other than the central axis and low spatial resolution and signal S/N ratio of the acoustic line signal obtained outside the vicinity of the transmission focal point.

To overcome this, there is a proposed method of a receive beamforming method using a synthetic aperture method to obtain a high quality image with high spatial resolution even in a region other than the vicinity of the transmission focal point (refer to "Virtual ultrasound sources in high resolution ultrasound imaging", S. I. Nikolov and J. A. Jensen, in Proc, SPIE—Progress in biomedical optics and imaging, vol. 3, 2002, P. 395-405, for example). The synthetic aperture method can be applied to perform delay control taking account of both a propagation path of an ultrasound transmission wave and an arrival time of the reflected wave to the transducer by the propagation path, making it possible to generate an acoustic line signal for an entire ultrasound main irradiation region including portions other than the vicinity of the transmission focal point with one ultrasound transmission. Furthermore, the synthetic aperture method is capable of enhancing spatial resolution and the S/N ratio by superimposing a plurality of acoustic line signals for a same observation point obtained from a plurality of times of ultrasound transmissions.

In the synthetic aperture method, however, an increase in the area of the target region where the acoustic line signal is generated by one ultrasound transmission also increases the number of observation points in the region, leading to an increase in the computation amount in the delay-and-sum, in the memory capacity needed for storing the data of the acoustic line signal after the delay-and-sum, and in the data transmission capability needed for transferring the data of the acoustic line signal. This generates a need to provide hardware with high computation processing capability, larger memory capacity for storing the acoustic line signal, and enhanced data transmission capability for transfer in order to perform the arithmetic processing of the delay-and-sum at high speed, leading to a problem of an increase in the cost of the ultrasound diagnostic apparatus.

SUMMARY

The present disclosure has been made in view of the above-described problem, and an object thereof is to provide an ultrasound signal processing method and an ultrasound diagnostic apparatus using the ultrasound signal processing method capable of reducing the computation amount of the delay-and-sum and the data amount of the acoustic line signal to be generated while suppressing the degradation of the spatial resolution and the S/N ratio, capable of downscaling the necessary internal memory capacity and data transmission capability in a receive beamformer of the ultrasound diagnostic apparatus.

To achieve the abovementioned object, according to an aspect of the present invention, an ultrasound diagnostic apparatus that transmits an ultrasound beam to a subject using an ultrasound probe including a plurality of transducers and generates acoustic line signal subframe data on the basis of a reflected wave obtained from the subject, reflecting one aspect of the present invention comprises: a transmitter that sets a focal point defining a converging point of an ultrasound beam in the subject and causes a plurality of transmission transducer arrays selected from the plurality of transducers to transmit the ultrasound beam to converge at the converging point; a receiver that generates a reception signal sequence for each of the transducers of the ultrasound probe on the basis of the reflected wave received by the ultrasound probe from the subject; and a delay-and-sum part that performs delay-and-sum operation on the reception signal sequence based on the reflected wave obtained within an ultrasound beam main irradiation region to generate acoustic line signal subframe data for a plurality of on-line observation points present in a target line group passing through the focal point among a plurality of intra-region observation points corresponding to the position within the ultrasound beam main irradiation region, wherein the receiver includes a plurality of part receivers that generates the reception signal sequence on the basis of the reflected wave received by each of the transducers included in a partial transducer array from the subject for each of a plurality of the partial transducer arrays obtained by dividing the transmission transducer array, the delay-and-sum part includes: a plurality of part delay-and-sum parts that performs delay-and-sum on the reception signal sequence corresponding to the plurality of partial transducer arrays to generate an acoustic line signal for the plurality of on-line observation points so as to generate acoustic line signal partial subframe data corresponding to each of the plurality of partial transducer arrays; a plurality of part folding parts that extracts an acoustic line signal sequence corresponding to the plurality of on-line observation points from the acoustic line signal partial subframe data corresponding to each of the plurality of partial transducer arrays, and that arranges the acoustic line signals with reduced intervals between the target lines included in the target line group to generate acoustic line signal partial subframe folded data; a main summing part that sums the acoustic line signal partial subframe folded data corresponding to each of the plurality of partial transducer arrays on the basis of the positions of the arranged observation points to generate acoustic line signal subframe folded data; and a re-sequence part that re-sequences the acoustic line signals in the acoustic line signal subframe folded data to the positions of the on-line observation points in the main irradiation region to generate the acoustic line signal subframe data.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIGS. 6A to 6C are schematic diagrams illustrating an outline of division processing on a part receiver, a part receiver of the delay-and-sum part, and a part delay-and-sum part when a division number n of a partial transducer array is two; FIG. 6D is a schematic diagram illustrating an outline of generation of acoustic line signal subframe data ds_sf;

FIGS. 12A to 12D are explanatory diagrams illustrating operation of the part folding part;

FIGS. 16A and 16B are schematic diagrams respectively illustrating the maximum number of superimpositions in the combined acoustic line signals and an outline of amplification processing in an amplification processing unit;

FIGS. 17A and 17B are flowcharts illustrating beamforming processing operation according to the embodiment;

DETAILED DESCRIPTION OF EMBODIMENTS

Figure 1:
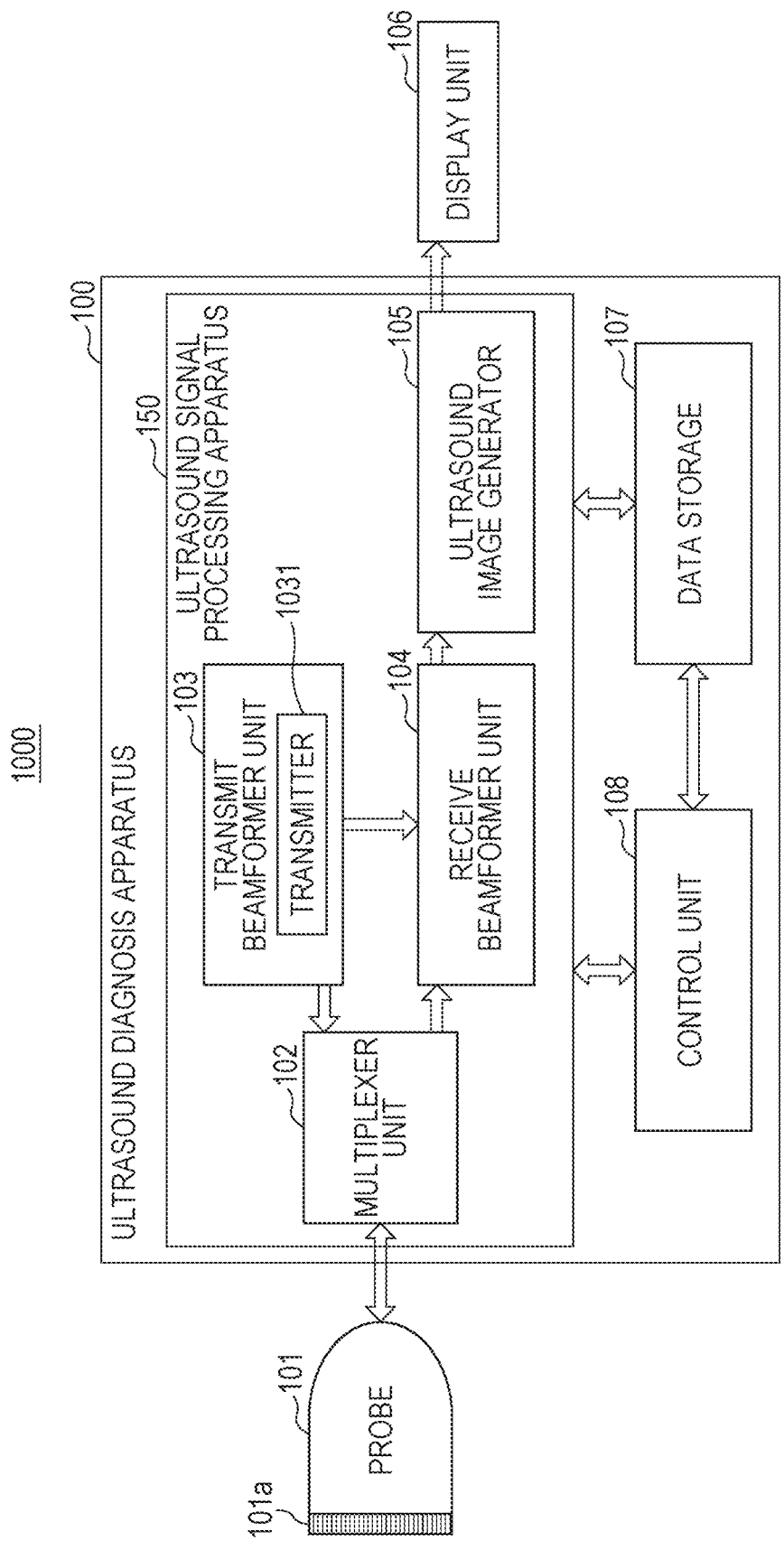
FIG. 1 is a functional block diagram illustrating a configuration of an ultrasound diagnostic apparatus according to an embodiment.

Hereinafter, one or more embodiments of the present invention will be described with reference to the drawings. However, the scope of the invention is not limited to the disclosed embodiments.

Background of Detailed Description of Embodiments

The inventors examines various techniques to reduce the computation amount while suppressing degradation of the spatial resolution and the S/N ratio of the acoustic line signal on an ultrasound diagnostic apparatus using the synthetic aperture method.

In typical converging transmit beamforming, a wavefront is converged to allow an ultrasound beam to be focused at a certain depth of the subject. Therefore, the ultrasound wave is mainly applied to the ultrasound main irradiation region from a plurality of transducers used for ultrasound transmission by one transmission of ultrasound wave. When the number of the transmission focal points is one, the ultrasound main irradiation region is an hourglass-shaped region surrounded by two straight lines passing through the transmission focal point from each of the both ends of a base with the transmission transducer array as the base, with the wavefront being an arc shape centered on the transmission focal point. That is, the ultrasound main irradiation region is converged at or in the vicinity of the focal point at a certain depth of the focal point, while the shape at other depths is such that the longer the distance to the focal depth, the greater the width in a array direction.

In the synthetic aperture method, observation points can be set for the entire region of the ultrasound main irradiation region in one transmission event, and therefore it is preferable to set the entire region of the ultrasound main irradiation region as the target region.

The number of observation points included in the target region, however, is proportional to the area of the target region, and thus, the computation amount of the delay-and-sum, the memory capacity needed for storing the acoustic line signal after the delay-and-sum, and the data transmission capability needed for transferring the acoustic line signal are inevitably proportional to the area of the target region. Accordingly, an increase in the area of the target region directly leads to an increase in the memory capacity needed by the ultrasound diagnostic apparatus. In order to suppress degradation of temporal resolution and the usability, there is a need to provide a processor with high processing capability, such as a high performance GPU, capable of performing delay-and-sum computation at high speed, leading to an increase in the cost of the ultrasound diagnostic apparatus.

In order to reduce the computation amount, it is conceivable to reduce the number of observation points included in the target region. The inventors gained a concept of setting a target line group formed with a plurality of target lines passing through a focal point or its vicinity as a target region to reduce the number of observation points. With this, it is possible to achieve a configuration in which the number and the density of the observation points in the depth direction is maintained and the density of the observation points is decreased in a direction perpendicular to the target line so as to suppress reduction of the distance resolution. Together with this, by reducing the number of observation points to be computed, it is possible to reduce the computation amount of the delay-and-sum.

Furthermore, it is conceivable to reduce the hardware cost through distributed processing of the delay-and-sum processing. In that case, there is a need to reduce the computation amount per arithmetic unit by distributing the delay-and-sum processing to a plurality of arithmetic units. For example, there is a conceivable method of dividing a plurality of transducer arrays arranged in an ultrasound probe into a plurality of partial transducer arrays, performing preceding-stage delay-and-sum processing on the basis of a reception signal obtained for each of the partial transducer arrays, and combining acoustic line signals generated from each of the delay-and-sum processing at a succeeding stage. This configuration makes it possible to achieve a hardware configuration by using, for example, a plurality of small-scale field programmable gate arrays (FPGAs) in each of the preceding-stage delay-and-sum processing and the succeeding-stage combining processing corresponding to each of the partial transducer arrays, leading to drastic reduction of the cost of the arithmetic unit in the hardware. That is, it is possible to avoid cost increase caused by a large computation scale in a case of implementing functions by intensive processing using a single FPGA or the like. In other words, hardware such as an FPGA enabling large-scale computation is very expensive, and thus cost can be reduced by dividing the same computation amount into a plurality of integrated circuits to be processed.

In a case, however, where processing is divided and implemented by a plurality of integrated circuits, there is a need to perform data transfer between the integrated circuits. Because of large amount of data transfer, it would be difficult to implement data transfer operation with inexpensive hardware even though the total computation amount can be covered. More specifically, the memory capacity needed for temporarily storing the acoustic line signal obtained by the preceding-stage delay-and-sum and the data transmission capability necessary for transferring the acoustic line signal from the preceding-stage processing to the succeeding-stage processing would be rate-determining in cost reduction. In order to reduce these, it is insufficient to reduce the number of observation points to be computed, and there is a need to downscale the geometric data amount of the acoustic line signal after the delay-and-sum.

Therefore, the inventors have made an earnest study on a method capable of downscaling the geometric data amount of the acoustic line signal without accompanying a special computation load, so as to achieve the following embodiments.

Hereinafter, an ultrasound image processing method according to the embodiments and an ultrasound diagnostic apparatus using the same will be described in detail with reference to the drawings.

EMBODIMENTS

1. Overall Configuration

Hereinafter, an ultrasound diagnostic apparatus 100 according to an embodiment will be described with reference to the drawings.

FIG. 1 is a functional block diagram illustrating a configuration of the ultrasound diagnostic apparatus 100 according to the embodiment. As illustrated in FIG. 1, the ultrasound diagnostic system 1000 includes: an ultrasound probe 101 (hereinafter referred to as "probe 101") having a plurality of transducers 101a that transmits ultrasound waves toward a subject and receives the reflected waves; an ultrasound diagnostic apparatus 100 that causes the probe 101 to transmit and receive ultrasound waves and generates an ultrasound image on the basis of an output signal from the probe 101; and a display unit 106 that displays the ultrasound image on a screen. The probe 101 and the display unit 106 are each configured to be connectable to the ultrasound diagnostic apparatus 100. FIG. 1 illustrates a state in which the probe 101 and the display unit 106 are connected to the ultrasound diagnostic apparatus 100. Note that the probe 101 and the display unit 106 may be provided inside the ultrasound diagnostic apparatus 100.

2. Configuration of Ultrasound Diagnostic Apparatus 100

The ultrasound diagnostic apparatus 100 includes: a multiplexer unit 102 that selects transducers to be used for transmission or reception among the plurality of transducers 101a of the probe 101 and ensures input and output to the selected transducers; a transmit beamformer unit 103 that controls a timing of application of a high voltage to each of the transducers 101a of the probe 101 in order to perform transmission of ultrasound waves transmitted from the probe 101; and a receive beamformer unit 104 that performs, on the basis of the reflected wave of the ultrasound waves received by the probe 101, amplification of an electrical signal obtained by the plurality of transducers 101a, A/D conversion, and generation of an acoustic line signal by applying receive beamforming on the signal. The ultrasound diagnostic apparatus 100 further includes: an ultrasound image generator 105 that generates an ultrasound image (B-mode image) on the basis of an output signal from the receive beamformer unit 104; a data storage 107 that stores the acoustic line signal output from the receive beamformer unit 104 and the ultrasound image output by the ultrasound image generator 105; and a control unit 108 that controls each of the constituents.

Among these components, the multiplexer unit 102, the transmit beamformer unit 103, the receive beamformer unit 104, and the ultrasound image generator 105 constitute an ultrasound signal processing apparatus 150.

Each of the elements constituting the ultrasound diagnostic apparatus 100, for example, the multiplexer unit 102, the transmit beamformer unit 103, the receive beamformer unit 104, the ultrasound image generator 105, and the control unit 108 are implemented by a hardware circuit such as a field programmable gate array (FPGA) and an application specific integrated circuit (ASIC). Alternatively, it may be implemented by software and a programmable device such as a processor. An example of an applicable processor is a central processing unit (CPU) or a GPU (graphic processing unit), and a configuration using the GPU is referred to as a general-purpose computing on graphics processing unit (GPGPU). These constituents can be formed with a single circuit component or an aggregate of a plurality of circuit components. In addition, a plurality of constituents can be combined into a single circuit component, or a plurality of circuit components as an aggregate.

The data storage 107 is a computer readable recording medium, and implemented by a flexible disk, a hard disk, an MO, a DVD, a DVD-RAM, a BD, a semiconductor memory, or the like. Moreover, the data storage 107 may be a storage apparatus externally connected to the ultrasound diagnostic apparatus 100.

3. Configuration of Main Parts of Ultrasound Diagnostic Apparatus 100

The ultrasound diagnostic apparatus 100 according to a first embodiment includes the transmit beamformer unit 103 that causes the transducers 101a of the probe 101 to transmit ultrasound waves and the receive beamformer unit 104 that computes an electric signal obtained by reception of the ultrasound reflected waves by the probe 101 and generates an acoustic line signal to generate an ultrasound image. Accordingly, the present specification will mainly describe configurations and functions of the transmit beamformer unit 103 and the receive beamformer unit 104. Note that configurations other than the transmit beamformer unit 103 and the receive beamformer unit 104 can be the same as those used in known ultrasound diagnostic apparatuses, and the beamformer units according to the present embodiment are applicable to the beamformer units of known ultrasound diagnostic apparatus.

Hereinafter, configurations of the transmit beamformer unit 103 and the receive beamformer unit 104 will be described.

3.1 Transmit Beamformer Unit 103

The transmit beamformer unit 103 is connected to the probe 101 via the multiplexer unit 102 and controls high-voltage application timing for each of a plurality of transducers included in a transmission transducer array (transmit aperture Tx) corresponding to all or a part of a plurality of transducers 101a selected from the plurality of transducers 101a present on the probe 101 so as to perform ultrasound transmission from the probe 101. The transmit beamformer unit 103 is formed with a transmitter 1031.

Based on a transmission control signal from the control unit 108, the transmitter 1031 performs transmission processing of supplying a pulse-like transmission signal to each of the transducers included in the transmit aperture Tx among the plurality of transducers 101a present in the probe 101, to cause the transducer to transmit the ultrasound beam. Specifically, the transmitter 1031 includes, for example, a clock generation circuit, a pulse generation circuit, and a delay circuit. The clock generation circuit is a circuit that generates a clock signal to determine the transmission timing of the ultrasound beam. The pulse generation circuit is a circuit for generating a pulse signal for driving each of the transducers. The delay circuit is a circuit for setting a delay time of the ultrasound beam transmission timing for each of the transducers and delaying the transmission of the ultrasound beam by the delay time to perform the focusing of the ultrasound beam.

The transmitter 1031 repeatedly transmits ultrasound waves while sequentially moving the transmit aperture Tx in an array direction each of ultrasound transmissions, and performs ultrasound transmission from all the transducers 101a present in the probe 101. That is, in the present embodiment, the transmit aperture Tx moves by one transducer for each of the ultrasound transmissions. Information indicating the position of the transducer included in the transmit aperture Tx is output to the data storage 107 via the control unit 108. For example, when the total number of transducers 101a present in the probe 101 is 192, for example, number 20 to 100 may be selected as the number of transducer arrays constituting the transmit aperture Tx, so as to move the transducer by one for each of the ultrasound transmissions. Hereinafter, the ultrasound transmission performed by the transmitter 1031 from the same transmit aperture Tx will be referred to as a "transmission event".

Figure 2:
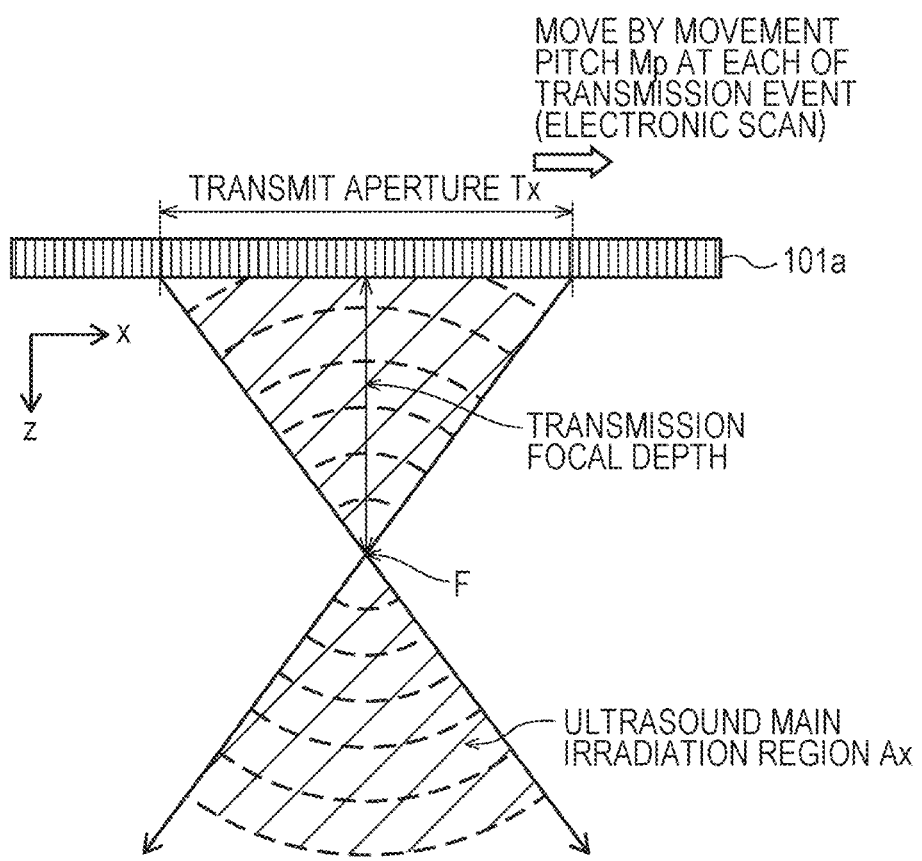
FIG. 2 is a schematic diagram illustrating a propagation path of an ultrasound transmission wave by a transmit beamformer unit.

FIG. 2 is a schematic diagram illustrating a propagation path of the ultrasound transmission wave by the transmit beamformer unit 103. An array (transmission transducer array) of transducers 101a arranged in an array that contributes to ultrasound transmission in a certain transmission event is illustrated as the transmit aperture Tx. In addition, an array length of the transmit aperture Tx is referred to as a transmit aperture length.

The transmit beamformer unit 103 controls the transmission timing of each of the transducers such that the more toward the center of the transmit aperture Tx the transducer is located, the more delayed the transmission timing for the transducer. With this control, the ultrasound transmission wave transmitted from the transducer array in the transmit aperture Tx is focused at a certain point of the wavefront at a certain depth (focal depth) of the subject, that is, focused (converged) at a transmission focal point F.

The ultrasound beam is not necessarily focused at one point and might be converged on a region having focusing corresponding to 1.5 times to several times of one transducer. In this case, the ultrasound main irradiation region has a decreased width in the array direction down to the focal depth, has the width of the focus region in the array direction at the focal depth, and has an expanded shape in the array direction again in a region deeper than the focal depth. In this case, for the sake of convenience, a center point of the focus region at the focal depth is defined as the "focal point"

The depth of the transmission focal point F (hereinafter referred to as "focal depth") can be set to any depth. The wavefront focused at the transmission focal point F diffuses again to allow the ultrasound transmission wave to propagate in an hourglass-shaped space delimited by two intersecting straight lines with the transmit aperture Tx as the base and the transmission focal point F as a node. That is, the ultrasound wave emitted at the transmit aperture Tx gradually reduces its width on the space (horizontal axis direction in the figure), minimizes the width of the wave at the transmission focal point F, and the wave diffuses and propagates while increasing its width again at a deeper (lower in the figure) point of progress of the wave. This hourglass-shaped region is the ultrasound main irradiation region Ax.

Note that the "ultrasound main irradiation region" Ax represents a region where the phases of the ultrasound waves transmitted from the individual transducers constituting the transmission transducer array are aligned at all points within the region. As described above, the ultrasound main irradiation region Ax may transmit the ultrasound transmission wave so as to converge in the vicinity of the transmission focal point F being a single point.

3.2 Configuration of Receive Beamformer Unit 104

Figure 3:
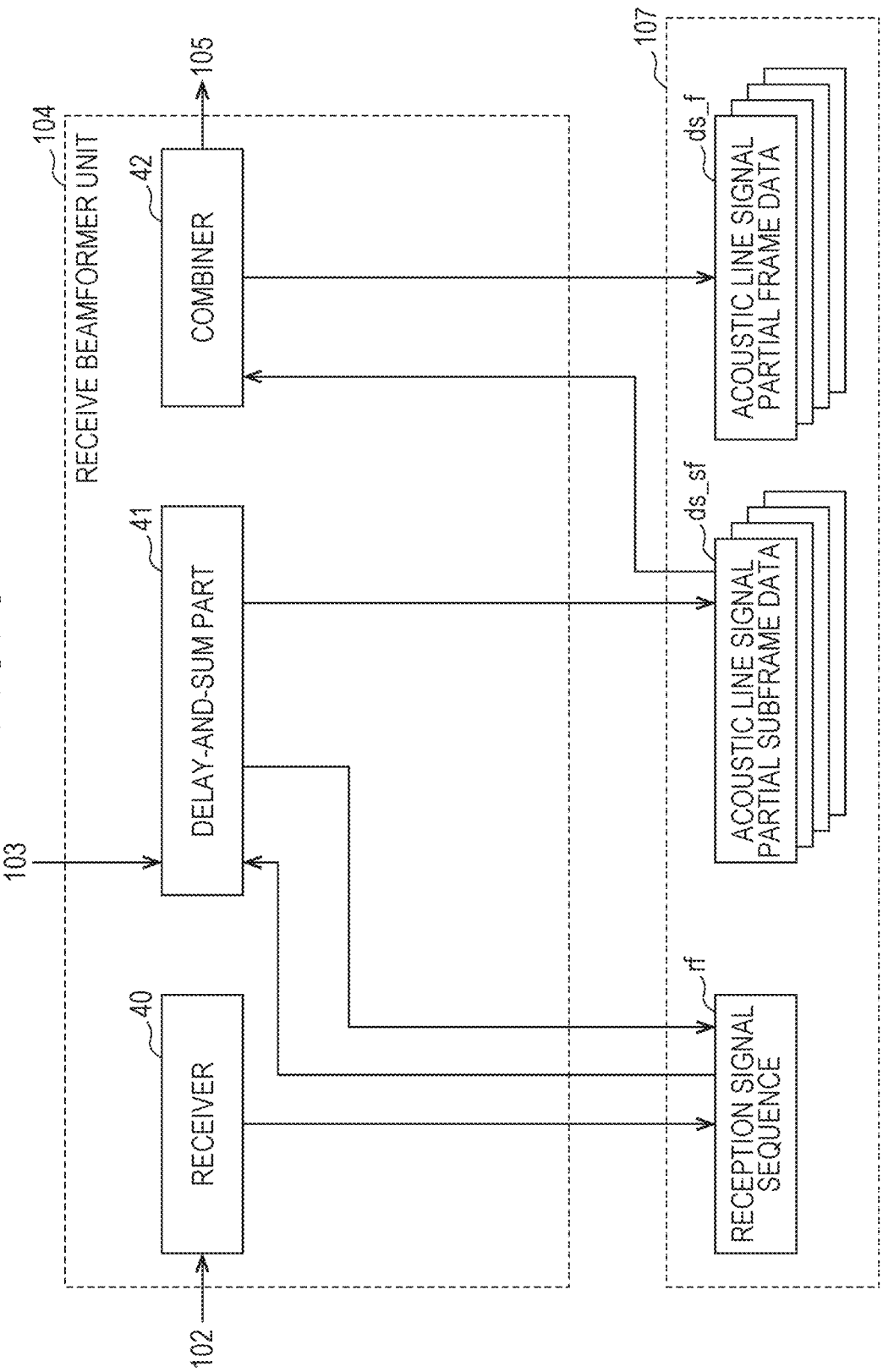
FIG. 3 is a functional block diagram illustrating a configuration of a receive beamformer unit.
Figure 4:
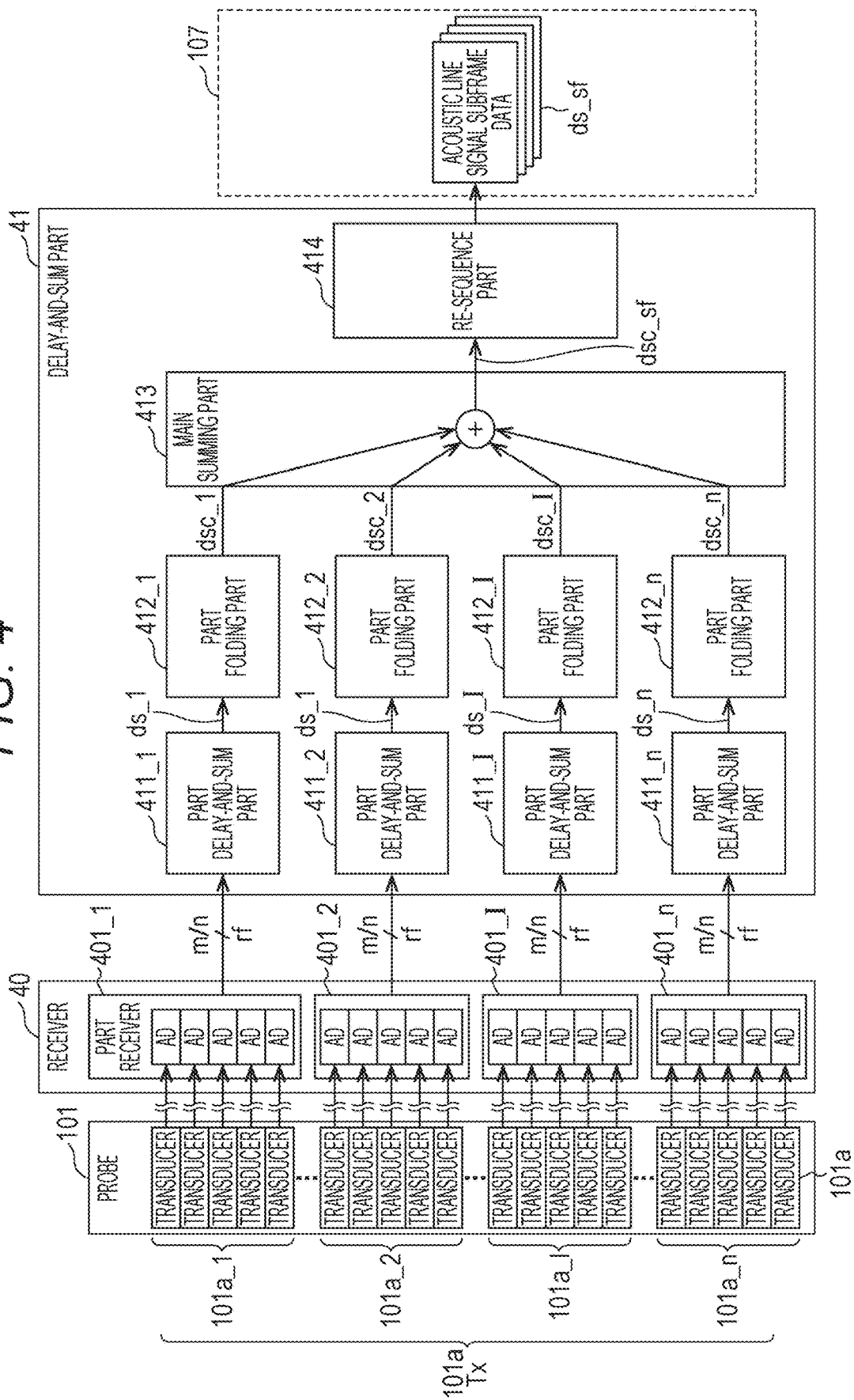
FIG. 4 is a functional block diagram illustrating a configuration of a receiver and a delay-and-sum part.

On the basis of the reflected wave of the ultrasound wave received by the probe 101, the receive beamformer unit 104 generates an acoustic line signal from an electric signal obtained by the plurality of transducers 101a. The "acoustic line signal" is a signal after delay-and-sum processing has been applied on a certain observation point. The delay-and-sum processing will be described below. FIG. 3 is a functional block diagram illustrating a configuration of the receive beamformer unit 104. FIG. 4 is a functional block diagram illustrating configurations of the receiver 40 and the delay-and-sum part 41. As illustrated in FIG. 3, the receive beamformer unit 104 includes a receiver 40, the delay-and-sum part 41, and a combiner 42.

Hereinafter, an outline of the configuration of individual portions constituting the receive beamformer unit 104 will be described.

3.2.1 Receiver 40

The receiver 40 is a circuit connected to the probe 101 via the multiplexer unit 102, so as to amplify the electric signal obtained from reception of the ultrasound reflected wave by the probe 101 in synchronization with the transmission event and thereafter generate an A/D converted reception signal (RF signal). The receiver 40 generates a reception signal in chronological order of the transmission event, outputs the generated signal to the data storage 107, and stores the reception signal in the data storage 107.

Note that the reception signal (RF signal) is a digital signal obtained by A/D converting an electric signal converted from the reflected ultrasound wave received by each of the transducers, and is formed as a sequence of signals received by each of the transducers arranged in a transmission direction of the ultrasound waves (direction of depth of the subject).

In the transmission event, as described above, the transmitter 1031 causes each of the plurality of transducers included in the transmit aperture Tx among the plurality of transducers 101a present in the probe 101 to transmit the ultrasound beams. In contrast, the receiver 40 generates a sequence of the reception signals for each of the transducers on the basis of the reflected ultrasound waves obtained by each of the transducers corresponding to some or all of the plurality of transducers 101a present in the probe 101 in synchronization with the transmission event. Here, the transducer that receives the reflected ultrasound wave is referred to as a "receiving transducer". It is preferable that the number of receiving transducers is larger than the number of transducers included in the transmit aperture Tx. In addition, the number of receiving transducers may be the total number of transducers 101a present in the probe 101.

As illustrated in FIG. 4, the receiver 40 is divided into a plurality (n) of part receivers 401_1 that generates reception signal sequences on the basis of the reflected wave received from the subject by each of the transducers included in a plurality of partial transducer arrays 101a_1 (1=1 to n). The plurality of partial transducer arrays 101a_1 is obtained by dividing m transmission transducer array 101aTx (m is a natural number larger than 1) selected from the plurality of transducers 101a present in the probe 101 into n (n is a natural number of m or below and larger than 1). Each of the partial transducer arrays 101a_1 includes m/n transducers. For example, the number m of the transmission transducer arrays 101aTx may be set to 128, the number n may be 2, and the number of transducers included in the partial transducer array 101a_1 may be 64. In the present specification, the part receiver 401_1 is referred to as a "part receiver 401" unless the order 1 needs to be distinguished.

The transmitter 1031 repeatedly transmits ultrasound waves while sequentially moving the transmit aperture Tx in an array direction in synchronization with transmission events, and performs ultrasound transmission from all of the plurality of transducers 101a present in the probe 101. The receiver 40 generates a reception signal sequence for each of the receiving transducers in synchronization with the transmission event, and the generated reception signal is stored in the data storage 107.

3.2.2 Delay-and-Sum Part 41

The delay-and-sum part 41 is a circuit that performs delay-and-sum operation on the reception signal sequence based on the reflected wave obtained within an ultrasound main irradiation region Ax to generate acoustic line signal subframe data dssf for a plurality of on-line observation points PBxij present in a target line group Bx passing through the focal point F among a plurality of intra-region observation points Pij corresponding to the positions within the main irradiation region Ax of the ultrasound beam. The details of the "target line group" will be described below.

As illustrated in FIG. 4, the delay-and-sum part 41 includes a plurality (n) of part delay-and-sum parts 411_1 (1=1 to n), a plurality (n) of part folding parts 412_1, a main summing part 413, and a re-sequence part 414.

3.2.2.1 Part Delay-and-Sum Part 411

(1) Outline

As illustrated in FIG. 4, the part delay-and-sum part 411 applies delay-and-sum on the reception signal sequences corresponding to the plurality of partial transducer arrays 101a_1 input from the plurality (n) of part receivers 401_1, respectively, to generate an acoustic line signal for the plurality of on-line observation points PBxij. Each of the plurality (n) of part delay-and-sum parts 411_1 generates acoustic line signal partial subframe data ds_1 for all the observation points PBxij on the target line group Bx among the plurality of intra-region observation points Pij, corresponding to each of the plurality of partial transducer arrays 101a_1. In the present specification, the part delay-and-sum part 411_1 will be referred to as a "part delay-and-sum part 411" unless the order 1 needs to be distinguished.

Figure 5A:
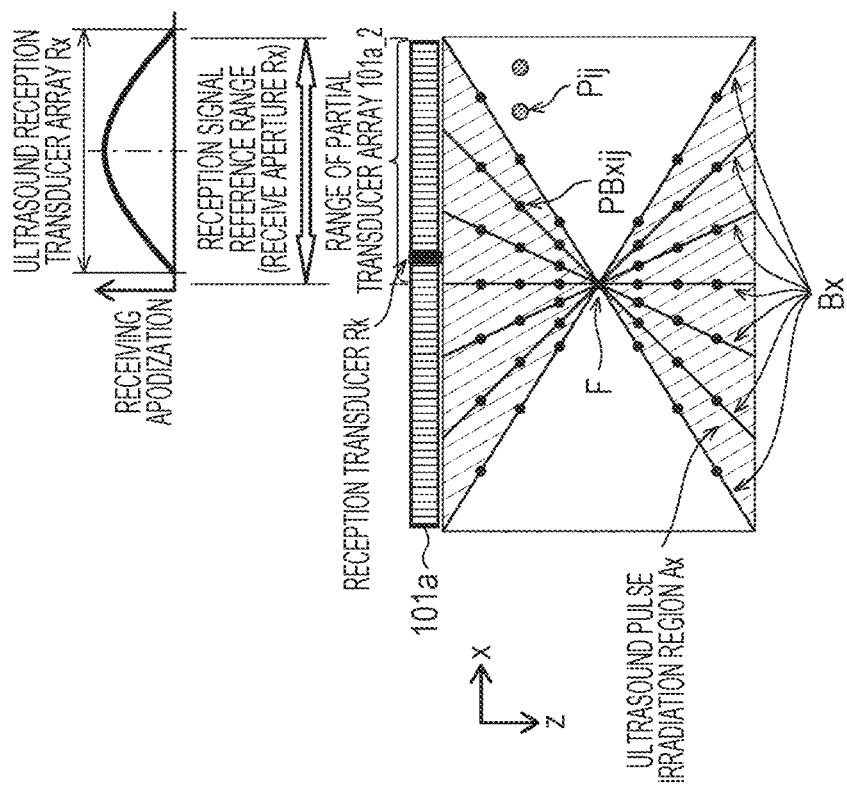
FIGS. 5A and 5B are schematic diagrams illustrating an outline of a method of generating an acoustic line signal in the receive beamformer unit.
Figure 5B:
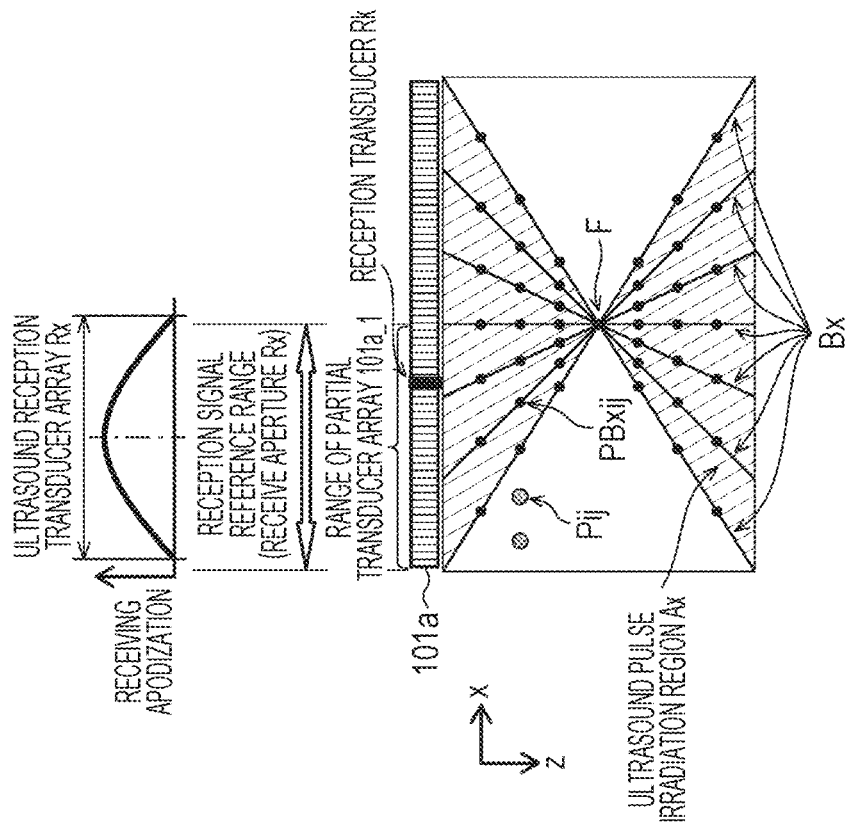

FIGS. 5A and 5B are schematic diagrams illustrating an outline of a method of generating an acoustic line signal in the receive beamformer unit 104. For the sake of simplicity, the figure illustrates an exemplary case where the transducer array (101a) is divided into two partial transducer arrays 101a_1 and 101a 2, and the delay-and-sum part 41 is formed with two part delay-and-sum parts 411_1 and 411_2.

As illustrated in FIGS. 5A and 5B, the part delay-and-sum part 411_1 performs phase-and-sum processing on the plurality of on-line observation points PBxij present on the target line group Bx passing through the focal point F among the plurality of intra-region observation points Pij present in the ultrasound main irradiation region Ax, as delay-and-sum processing on the partial transducer array 101a_1. At this time, a reception signal reference range as a target of the delay-and-sum processing by the part delay-and-sum part 411_1 is a reception signal sequence rf based on the reflected wave received from the subject by the array (receive aperture Rx) of the reception transducer Rk (k is a natural number larger than 1) included in the partial transducer array 101a_1.

The division processing in the part delay-and-sum part 411 will be described more specifically.

i) Generating Reception Signal Sequence Rf in Receiver 40

Figure 6A:
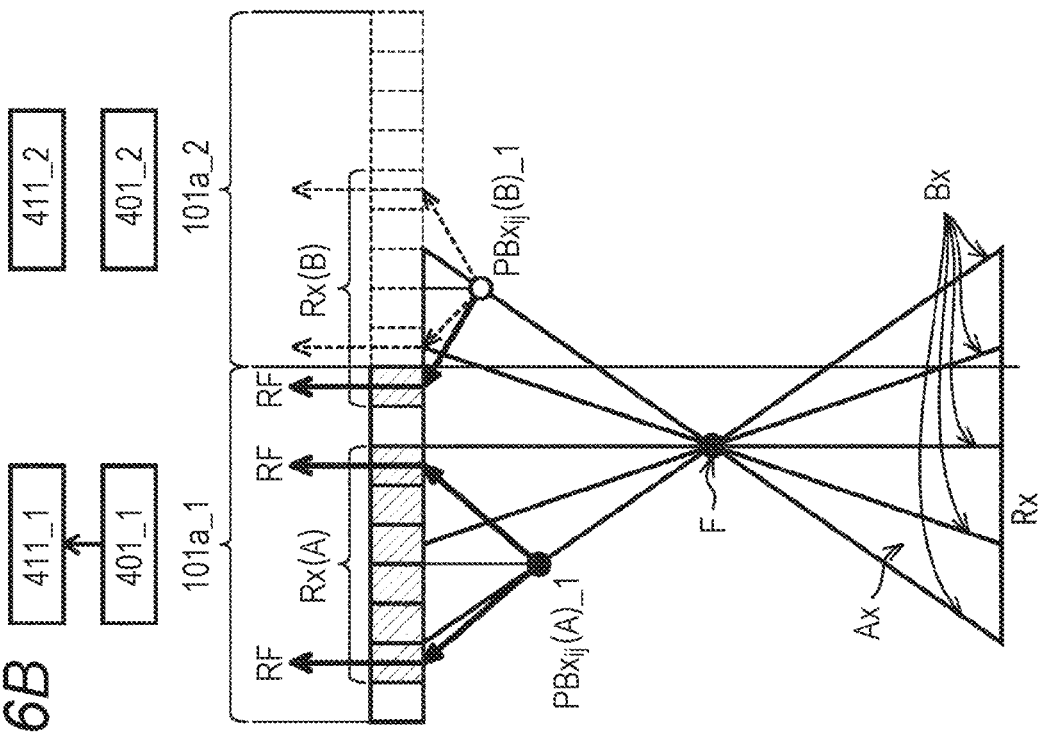
Figure 6B:
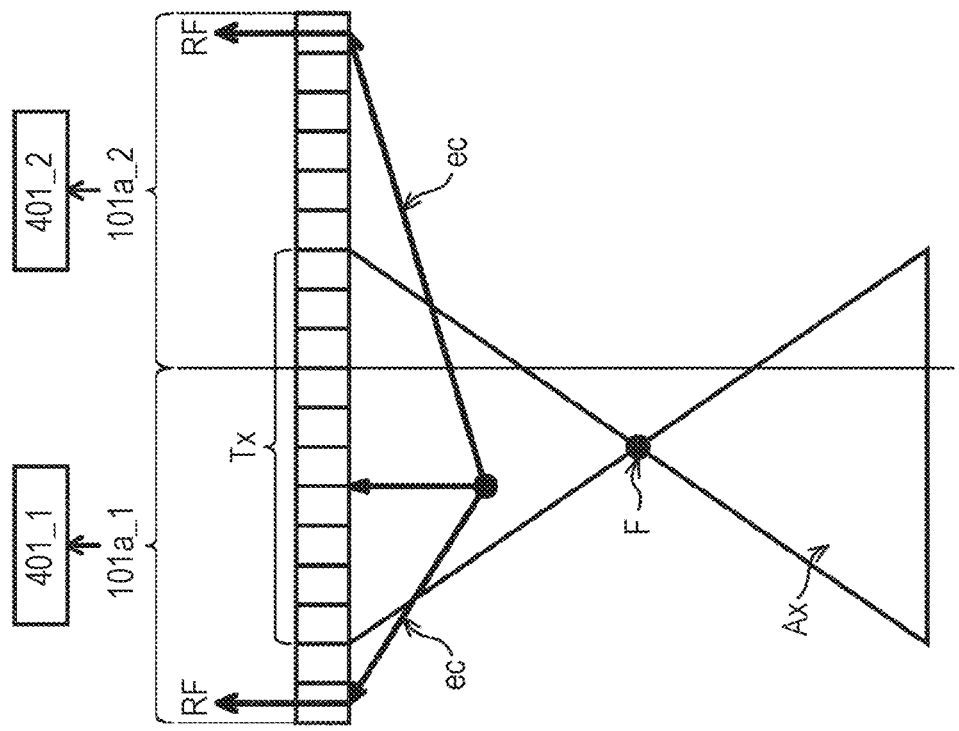

FIGS. 6A to 6C are schematic diagrams illustrating an outline of division processing in the part receiver 401 and the part delay-and-sum part 411 of the delay-and-sum part 41 when the division number n of the partial transducer array 101a_1 is two. FIG. 6A illustrates an acquisition range of the reception signal sequence rf in the part receivers 401_1 and 401_2. Each of FIGS. 6B and 6C illustrates a reference range of the reception signal sequence rf and a presence range of the on-line observation point PBxij on which each of acoustic line signal partial subframe data ds_1 and ds_2 should be generated in the delay-and-sum processing by the part delay-and-sum part 411_1 and by the part delay-and-sum part 411_2, respectively.

In the transmission event, as described above, the transmitter 1031 sets an array of transducers corresponding to all or a part of the plurality of transducers 101*a* present in the probe 101, as the transmit aperture Tx. FIG. 6A is a state where the transmit aperture Tx is positioned across the partial transducer arrays 101*a*_1 and 101*a*_2. The transmitter 1031 causes each of the plurality of transducers included in the transmit aperture Tx to transmit the ultrasound beam so as to converge on the transmission focal point F. The ultrasound beam is diffused after the wavefront is focused at the transmission focal point F to allow the ultrasound main irradiation region Ax to have an hourglass shape with the transmit aperture Tx as an upper edge. Subsequently, a reflected wave ec reflected by a tissue in the ultrasound main irradiation region Ax reaches each of the transducers 101*a*, and the part receivers 401_1 and 401_2 generate the reception signal sequence rf on the basis of the reflected wave ec received by all the transducers included in the partial transducer arrays 101*a*_1 and 101*a*_2, as illustrated in FIG. 6A.

ii) Generating Acoustic Line Signal Partial Subframe Data Ds_1 in Part Delay-and-Sum Part 411_1

Next, as illustrated in FIG. 6B, on the basis of the reception signal sequence rf output by the part receiver 401_1, the part delay-and-sum part 411_1 sets the receive aperture Rx for all the on-line observation points PBxij located on the target line group Bx included in the ultrasound main irradiation region Ax and performs delay-and-sum processing for these points. While the receive aperture Rx will be described below, note that the receive aperture Rx may be selected such that the array center of the transducer array constituting the receive aperture Rx matches the transducer closest to the on-line observation point PBxij.

For example, a receive aperture Rx (A) is selected for an on-line observation point PBxij(A)_1 located within the ultrasound main irradiation region Ax below the partial transducer array 101*a*_1. In this case, for the on-line observation point PBxij(A)_1, delay-and-sum is performed on the basis of the reception signal sequence rf received by the transducer within the receive aperture Rx(A), among the reception signal sequence rf generated by the part receiver 401_1, and acoustic line signal partial data ds_1 for the on-line observation point PBxij(A)_1 is generated. As illustrated in FIG. 6B, the reception signal sequence rf received by the transducer within the receive aperture Rx(A) and calculated by the part receiver 401_1 is based on all transducers of the receive aperture Rx(A). Therefore, the acoustic line signal partial data ds_1 for the on-line observation point PBxij(A)_1 can achieve maximum signal intensity in accordance with the reflectance.

In contrast, a receive aperture Rx(B) is selected for an on-line observation point PBxij(B)_1 located within the ultrasound main irradiation region Ax below the partial transducer array 101*a*_2. In this case, for the on-line observation point PBxij(B)_1, delay-and-sum is performed on the basis of the reception signal sequence rf received by the transducer within the receive aperture Rx(B), among the reception signal sequence rf generated by the part receiver 401_1, and acoustic line signal partial data ds_1 for the on-line observation point PBxij(B)_1 is generated. As illustrated in FIG. 6B, the reception signal sequence rf received by the transducer within the receive aperture Rx(B) and calculated by the part receiver 401_1 is based on a part of the transducers of the receive aperture Rx(B). Accordingly, the acoustic line signal partial data ds_1 for the on-line observation point PBxij(B)_1 can achieve a low signal intensity.

In this manner, the part delay-and-sum part 411_1 generates the acoustic line signal partial subframe data ds_1 for all the on-line observation points PBxij located on the target line group Bx on the basis of the reception signal sequence rf output by the part receiver 401_1.

iii) Generating Acoustic Line Signal Partial Subframe Data Ds_2 in Part Delay-and-Sum Part 411_2

As illustrated in FIG. 6C, on the basis of the reception signal sequence rf output by the part receiver 401_2, the part delay-and-sum part 411_2 sets the receive aperture Rx for all the on-line observation points PBxij located on the target line group Bx and performs delay-and-sum processing for these points.

For example, the receive aperture Rx (B) is selected for the on-line observation point PBxij(B)_2 located below the partial transducer array 101*a*_2. In this case, delay-and-sum is performed for the on-line observation point PBxij(B)_2 on the basis of the reception signal sequence rf received by the transducer within the receive aperture Rx(B), among the reception signal sequence rf generated by the part receiver 401_2, and acoustic line signal partial data ds_2 for the on-line observation point PBxij(B)_2 is generated. As illustrated in FIG. 6C, the reception signal sequence rf received by the transducer within the receive aperture Rx(B) and calculated by the part receiver 401_2 is the reception signal sequence rf based on most transducers of the receive aperture Rx(A). Therefore, the acoustic line signal partial data ds_2 for the on-line observation point PBxij(B)_2 can achieve sufficient signal intensity.

In contrast, the receive aperture Rx(A) is selected for the on-line observation point PBxij(A)_2 located below the partial transducer array 101*a*_1. In this case, for the on-line observation point PBxij(A)_2, delay-and-sum is performed on the basis of the reception signal sequence rf alone received by the transducer within the receive aperture Rx(A), among the reception signal sequence rf generated by the part receiver 401_2, and acoustic line signal partial data ds_2 for the on-line observation point PBxij(A)_2 is generated. As illustrated in FIG. 6C, since there is no reception signal sequence rf received by the transducer in the receive aperture Rx(A) and calculated by the part receiver 401_2, the acoustic line signal partial data ds_2 for the on-line observation point PBxij(A)_2 has a signal intensity of zero.

In this manner, the part delay-and-sum part 411_2 generates the acoustic line signal partial subframe data ds_2 for all the on-line observation points PBxij located on the target line group Bx on the basis of the reception signal sequence rf output by the part receiver 401_2.

The delay-and-sum method in the part delay-and-sum parts 411_1 and 411_2 is implemented by the following equations, where a weighting coefficient by the receiving apodization is ap, intensity of the reception signal is rf, a variable indicating the plurality of transducers 101*a* is k (k is a natural number larger than 1).

[Mathematical Expression 1]
$$ds\_1(i, j) = \sum_{k}^{Rx} ap(k, j) \times rf(k, j + \Delta j(i, j, k))$$

[Mathematical Expression 2]
$$ds\_2(i, j) = \sum_{k}^{Rx} ap(k, j) \times rf(k, j + \Delta j(i, j, k))$$

(2) Configuration of Components of Part Delay-and-Sum Part 411

Figure 7:
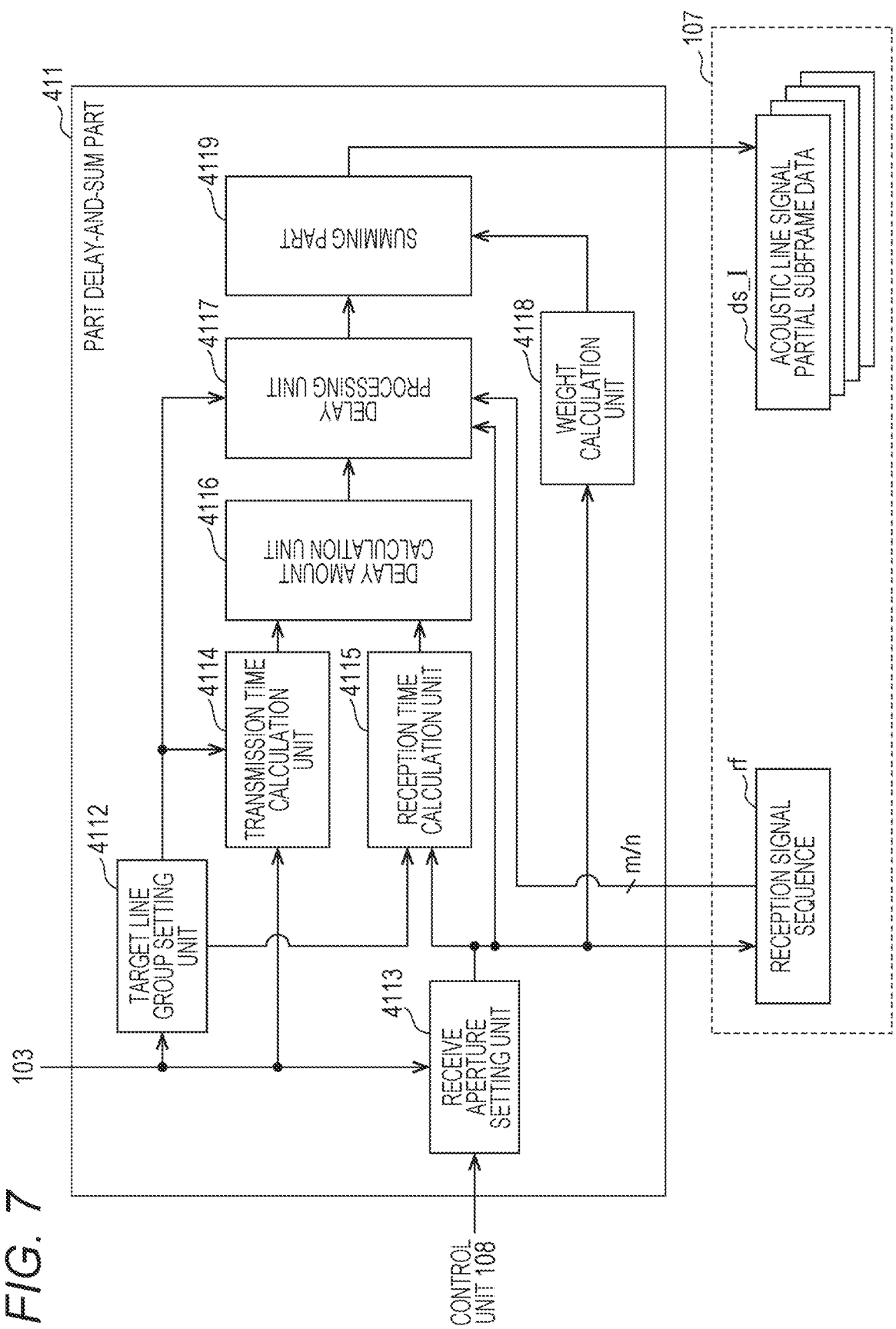
FIG. 7 is a functional block diagram illustrating a configuration of the part delay-and-sum part according to the embodiment.

FIG. 7 is a functional block diagram illustrating a configuration of the part delay-and-sum part 411. As illustrated in FIG. 7, the part delay-and-sum part 411 includes a target line group setting unit 4112, a receive aperture setting unit 4113, a transmission time calculation unit 4114, a reception time calculation unit 4115, a delay amount calculation unit 4116, a delay processing unit 4117, a weight calculation unit 4118, and a summing part 4119.

Hereinafter, a configuration of each of components constituting the part delay-and-sum part 411 will be described.

i) Target Line Group Setting Unit 4112

The target line group setting unit 4112 sets the target line group Bx as a target of generation of the acoustic line signal subframe data in the subject. The "target line group" is a region on a signal where the generation of the acoustic line signal subframe data is to be performed in the subject in synchronization with a transmission event, and an acoustic line signal is generated for the observation point Pij on the target line group Bx. The target line group Bx is set, for convenience of calculation, as a set of observation target points as a target of acoustic line signal generation in synchronization with one transmission event.

As described above, as illustrated in FIG. 4, the part delay-and-sum part 411_1 is divided corresponding to the plurality of partial transducer arrays 101a_1 input from each of the plurality (n) of part receivers 401_1. Therefore, in the present embodiment, the part delay-and-sum part 411_1 obtains the reception signal sequence rf output from the signal sequence received by the partial transducer array 101a_1, as an input signal. However, the delay-and-sum processing in the part delay-and-sum part 411_1 employs a configuration of generating the acoustic line signal partial subframe data ds_1 for all the observation points PBxij on the target line group Bx located in the entire ultrasound main irradiation region Ax.

As an aspect different from the present embodiment, the delay-and-sum processing in the part delay-and-sum part 411_1 may employ a configuration of generating the acoustic line signal partial subframe data ds_1 for observation points located within the range corresponding to the partial transducer arrays 101a_1 among the observation points PBxij on the target line group Bx located in the entire ultrasound main irradiation region Ax.

Note that the "acoustic line signal subframe data" is a set of acoustic line signals for all the observation points Pij present in the target line group Bx generated from one transmission event. Note that "subframe" represents a unit obtained by one transmission event and forming a group of signals corresponding to all the observation points Pij present in the target line group Bx. A frame is obtained by combining a plurality of subframes obtained at mutually different times.

In synchronization with a transmission event, the target line group setting unit 4112 sets the target line group Bx on the basis of the information indicating the position of the transmit aperture Tx obtained from the transmit beamformer unit 103.

Figure 8:
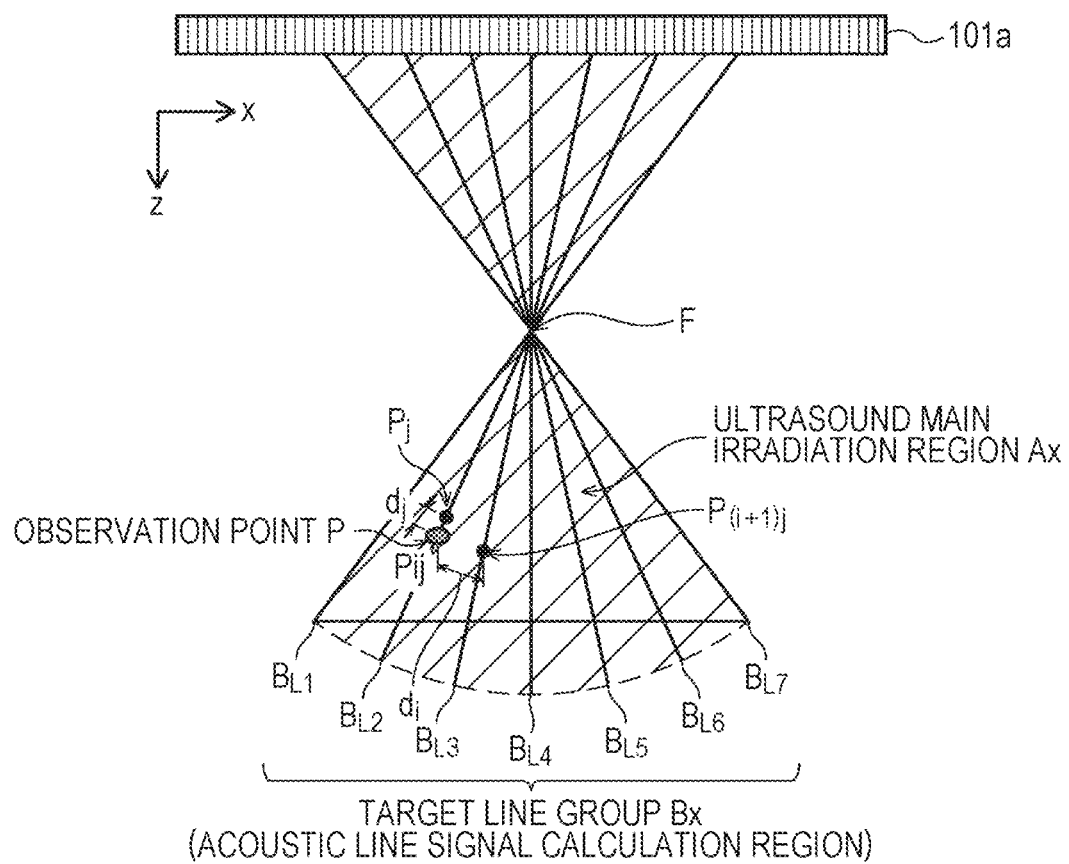
FIG. 8 is a schematic diagram illustrating a target line group Bx.

FIG. 8 is a schematic diagram illustrating the target line group Bx. As illustrated in FIG. 8, the target line group Bx is present in the ultrasound main irradiation region Ax and includes a plurality of target lines BL1 to BL7 (hereinafter, referred to as a "target line BL" in a case where there is no need to distinguish between the individual target lines). Each of the target lines is a straight line passing through the focal point F or its vicinity. Note that the target lines BL1 and BL7 correspond to the outline of the ultrasound main irradiation region Ax, and the target line BL4 presents on the central axis of the transmit aperture Tx. For the sake of convenience, it is assumed herein that the outline of the ultrasound main irradiation region Ax includes two lines, namely, a straight line passing through one end of the transmit aperture Tx and the focal point F, and a straight line passing through the other end of the transmit aperture Tx and the focal point F. Moreover, angles formed by adjacent target lines are substantially equal to each other in each of the target lines BL1 to BL7. That is, the observation points present on the circular arc centered on the focal point F are arranged at equal intervals. Moreover, for example, in a case where i is a variable indicating an identification number of the target line and j is a variable indicating the position along the target line, unless a distance between Pij and the focal point F is below a predetermined distance, a distance dj between adjacent observation points Pij and Pi (j+1) on a same target line BL2 is shorter than a distance di between the observation points Pij and P (i+1) j on the adjacent target lines BL2 and BL3, respectively. The distance dj is at least twice the distance di, preferably 4 or more times, more preferably 8 times or more. With this configuration, the observation points are uniformly arranged in the substantial entire region of the ultrasound main irradiation region Ax such that the observation points are arranged in high density in the depth direction while the observation points are arranged in lower density in a direction in which the transducers are arranged (circumferential direction around the focal point F). Note that the predetermined distance means a range in which the distance between the point on the target line and the point on the target line adjacent to the target line is smaller than the interval between the observation points along the target line. For example, in a case where an angle formed by adjacent target lines is θ, the predetermined distance dp satisfies the following expression.

$$di = 2 \cdot dp \cdot \sin(\theta/2)$$

Note that the shape of the target line group Bx is not limited to the above-described case, and may be determined such that the distances of the positions coming in contact with the transmission transducer array in each of the target lines BL1 to BL7 are equal. In addition, while the target line group Bx includes seven target lines in this example, the number of target lines may be set to any number as long as it is within a range of 3 or more. In addition, while an explanation is given by using odd numbers in this example for the sake of simplicity, the number of target lines is of course not limited to odd numbers.

In addition, while each of the observation points Pij is present on the target line group Bx, a part or all of observation points may be set to a position close to the target line, for example. For example, when i and j are variables indicating orthogonal coordinates, the observation point Pij can be defined as a point present on a grid in the orthogonal coordinates defined by the direction (x-direction) in which the transducers are arranged and the depth direction (z-direction), with the center of each of the transducers being defined as a grid. With this configuration, there is always a transducer with a same x-coordinate for each of the observation points Pij, leading to enhancement of acoustic line signal quality. In this case, since the target line is not necessarily parallel to the z-direction, the target line does not necessarily pass through the grid at a position where the observation point is to be provided in some cases. In such a case, the observation point is not directly above the target line but on a grid close to the target line. For example, the coordinates of the observation points to be provided on the target line are rounded such as rounding off at a predetermined number of digits, thereby defining the actual coordinates of the observation points. Specifically, observation points are determined as follows. In a direction in which the transducers are aligned (x direction), the number of transducers of the probe is 192, the position of the transducer at one end of the transducer array of the probe is x=0, and the position of the transducer at the other end is x=191. In the depth direction, the position of the transducer array is set to z=0, and the deepest point by one transducer of the probe is set to z=1. When the target line passing through the coordinates (31, 0) is set with the coordinates of the focal point F as (64, 1000), the target line is represented by the following mathematical expression.

$$z=(1000/33)\cdot(x-31)$$

At this time, for example, in case of arranging an observation point at a depth of z=1500, the coordinates would be (80.5, 1500). In this case, the observation point may be (81, 1500). With this configuration, it is possible to define the transducer with x=81 as a reference in the delay-and-sum, and it is possible to enhance the quality of the acoustic line signal. The position at which the observation point is actually provided is not limited to the above-described case, and the position may be any position as long as the observation point to be provided on the target line group Bx is obtained by rounding a coordinate value to define a computationally preferable close point as the actual observation point.

The set target line group Bx is output to the transmission time calculation unit 4114, the reception time calculation unit 4115, and the delay processing unit 4117.

ii) Receive Aperture Setting Unit 4113

Figure 9:
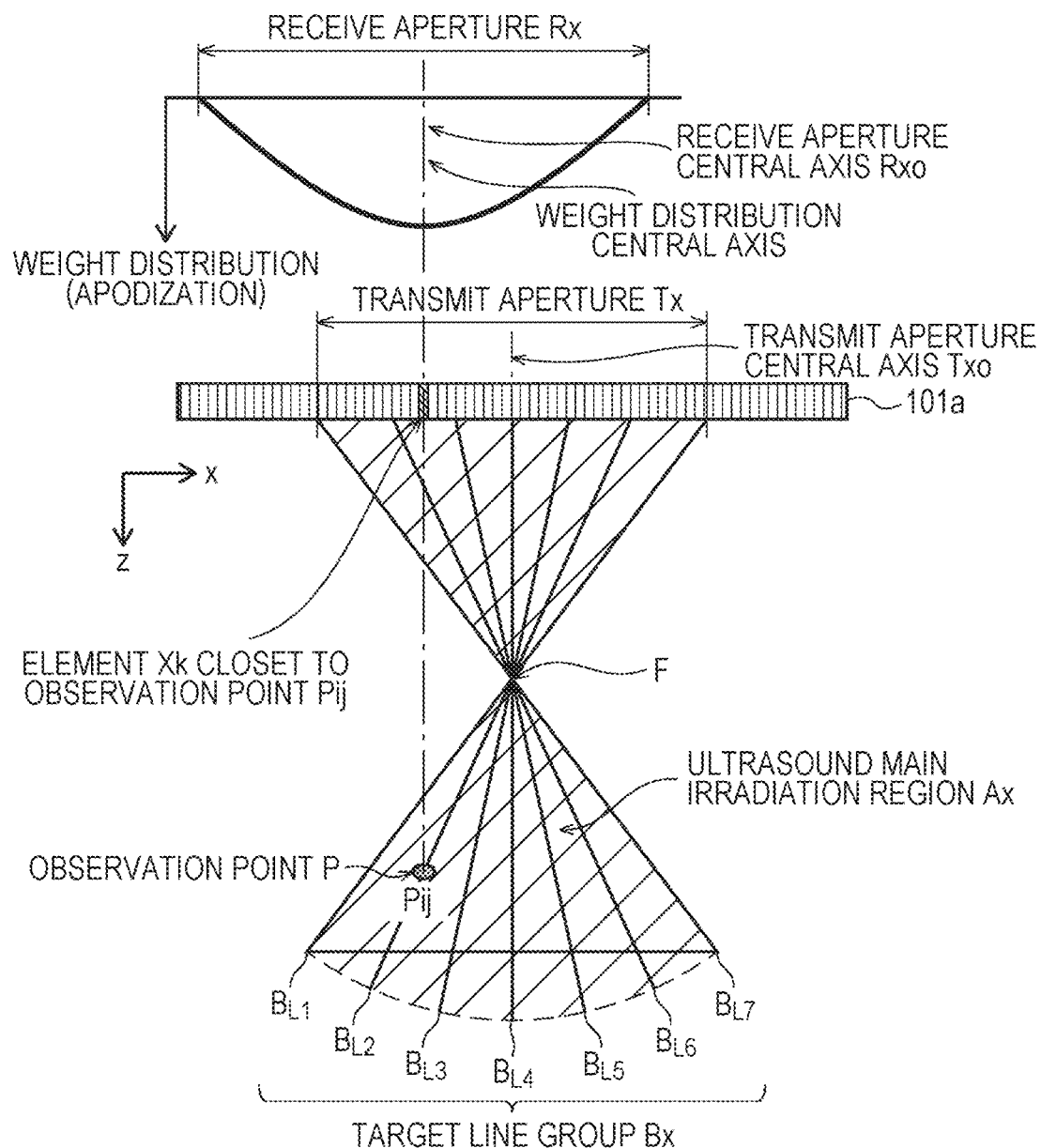
FIG. 9 is a schematic diagram illustrating a relationship between a receive aperture Rx and a transmit aperture Tx set by a receive aperture setting unit.

The receive aperture setting unit 4113 is a circuit that selects a transducer array (reception transducer array) corresponding to a part of the plurality of transducers present in the probe 101 as a reception transducer to set the receive aperture Rx on the basis of a control signal from the control unit 108 and information indicating the position of the transmit aperture Tx from the transmit beamformer unit 103. Note that the "receive aperture Rx" is an array of transducers that have received the reception signal sequence as a target of delay-and-sum in order to generate the acoustic line signal of the on-line observation point PBxij. In the present embodiment, the receive aperture setting unit 4113 selects the receive aperture Rx transducer array such that the array center matches a transducer Xk that is spatially closest to the observation point Pij. FIG. 9 is a schematic diagram illustrating a relationship between the receive aperture Rx and the transmit aperture Tx set by the receive aperture setting unit 4113. As illustrated in FIG. 9, the receive aperture Rx transducer array is selected such that the array center of the receive aperture Rx transducer array matches the transducer Xk which is spatially closest to the observation point Pij. Accordingly, the position of the receive aperture Rx is determined by the position of the observation point Pij, and does not change on the basis of the position of the transmit aperture Tx varying in synchronization with the transmission event. That is, even in different transmission events, in the processing of generating the acoustic line signals for the observation points Pij located at the same position, delay-and-sum is performed on the basis of the reception signals obtained by the reception transducers Rk within the same receive aperture Rx.

Moreover, in order to receive reflected waves from the entire ultrasound main irradiation region Ax, the number of transducers included in the receive aperture Rx is preferably be set to the number of transducers included in the transmit aperture Tx in the corresponding transmission event, or more. The number of transducer arrays constituting the receive aperture Rx may be 32, 64, 96, 128, 192, or the like, for example.

The setting of the receive aperture Rx is performed at least as many times as the transmission event, corresponding to the transmission event. In addition, the setting of the receive aperture Rx may be performed progressively in synchronization with the transmission event, or may be performed after completion of all transmission events, or the setting of the receive aperture Rx corresponding to each of the transmission events may be performed collectively for the number of times of transmission events.

Information indicating the position of the selected receive aperture Rx is output to the data storage 107 via the control unit 108.

The data storage 107 outputs the information indicating the position of the receive aperture Rx and the reception signal corresponding to the reception transducer to the transmission time calculation unit 4114, the reception time calculation unit 4115, the delay processing unit 4117, and the weight calculation unit 4118.

iii) Transmission Time Calculation Unit 4114

The transmission time calculation unit 4114 is a circuit that calculates a transmission time when the transmitted ultrasound wave reaches the observation point Pij in the subject. Corresponding to the transmission event, the transmission time calculation unit 4114 calculates a transmission time when the transmitted ultrasound wave reaches a certain observation point Pij in the subject, the observation point Pij being present on the target line group Bx, on the basis of information indicating the position of the transducer included in the transmit aperture Tx obtained from the data storage 107 and information indicating the position of the target line group Bx including the ultrasound main irradiation region Ax obtained from the target line group setting unit 4112.

Figure 10A:
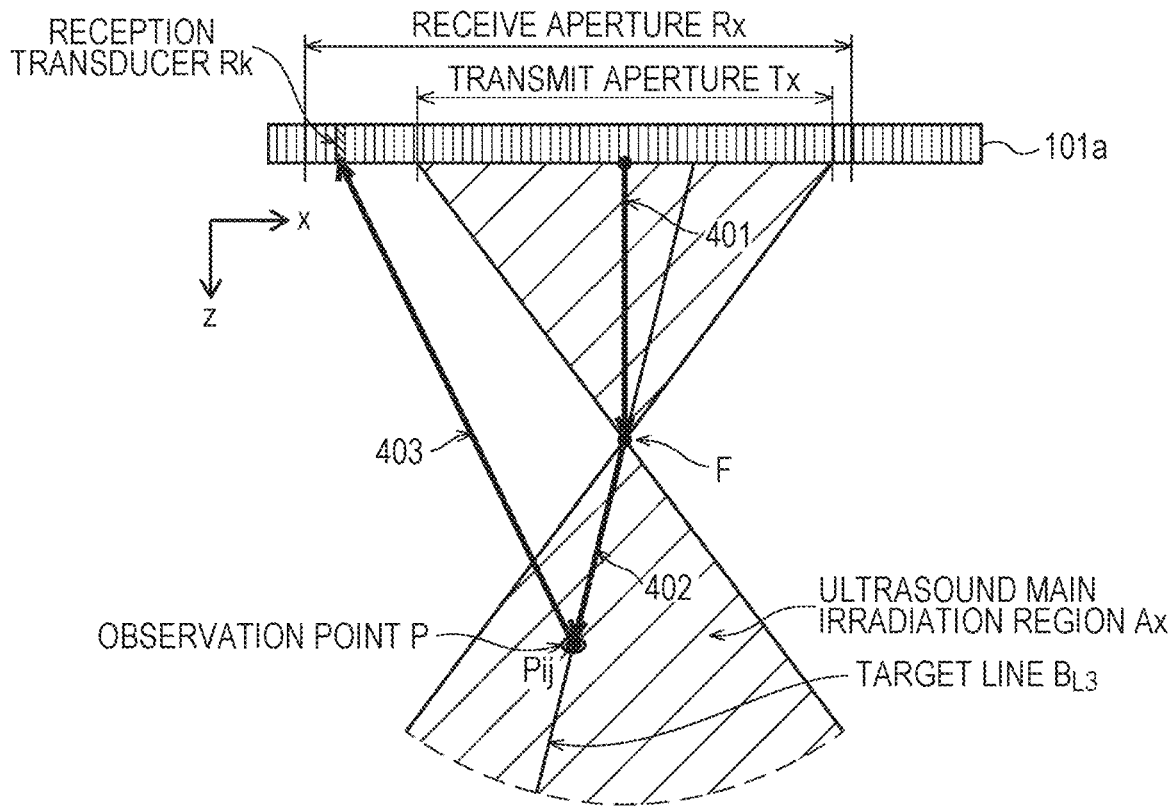
FIGS. 10A and 10B are schematic diagrams illustrating propagation paths of ultrasound waves reaching a reception transducer Rk from the transmit aperture Tx via an observation point Pij.
Figure 10B:
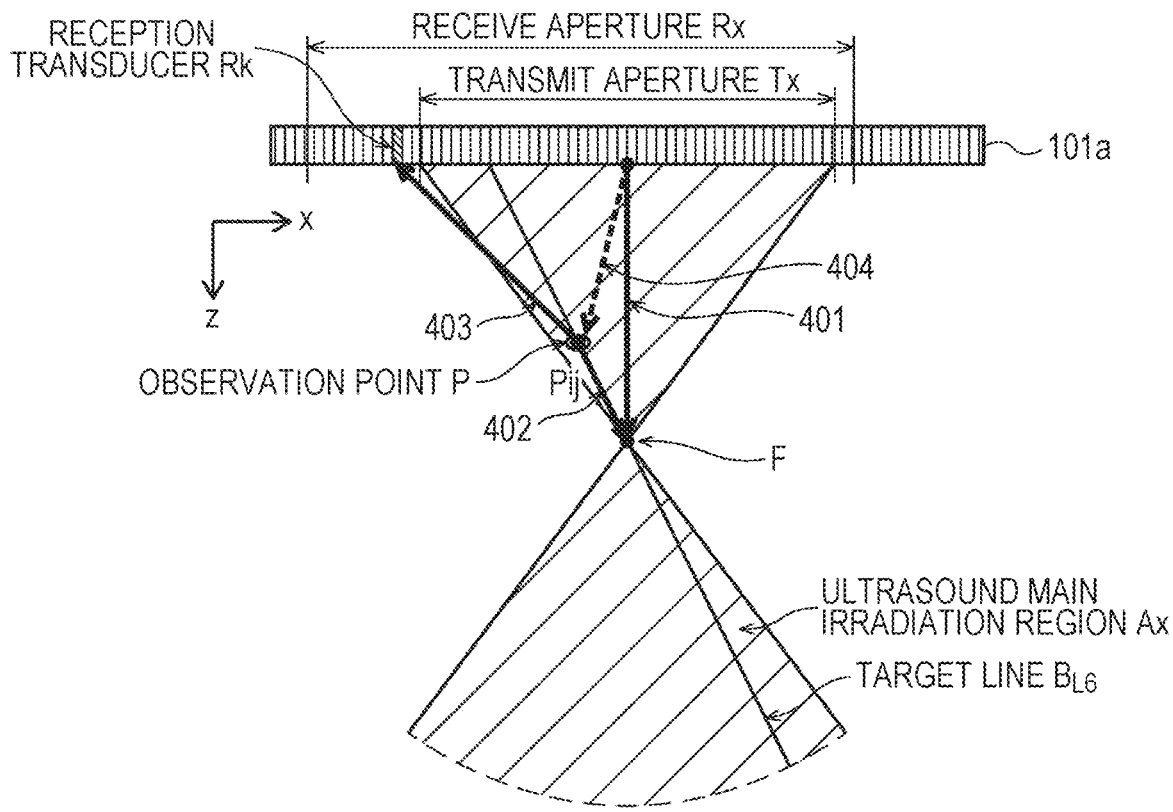

FIGS. 10A and 10B are schematic diagrams illustrating propagation paths of an ultrasound wave emitted from the transmit aperture Tx, reflected on the observation point Pij at a certain position on the target line group Bx to reach the reception transducer Rk located within the receive aperture Rx. FIG. 10A illustrates a case where the depth of the observation point Pij is the focal depth or more, and FIG. 10B illustrates a case where the observation point Pij is less deep than the focal depth.

The transmission wave emitted from the transmit aperture Tx passes through the path 401 and the wavefront converges at the transmission focal point F and diffuses again. The transmission wave reaches the observation point Pij in the middle of converging or diffusing, and generates a reflected wave in a case where the acoustic impedance is changed at the observation point Pij. The reflected wave returns to the reception transducer Rk within the receive aperture Rx in the probe 101. Since the transmission focal point F is defined as a design value of the transmit beamformer unit 103, the length of the path 402 between the transmission focal point F and the certain observation point Pij can be geometrically calculated.

The method of calculating the transmission time will be described in more detail below.

First, the method in a case where the depth of the observation point Pij is the focal depth or more will be described with reference to FIG. 10A. When the depth of the observation point Pij is the focal depth or more, calculation is performed assuming that the transmission wave emitted from the transmit aperture Tx has reached the transmission focal point F via a path 401, and reached the observation point Pij from the transmission focal point F via the path 402. Accordingly, the sum of the time of passing of the transmission wave through the path 401 and the time of passing through the path 402 is the transmission time. As a specific calculation method, for example, the transmission time can be obtained by dividing a total path length obtained by summing the length of the path 401 and the length of the path 402 by a propagation speed of the ultrasound wave in the subject.

In contrast, a case where the observation point Pij is less deep than the focal depth will be described with reference to FIG. 10B. When the observation point Pij is less deep than the focal depth, calculation is performed assuming that a time point at which the transmission wave emitted from the transmit aperture Tx reaches the transmission focal point F via the path 401 is equal to a time point at which the transmission wave reaches the transmission focal point F from the observation point Pij via the path 402 after arrival of the wave at the observation point Pij via a path 404. That is, the value obtained by subtracting the time that the transmission wave passes through the path 402 from the time that the transmission wave passes through the path 401 is the transmission time. As a specific calculation method, for example, the transmission time can be obtained by dividing a total path length obtained by subtracting the length of the path 402 from the length of the path 401 by a propagation speed of the ultrasound wave in the subject.

The transmission time in a case where the observation point Pij is the focal depth is calculated with the same calculation method as in a case where the observation point Pij is deeper than the focal depth, that is, the method of adding the time that the transmission wave passes through the path 401 and the time that the wave passes through the path 402. Still, the time may be calculated with the same calculation method as in a case where the observation point Pij is less deep than the focal depth, that is, the method of subtracting the time that the transmission wave passes through the path 402 from the time that the wave passes through the path 401. This is because the length of the path 402 becomes 0, and the time matches the time of passing through the path 401 by any of the calculation methods.

The transmission time calculation unit 4114 calculates the transmission time when the transmitted ultrasound waves reach the observation point Pij in the subject with respect to all the observation points Pij on the target line group Bx for one transmission event, and outputs the calculated time to the delay amount calculation unit 4116.

iv) Reception Time Calculation Unit 4115

The reception time calculation unit 4115 is a circuit that calculates the reception time when the reflected wave from the observation point P reaches each of the reception transducers Rk included in the receive aperture Rx. Corresponding to the transmission event, the reception time calculation unit 4115 calculates a reception time when the transmitted ultrasound wave reaches each of the reception transducers Rk of the receive aperture Rx after being reflected on a certain observation point Pij in the subject, the observation point Pij being present on the target line group Bx, on the basis of information indicating the position of the reception transducer Rk obtained from the data storage 107 and information indicating the position of the target line group Bx obtained from the target line group setting unit 4112.

As described above, the transmission wave that has reached the observation point Pij generates a reflected wave in a case where the acoustic impedance is changed at the observation point Pij. The reflected wave returns to the reception transducer Rk within the receive aperture Rx in the probe 101. Since the position information of each of the reception transducers Rk within the receive aperture Rx is obtained from the data storage 107, the length of the path 403 from a certain observation point Pij to each of the reception transducers Rk can be geometrically calculated.

The reception time calculation unit 4115 calculates the reception time when the transmitted ultrasound waves reach each of the reception transducer Rk after being reflected on the observation points Pij for all the observation points Pij present on the target line group Bx for one transmission event, and outputs the calculated time to the delay amount calculation unit 4116.

v) Delay Amount Calculation Unit 4116

The delay amount calculation unit 4116 is a circuit that calculates the total propagation time to reach each of the reception transducers Ri within the receive aperture Rx on the basis of the transmission time and the reception time and that calculates a delay time to be applied to a reception signal sequence corresponding to each of the reception transducers Rk on the basis of the total propagation time. The delay amount calculation unit 4116 obtains the transmission time when the ultrasound wave transmitted from the transmission time calculation unit 4114 reaches the observation point Pij and the reception time when the ultrasound wave reflected by the observation point Pij reaches each of the reception transducers Rk. The delay amount calculation unit 4116 subsequently calculates the total propagation time until the transmitted ultrasound wave reaches each of the reception transducers Rk, and then calculates the delay amount for each of the reception transducers Rk on the basis of the difference in the total propagation time for each of the reception transducers Rk. The delay amount calculation unit 4116 calculates the delay amount to be applied to the reception signal sequence for each of the reception transducers Ri on all the observation points Pij present on the target line group Bx, and outputs the delay amount to the delay processing unit 4117.

vi) Delay Processing Unit 4117

The delay processing unit 4117 is a circuit that identifies a reception signal corresponding to a delay amount for each of the reception transducers Rk from a sequence of reception signals for the reception transducers Rk in the receive aperture Rx as a reception signal corresponding to the reception transducer Rk based on the reflected ultrasound wave from the observation point Pij.

Corresponding to the transmission event, the delay processing unit 4117 obtains, as inputs: information indicating the position of the reception transducer Rk from the receive aperture setting unit 4113; a reception signal corresponding to the reception transducer Rk from the data storage 107; information indicating the position of the target line group Bx obtained from the target line group setting unit 4112; and the delay amount to be applied to the reception signal sequence for each of the reception transducers Rk from the delay amount calculation unit 4116. The delay processing unit 4117A subsequently identifies the reception signal corresponding to the time obtained by subtracting the delay amount for each of the reception transducers Rk from the reception signal sequence corresponding to each of the reception transducers Rk as the reception signal based on the reflected wave from the observation point Pij, and outputs the signal to the summing part 4119.

vii) Weight Calculation Unit 4118

The weight calculation unit 4118 is a circuit that calculates a weighted numerical sequence (reception apodization)

for each of the reception transducers Rk so as to maximize the weight for the transducer positioned at the center in the array direction of the receive aperture Rx.

As illustrated in FIG. 9, the weighted numerical sequence is a sequence of weighting coefficients to be applied to the reception signal corresponding to each of the transducers in the receive aperture Rx. The weighted numerical sequence has a symmetric distribution around the transmission focal point F as a center. The shape of the distribution of the weighted numerical sequence may be a hamming window, a hanning window, a rectangular window or the like, and the shape of the distribution is not particularly limited. The weighted numerical sequence is set to maximize the weight for the transducer located at the center of the receive aperture Rx in the array direction, and the central axis of the weight distribution matches a receive aperture central axis Rxo, with the distribution having a symmetric shape with respect to the central axis. The weight calculation unit 4118 calculates a weighted numerical sequence for each of the reception transducers Rk as information indicating the position of the reception transducer Rk output from the receive aperture setting unit 4113 as an input, and outputs the result to the summing part 4119.

viii) Summing Part 4119

The summing part 4119 is a circuit that sums the reception signals identified corresponding to each of the reception transducers Rk output from the delay processing unit 4117 as inputs to generate a delay-and-summed acoustic line signals for the observation point Pij. Alternatively, it is allowable to provide a configuration of obtaining a sum by using a weighted numerical sequence for each of the reception transducers Rk output from the weight calculation unit 4118 as an input, and by multiplying the identified reception signal corresponding to each of the reception transducers Rk by the weight for each of the reception transducers Rk to generate the acoustic line signal for the observation point Pij. With a configuration to employ the processing by the delay processing unit 4117 to phase the reception signals detected by the individual reception transducers Rk located in the receive aperture Rx and then employ the summing processing by the summing part 4119, it is possible to superimpose the reception signals received by the individual reception transducers Rk with each other to increase the signal S/N ratio on the basis of the reflected wave from the observation point Pij, enabling extraction of the reception signal from the observation point Pij.

With the processing of one transmission event and the associated processing by the part delay-and-sum part 411_1, it is possible to generate the acoustic line signal partial subframe data ds_1 for all the observation points PBxij on the target line group Bx among the plurality of intra-region observation points Pij located in the entire ultrasound main irradiation region Ax corresponding to each of the plurality of partial transducer arrays 101a_1.

3.2.2.2 Part Folding Part 412

The part folding part 4121 is a circuit that uses the acoustic line signal partial subframe data ds_1 corresponding to each of the plurality of partial transducer arrays 101a_1 generated by the part delay-and-sum part 411_1 as an input to arrange the acoustic line signal ds (i, j) for the plurality of on-line observation points PBxij with reduced intervals between the target lines BL constituting the target line group Bx so as to generate acoustic line signal partial subframe folded data dsc_1s.

Figure 11:
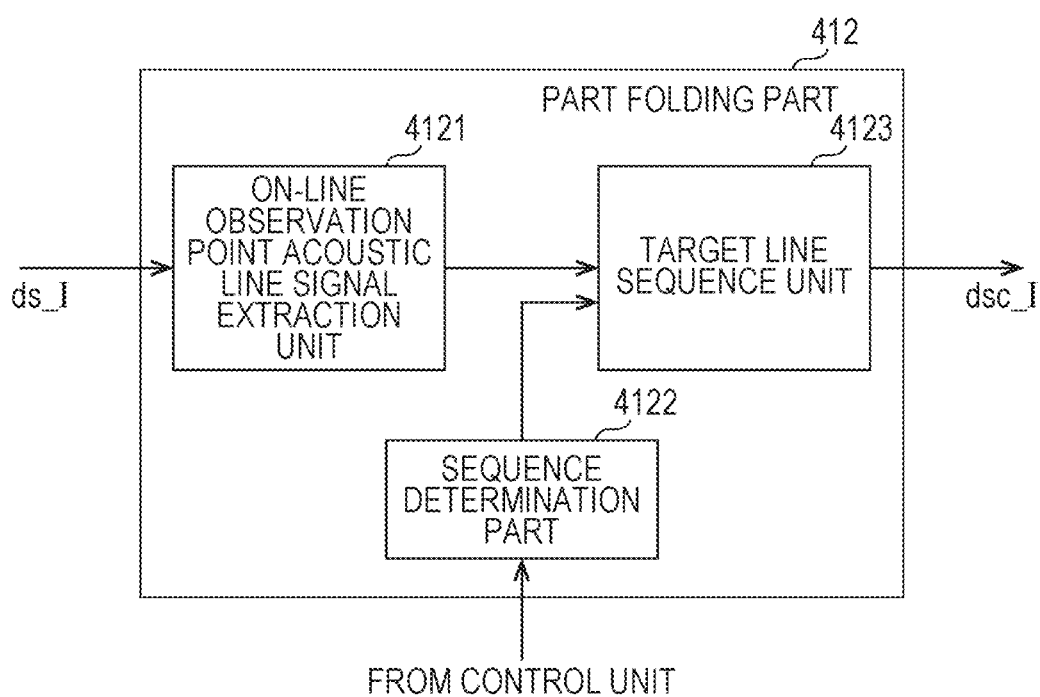
FIG. 11 is a functional block diagram illustrating a configuration of a part folding part according to the embodiment.

FIG. 11 is a functional block diagram illustrating a configuration of the part folding part 412 according to the embodiment. As illustrated in FIG. 11, the part folding part 412 includes an on-line observation point acoustic line signal extraction unit 4121, a sequence determination part 4122, and a target line sequence unit 4123.

i) On-Line Observation Point Acoustic Line Signal Extraction Unit 4121

The on-line observation point acoustic line signal extraction unit 4121 extracts the acoustic line signal ds (i, j) for the on-line observation point PBxij using the acoustic line signal partial subframe data ds_1 as an input.

FIGS. 12A to 12D are explanatory diagrams illustrating operation of the part folding part 412. As illustrated in FIG. 12A, the part delay-and-sum part 411-1 (for example, l=1 or 2) performs delay-and-sum processing with the on-line observation point PBxij set on the target line group Bx (BL1 to BL7) located on the entire ultrasound main irradiation region Ax, from the partial transducer arrays 101a_1 and 101a_2. At this time, the aspect of the acoustic line signal partial subframe data ds_1 (l=1 or 2) generated by the part delay-and-sum part 411_1 or 411_2 is as illustrated in the schematic diagram of FIG. 12B. The acoustic line signal partial subframe data ds_1 is a set of 13×29 (in the case of the present example) acoustic line signal data mapped on an orthogonal coordinate (i, j) (where i corresponds to the transducer array direction (x), and j corresponds to depth (z)) having two axes in the transducer array direction (x) and the depth (z). Among these, 121 calculated acoustic line signals ds (i, j) ("●" in FIG. 12B) are interpolated in the on-line observation point PBxij located in the vicinity of the target line group Bx in FIG. 12B, while a fixed value ds0 ("○" in FIG. 12B) indicating 256 zeros is interpolated in the observation points other than the on-line observation point PBxij. Each of the acoustic line signal ds (i, j) includes coordinate information (i, j) indicating the transducer array direction (x) and the depth (z) in addition to the information indicating the acoustic line intensity.

The on-line observation point acoustic line signal extraction unit 4121 scans the acoustic line signal partial subframe data ds_1 at each of positions of j with respect to each of positions of i, for example, so as to search for an acoustic line signal ds (i, j) in the acoustic line signal partial subframe data ds_1 (i, j). In a case where the acoustic line signal ds (i, j) (marked with "●" in FIG. 12B) is detected, an identification number s to identify the target line BL from the target line group Bx (BL1 to BL7) is assigned to extract the acoustic line signal ds (i, j) for the on-line observation point PBxij. In the example illustrated in FIGS. 12A and 12B, identification numbers of s=−2, −1, 0, 1, and 2 are assigned to the target lines BL1, 2, 3, 4, 5, 6, and 7. Subsequently, the identification number s is added as additional information to each of the acoustic line signals ds (i, j) on the acoustic line signal partial subframe data ds_1. With this configuration, each of acoustic line signals dsc (s, j, i) is a signal containing coordinate information (i, j) indicating the transducer array direction (x) and the depth (z), and information indicating the identification number s of the target line BL in the target line group Bx in addition to the information indicating the acoustic line intensity.

ii) Target Line Sequence Unit 4123

The target line sequence unit 4123 sequences the acoustic line signal ds (i, j) for the extracted on-line observation point PBxij with reduced intervals between the target lines BL in the target line group Bx. More specifically, for example, as illustrated in FIG. 12C, an acoustic line signal dsc (s, j, i) to which an identification number s is added is sequenced on the orthogonal coordinate (s, j) having two axes of s and j (where s corresponds to the transducer array direction (x), and j corresponds to depth (z)), so as to generate acoustic line signal partial subframe folded data dsc_1 having reduced intervals between the target lines BL. Alternatively, as illustrated in FIG. 12D, it is allowable to generate the acoustic line signal partial subframe folded data dsc_1 by performing sequencing in an orthogonal coordinate having an absolute value of the identification number s, and j, as two axes. The orthogonal coordinate (s, j) includes a sequence of 121 acoustic line signals dsc (s, j, i) for the on-line observation point PBxij with reduced intervals between the target lines BL, having values ds0 indicating 24 zeros interpolated in portions other than the acoustic line signal dsc (s, j, i).

As described above, the acoustic line signal partial subframe folded data dsc_1 is a sequence of the acoustic line signal ds (i, j) for the on-line observation point PBxij, having reduced intervals between the target lines BL, making it possible to reduce the data amount, enabling downscaling of necessary internal memory capacity and data transmission capability. Specifically, in the example illustrated in FIGS. 12C and 12D, the acoustic line signal partial subframe folded data dsc_1 is a set of 5×29 pieces of acoustic line signal data on the orthogonal coordinate (s, j), and it can be seen that the data amount is reduced to 5/13 (about 38.5%) as compared with the acoustic line signal partial subframe data ds_1.

iii) Sequence Determination Part 4122

On the basis of the information from the control unit 108, the sequence determination part 4122 determines sequence information to define a sequence method of the acoustic line signals on the target line group in the target line sequence unit 4123 on the basis of various types of information indicating ultrasound measurement conditions for the ultrasound diagnostic apparatus 100, and outputs the sequence information to the target line sequence unit 4123. Subsequently, the target line sequence unit 4123 generates the acoustic line signal partial subframe folded data dsc_1 on the basis of the sequence information. At this time, the sequence determination part 4122 can utilize, as the ultrasound measurement conditions, one or more types of information selected from: bandwidth (transmission/reception frequency range), the number of channels (number of transducers), a channel pitch (transducer interval), shape information (convex, linear etc.), transmit aperture (transmission transducer array), transmission frequency, focus position, transmission interval, steering angle, receive aperture (reception transducer array), maximum depth, set sound speed, mode type (B-mode, C-mode, D-mode, E-mode, and THI), sampling frequency, resolution, PRF, transmission interval, density, hardware computation capability, transmission capability, and the type of operation mode (image quality priority operation mode, frame rate priority operation mode, balance operation mode, low power operation mode). This configuration enables the target line sequence unit 4123 to sequence acoustic line signal sequence for each of the target lines in such an aspect as to conform to the ultrasound measurement conditions, making it possible to reduce the computation amount in the delay-and-sum and the data amount of the generated acoustic line signal in accordance with the ultrasound measurement conditions while suppressing degradation in the spatial resolution and the S/N ratio.

3.2.2.3 Main Summing Part 413

The main summing part 413 sums the acoustic line signal partial subframe folded data dsc_1 corresponding to each of the plurality of partial transducer arrays 101a_1 on the basis of the position of the observation point on an orthogonal coordinate (s, j) having the absolute value of the identification number s and the depth (z) as two axes so as to generate the acoustic line signal subframe folded data dsc and output the data to the data storage 107.

3.2.2.4 Re-Sequence Part 414

The re-sequence part 414 is a circuit that re-sequences the acoustic line signal dsc (s, j, i) in acoustic line signal subframe folded data dsc_sf onto the position of the on-line observation point PBxij in the ultrasound main irradiation region Ax to generate acoustic line signal subframe data ds_sf. As described above, the acoustic line signal dsc (s, j, i) on the acoustic line signal partial subframe folded data dsc_1 includes information indicating the acoustic line intensity, coordinate information (i, j) indicating the transducer array direction (x) and the depth (z), and information indicating the identification number s of the target line BL. Therefore, the acoustic line signal dsc (s, j, i) on the acoustic line signal subframe folded data dsc obtained by summing the acoustic line signal partial subframe folded data dsc_1 also includes information indicating the acoustic line intensity, coordinate information (i, j) indicating the transducer array direction (x) and the depth (z), and information indicating the identification number s of the target line BL.

Figure 13:
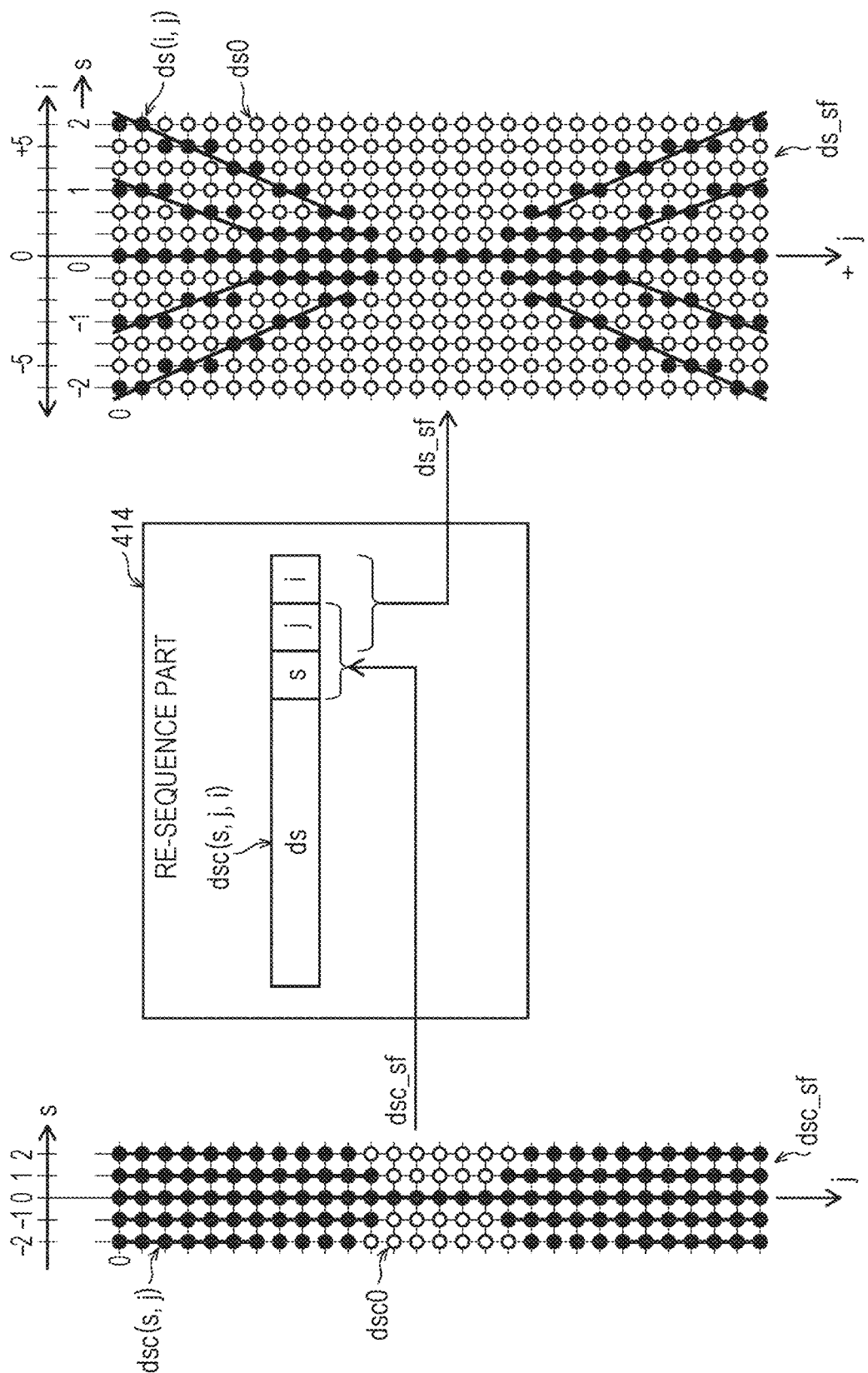
FIG. 13 is an explanatory diagram illustrating operation of a re-sequence part.

FIG. 13 is an explanatory diagram illustrating operation of the re-sequence part 414. Therefore, as illustrated in FIG. 13, the re-sequence part 414 uses the acoustic line signal subframe folded data dsc_sf as an input and re-sequences the acoustic line signal dsc (s, j, i) onto the position of the on-line observation point PBxij on the orthogonal coordinate (i, j) to generate the acoustic line signal subframe data ds_sf by interpolating fixed value ds0 indicating zero to a potions other than the on-line observation point PBxij.

On the basis of the single transmission event and the accompanying processing, the delay-and-sum part 41 generates acoustic line signal subframe data ds_sf for all the observation points Pij present on the target line group Bx in synchronization with the transmission event. The generated acoustic line signal subframe data ds_sf is output to and stored in the data storage 107.

FIG. 6D is a schematic diagram illustrating an outline of generation of the acoustic line signal subframe data ds_sf. When the data before/after folding-summing-unfolding processing in the part folding parts 412_1 and 412_2, the main summing part 413 and the re-sequence part 414 (hereinafter, referred to as "folding-summing-unfolding processing") are compared with each other, the acoustic line signal partial data ds_1 generated by the part delay-and-sum part 411_1 and the acoustic line signal partial data ds_2 generated by the part delay-and-sum part 411_2 are arithmetically summed on the basis of the position of the on-line observation point PBxij so as to generate the acoustic line signal subframe data ds_sf for all the on-line observation points PBxij present within the ultrasound main irradiation region Ax.

Specifically, as illustrated in FIG. 6C, the acoustic line signal partial data ds_1 for the on-line observation points PBxij(A)_1 and PBxij(B)_1 generated by the part delay-and-sum part 411_1 and the acoustic line signal partial data ds_2 for the on-line observation points PBxij(A)_2 and PBxij(B)_2 generated by the part delay-and-sum part 411_2 are arithmetically summed to generate the acoustic line signal data ds_1+2 for the on-line observation points PBxij (A) and PBxij(B). This enables acquisition of the acoustic line signal data ds_1+2 having sufficient signal intensity in each of the on-line observation points PBxij (A) and PBxij (B). Subsequently, such folding-addition-unfolding processing is performed on all the on-line observation points PBxij to generate the acoustic line signal subframe data ds_sf. The summing processing is represented by the following equation.

[Mathematical Expression 3]

$$ds(i, j) = \begin{cases} ds\_1(i, j) \\ + \\ ds\_2(i, j) \end{cases}$$

3.2.3 Combiner 42

The acoustic line signal frame data ds_f as combined acoustic line signal for one frame is generated by repeating the ultrasound transmission while sequentially moving the transmit aperture Tx in the array direction in synchronization with the transmission event so as to perform transmission of the ultrasound waves from all the transducers 101a present in the probe 101. Hereinafter, the combined acoustic line signal for each of the observation points, constituting the acoustic line signal frame data, will be referred to as a "combined acoustic line signal".

Figure 14:
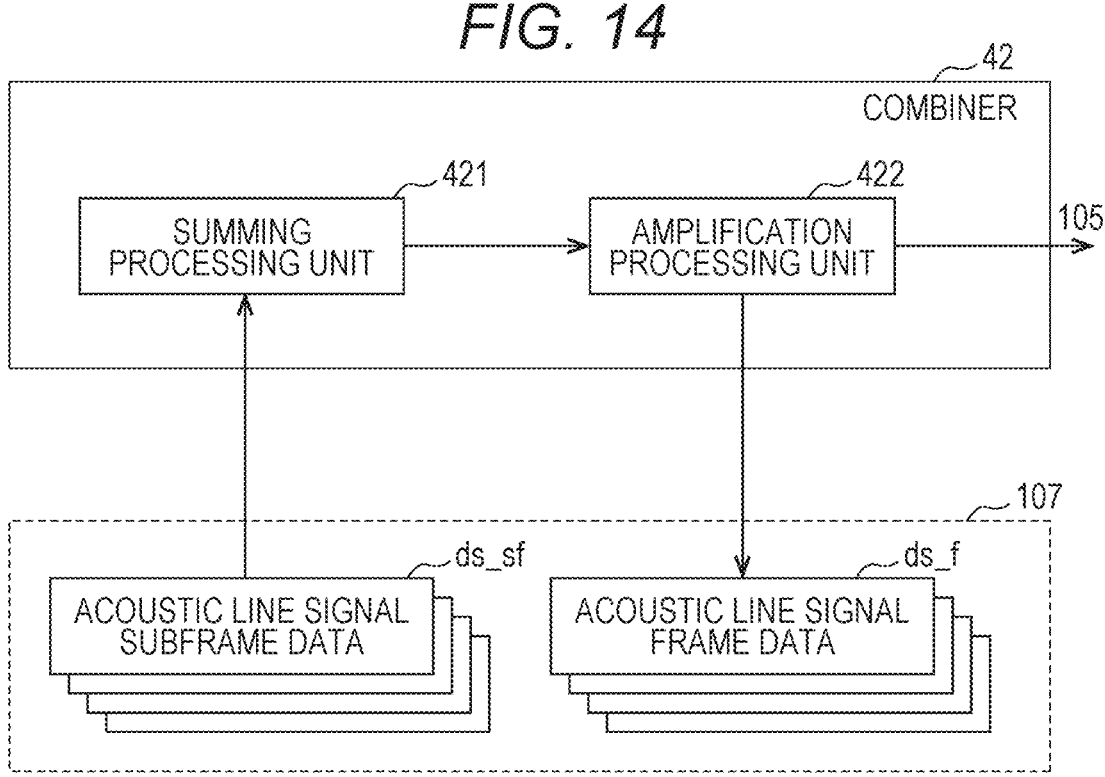
FIG. 14 is a functional block diagram illustrating a configuration of a combiner according to the embodiment.

The combiner 42 is a circuit that combines the acoustic line signal subframe data ds_sf generated in synchronization with the transmission event into the acoustic line signal frame data ds_f. FIG. 14 is a functional block diagram illustrating the configuration of the combiner 42. As illustrated in FIG. 14, the combiner 42 includes a summing processing unit 421 and an amplification processing unit 422.

Hereinafter, the configuration of each of components constituting the combiner 42 will be described.

i) Summing Processing Unit 421

After completion of generation of a series of acoustic line signal subframe data ds_sf for combining the acoustic line signal frame data, the summing processing unit 421 reads a plurality of pieces of acoustic line signal subframe data ds_sf held in the data storage 107. Subsequently, by summing the plurality of pieces of acoustic line signal subframe data ds_sf with the position of the observation point Pij where the acoustic line signal included in each of acoustic line signal subframe data ds_sf is obtained, as an index, a combined acoustic line signal for each of the observation points is generated to be combined as the acoustic line signal frame data ds_f. Therefore, the acoustic line signals for the observation points at the same position included in the plurality of acoustic line signal subframe data ds_sf are summed to generate a combined acoustic line signal.

Figure 15:
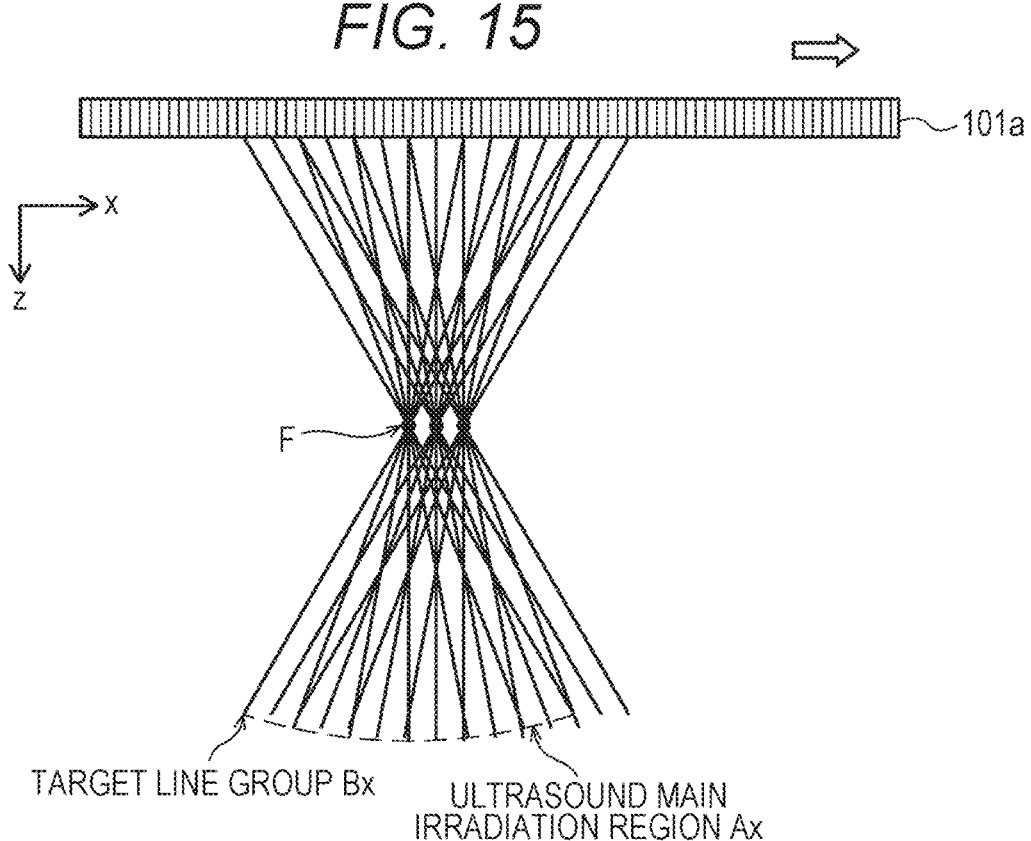
FIG. 15 is a schematic diagram illustrating processing of combining combined acoustic line signals in the summing processing unit.

FIG. 15 is a schematic diagram illustrating a processing of combining combined acoustic line signals in the summing processing unit 421. As described above, ultrasound transmission is sequentially performed by changing the transducer used for the transmission transducer array (transmit aperture Tx) by one transducer in the transducer array direction in synchronization with the transmission event. Accordingly, the positions of the target line group Bx based on different transmission events also changes by one transducer in the same direction for each of the transmission events. By summing a plurality of pieces of acoustic line signal subframe data ds_sf with the position of the observation point Pij where the acoustic line signal included in each of the acoustic line signal subframe data ds_sf was obtained, as an index, acoustic line signal frame data covering all the target line groups Bx is combined.

Moreover, in the case of the observation points Pij extend over the plurality of target line groups Bx located at different positions, the values of the acoustic line signals in the individual acoustic line signal subframe data ds_sf are summed. Accordingly, the combined acoustic line signals are very large value depending on the degree of extension. Hereinafter, the number of times that the observation points Pij are included in mutually different target line groups Bx is referred to as the "number of superimpositions", and the maximum value of the number of superimpositions in the transducer array direction will be referred to as a "maximum superimposition number".

FIG. 16A is a schematic diagram illustrating the maximum number of superimpositions in the combined acoustic line signals and an outline of amplification processing in the amplification processing unit 422. In the present embodiment, the target line group Bx is present within the hourglass-shaped region. Therefore, as illustrated in FIG. 16A, since the number of superimpositions and the maximum number of superimpositions change in the depth direction of the subject, the value of the combined acoustic line signal also changes in the depth direction. Note that in the embodiment of the present invention, in a case where the number of target line groups is 11, for example, the maximum number of superimpositions is consequently limited to 11 at the most.

When the position of the observation point Pij where the acoustic line signal included in each of the acoustic line signal subframe data ds_sf was obtained is summed as an index, it is allowable to perform summing while weighting with the position of the observation point Pij as an index.

The combined acoustic line signal frame data ds_f is output to the amplification processing unit 422.

ii) Amplification Processing Unit 422

As described above, the value of the combined acoustic line signal changes in the depth direction of the subject. To compensate for this, the amplification processing unit 422 multiplies each of the combined acoustic line signals by an amplification factor determined in accordance with the number of times of summing in combining the combined acoustic line signals included in the acoustic line signal frame data ds_f.

FIG. 16B is a schematic diagram illustrating an outline of the amplification processing in the amplification processing unit 422. As illustrated in FIG. 16B, since the maximum number of superimpositions changes in the depth direction of the subject, the combined acoustic line signal is multiplied by an amplification factor that varies in the subject depth direction determined in accordance with the maximum number of superimpositions so as to compensate for the change. As a result, the factor of variation in the combined acoustic line signal due to the change in the number of superimpositions in the depth direction is eliminated, leading to achievement of uniformity in the value of the combined acoustic line signal after the amplification processing in the depth direction.

In addition, it is allowable to perform processing of multiplying the combined acoustic line signal by an amplification factor that varies in the transducer array direction determined in accordance with the number of superimpositions. This eliminates the factor of the variation in a case where the number of superimpositions changes in the transducer array direction, leading to achievement of uniformity in the value of the combined acoustic line signal after the amplification processing in the transducer array direction.

Note that a signal obtained by performing amplification processing on a combined acoustic line signal for each of the generated observation points may be used as the acoustic line signal frame data.

4. Operation

Operation of the ultrasound diagnostic apparatus 100 having the above configuration will be described.

Figure 17B:
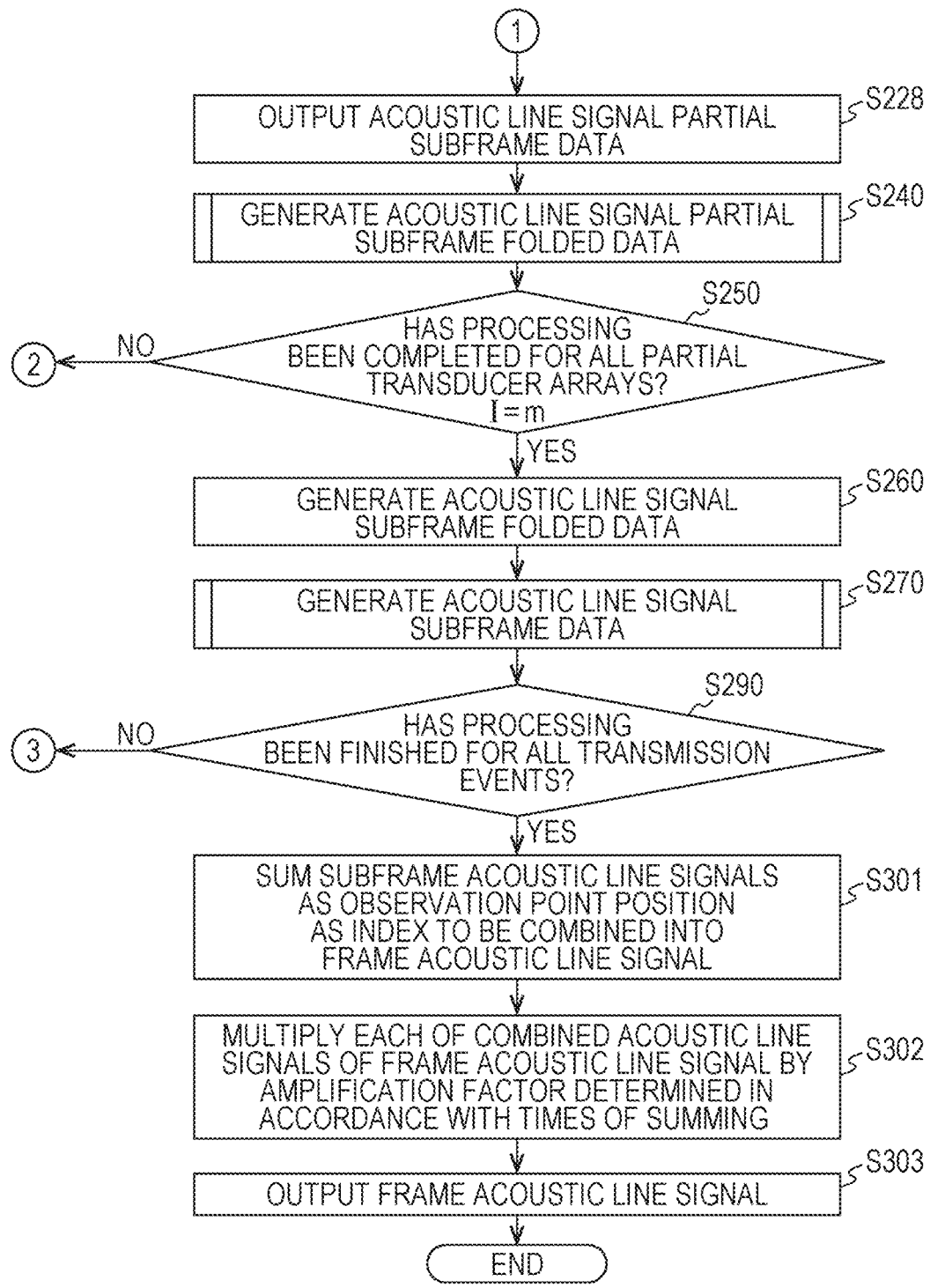

FIGS. 17A and 17B are flowcharts illustrating beamforming processing operation of the receive beamformer unit 104.

In step S101, the transmitter 1031 performs transmission processing (transmission event) of supplying a transmission signal to each of the transducers included in the transmit aperture Tx among the plurality of transducers 101a present in the probe 101, to cause the transducer to transmit the ultrasound beam.

Next, in step S102, the receiver 40 generates a reception signal on the basis of the electric signal obtained from the reception of the ultrasound reflected wave by the probe 101, outputs the reception signal to the data storage 107, and stores the generated signal in the data storage 107. It is determined whether the ultrasound transmission from all the transducers 101a present in the probe 101 has been completed (step S103). In a case where it is not completed (No in step S103), the processing returns to step S101, a transmission event is performed while moving the transmit aperture Tx by one transducer in the array direction. In a case where it is completed (step S103, Yes), the processing proceeds to step S201.

Next, in step S210, the target line group setting unit 411_2 sets the target line group Bx on the basis of information indicating the position of the transmit aperture Tx in synchronization with the transmission event. In a first loop, the target line group Bx obtained from the transmit aperture Tx in an initial transmission event is set.

Next, the identification number 1 of the partial transducer array 101a_1 is set to 1 (step S215).

Next, the processing proceeds to observation point synchronized beamforming processing (step S220 (S221 to S228)). In step S220, a coordinate ij indicating the position of the observation point Pij is initialized to the minimum value on the target line group Bx (steps S221 and S222). Subsequently, the receive aperture setting unit 4113 selects the receive aperture Rx transducer array such that an array center matches the transducer Xk spatially closest to the observation point Pij (step S223). With this operation, the part delay-and-sum part 411_1 performs, in the subsequent beamforming processing (step S220) delay-and-sum processing using a reception signal sequence rf based on the reflected wave received by the transducer included in the range overlapping with the receive aperture Rx transducer array among the partial transducer array 101a_1 from the subject, as an input signal.

Next, the beamforming processing (step S220) is performed to generate an acoustic line signal for the observation point Pij (step S224).

Figure 18:
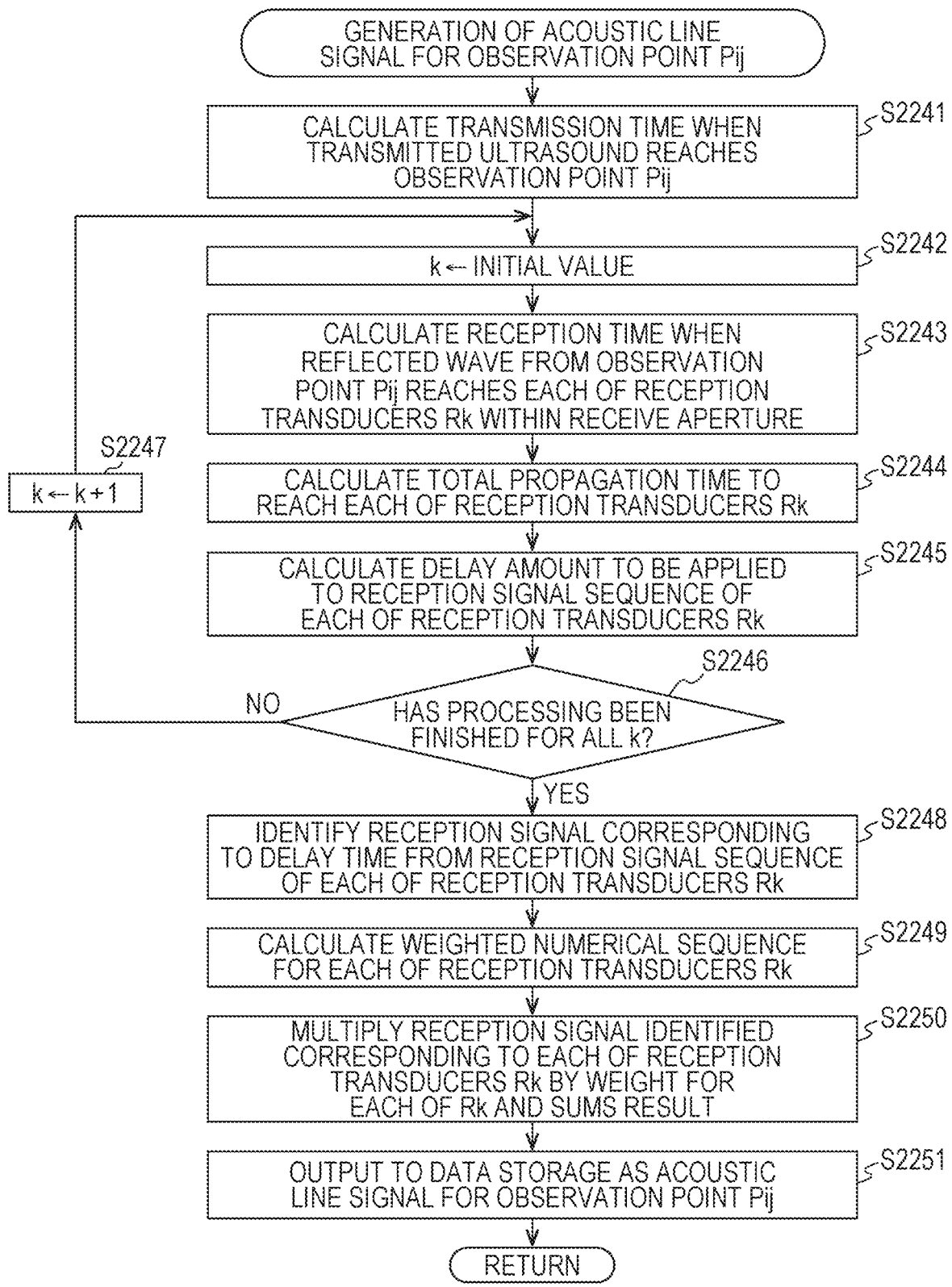
FIG. 18 is a flowchart illustrating details of step S224 in FIG. 17A.
Figure 19:
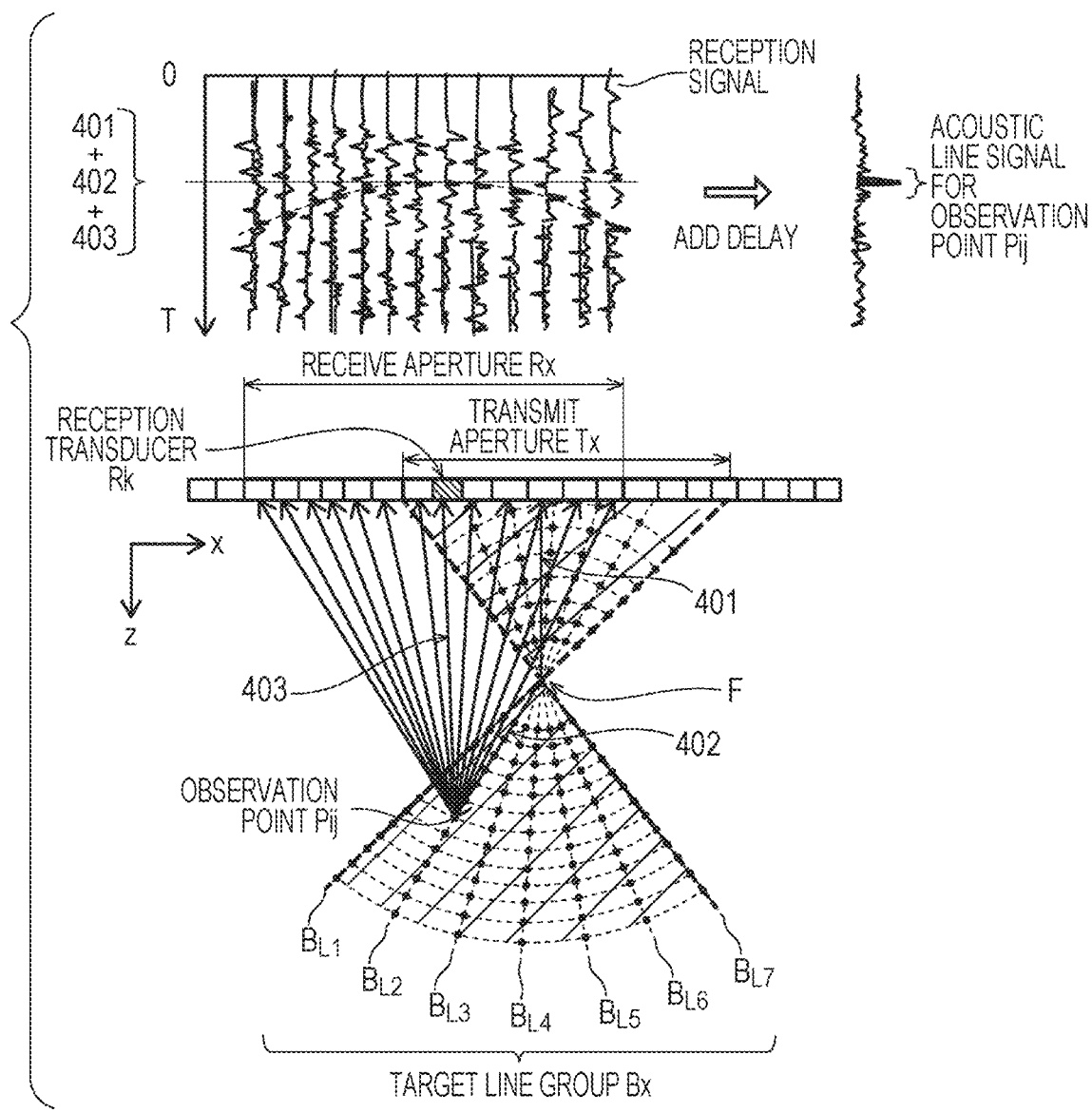
FIG. 19 is a schematic diagram illustrating acoustic line signal generating operation on an observation point Pij.

Now, operation of generating the acoustic line signal for the observation point Pij in step S224 will be described. FIG. 18 is a flowchart illustrating the details of step S224 in FIG. 17A, and illustrates acoustic line signal generating operation on the observation point Pij in the receive beamformer unit 104. FIG. 19 is a schematic diagram illustrating the acoustic line signal generating operation on the observation point Pij in the receive beamformer unit 104.

First, in step S2241, the transmission time calculation unit 4114 calculates a transmission time when the transmitted ultrasound wave reaches the observation point Pij in the subject, for an arbitrary observation point Pij present on the target line group Bx. The transmission time can be calculated as follows. (1) In a case where the depth of the observation point Pij is the focal depth or more, it is calculated by dividing a length of a path (401+402) from the reception transducer Rk in the receive aperture Rx geometrically determined to the observation point Pij via the transmission focal point F by a sound speed cs of the ultrasound wave. (2) In a case where the observation point Pij is less deep than the focal depth, it is calculated by dividing a length of a difference (401−402) between a path from the reception transducer Rk within the receive aperture Rx to the transmission focal point F and a path from the observation point Pij to the focal point by the sound speed cs of the ultrasound wave.

Next, a coordinate k indicating the position of the reception transducer Rk in the receive aperture Rx obtained from the receive aperture Rx is initialized to a minimum value in the receive aperture Rx (step S2242). Subsequently, the reception time calculation unit 4115 calculates a reception time when the ultrasound wave transmitted and reflected by the observation point Pij in the subject reaches the reception transducer Rk of the receive aperture Rx (step S2243). The reception time can be calculated by dividing the length of the geometrically determined path 403 from the observation point Pij to the reception transducer Rk by the sound speed cs of the ultrasound wave. Furthermore, the delay amount calculation unit 4116 calculates from the sum of the transmission time and the reception time the total propagation time until the ultrasound wave transmitted from the transmit aperture Tx and reflected by the observation point Pij reaches the reception transducer Rk (Step S2244) and calculates the delay amount for each of the reception transducers Rk by the difference in the total propagation time for each of the reception transducers Rk within the receive aperture Rx (step S2245).

It is determined whether the delay amount calculation has been completed for all the reception transducers Rk present in the receive aperture Rx (step S2246). In a case where it is not completed, the coordinate k is incremented (step S2247) to continue the delay amount calculation for the reception transducer Rk (step S2243). In a case where the calculation is completed, the processing proceeds to step S2248. At this stage, the delay amount in reflected wave arrival from the observation point Pij has been calculated for all of the reception transducers Rk present in the receive aperture Rx.

In step S2248, the delay processing unit 4117 subsequently identifies the reception signal corresponding to the time obtained by subtracting the delay amount for each of the reception transducers Rk from the reception signal sequence corresponding to each of the reception transducers Rk within the receive aperture Rx as the reception signal based on the reflected wave from the observation point Pij.

Next, the weight calculation unit 4118 calculates a weighted numerical sequence for each of the reception transducers Rk so as to maximize the weight for the transducer positioned at the center in the array direction of the receive aperture Rx (step S2249). The summing part 4119 multiplies the reception signal identified corresponding to each of the reception transducers Rk by the weight for each of the reception transducers Rk and sums the result to generate an acoustic line signal for the observation point Pij (step S2250). The acoustic line signal generated for the observation point Pij, is output to and stored in the data storage 107 (step S2251).

Next, returning to FIG. 17, the coordinates i, j are incremented to repeat step S224 so as to generate acoustic line signals for all the observation points Pij (marked with filled circles "●" in FIG. 19) located at the coordinates ij on the target line group Bx. It is determined whether generation of acoustic line signals has been completed for all the observation points Pij present on the target line group Bx (steps S225 and S227). In a case where it is not completed, the coordinate ij is incremented (step S226 and S228) to generate an acoustic line signal for the observation point Pij (step S224). In a case where it is completed, the processing proceeds to step S228. At this stage, acoustic line signal partial subframe data ds_1 for all observation points Pij present on the target line group Bx accompanying one transmission event has been generated, output to and stored in the data storage 107.

Figure 20:
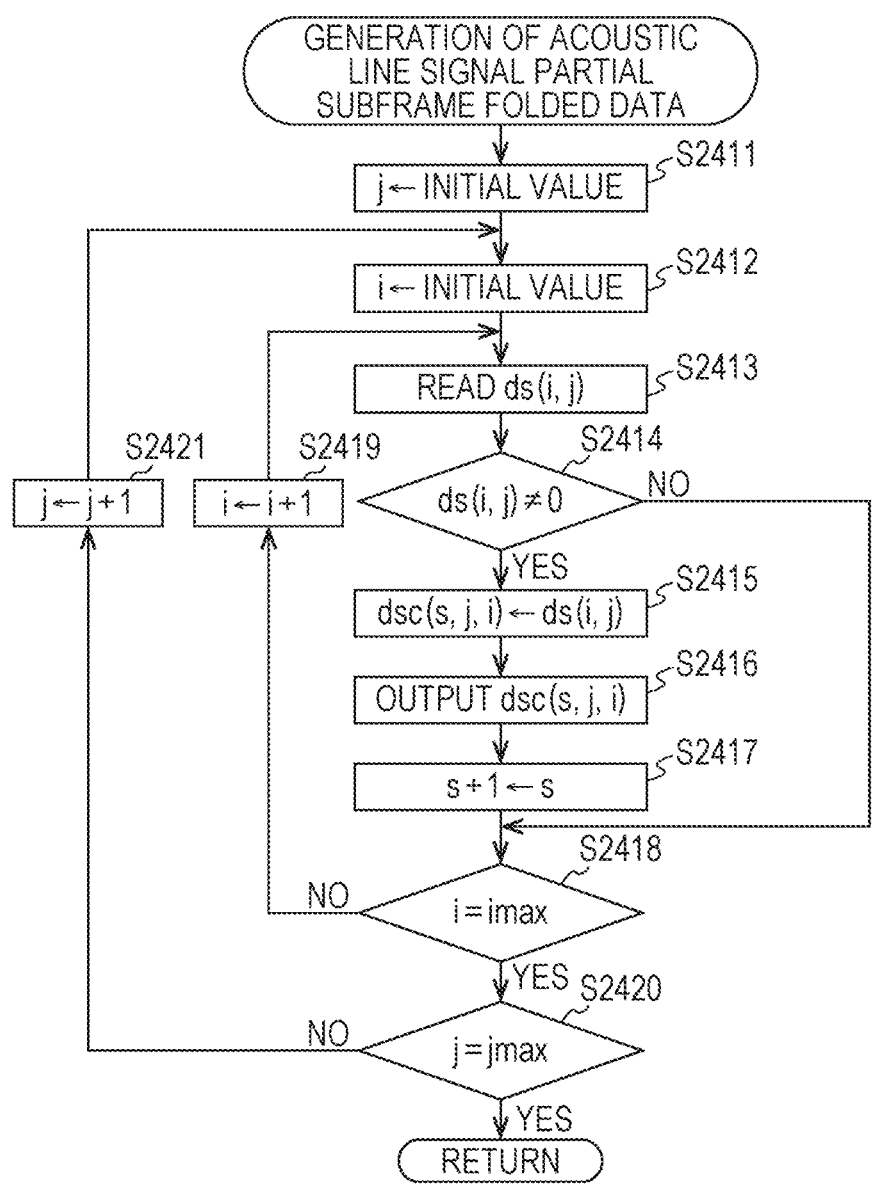
FIG. 20 is a flowchart illustrating details of step S240 in FIG. 17B.

Next, the part folding part 412_1 performs acoustic line signal partial subframe folded data generation processing (step S250). FIG. 20 is a flowchart illustrating details of step S240 in FIG. 17B.

Values j and j indicating the position of the on-line observation point PBxij on the target line group Bx are initialized to the minimum value (steps S2411, S2412), and the on-line observation point acoustic line signal extraction unit 4121 reads the signal ds (i, j) located at the coordinates (j, j) on the acoustic line signal partial subframe data ds_1 from the data storage 107 (step S2413), and judges whether ds (i, j) is a fixed value ds0(0) indicating zero (step S2414). In a case where it is the fixed value ds0 (0) (No in step S2414), the processing proceeds to step S2418. In a case where ds (i, j) is not the fixed value ds0 (0) (Yes in step S2414), ds (i, j) is determined to be the acoustic line signal ds (i, j) at the on-line observation point PBxij on the target line group Bx, j), and the acoustic line signal ds (i, j) is replaced by the acoustic line signal dsc (s, j, i) obtained by adding the identification number s for identifying the target line BL in the target line group Bx to the acoustic line signal ds (i, j) (step S2415) and outputs the signal to the data storage 107 (step S2416), and increments the identification number s (step S2417).

Next, it is determined whether the processing has been completed for all i among j and j indicating the position (step S2418), and it is determined whether processing has been completed for all j in the ultrasound main irradiation region Ax (step S2420). In a case where the processing is not completed, i and j are incremented (steps S2419 and S2421), and then, it is determined whether ds (i, j) is a fixed value ds0 (0) (step S2414). In a case where the processing has been completed for all i and j, the processing proceeds to step S250 in FIG. 17B.

At this stage, with respect to the iteration concerning the partial transducer array 101a-1, all the acoustic line signals ds (i, j) at the on-line observation point PBxij on the target line group Bx included in the ultrasound main irradiation region Ax have been extracted in a state of being replaced by the acoustic line signals dsc (s, j, i). With this operation, the acoustic line signal partial subframe folded data dsc_1 related to the partial transducer array 101a_1 is generated. As described in FIGS. 12C and 12D, the acoustic line signal partial subframe folded data dsc_1 is a sequence of the acoustic line signal ds (i, j) for the on-line observation point PBxij, having reduced intervals between the target lines BL, making it possible to reduce the data amount, enabling downscaling of necessary internal memory capacity and data transmission capability.

Next, it is determined whether generation of acoustic line signal partial subframe data ds_1 has been completed for all the partial transducer arrays 101a_1 (step S250). In a case where it is not completed, 1 is incremented (step S251) and the processing returns to step S221. In a case where it is completed, the processing proceeds to step S260.

At this stage, acoustic line signal partial subframe folded data dsc_1 is generated for all the partial transducer arrays 101a_1 accompanying one transmission event, and output to and stored in the data storage 107.

Next, the main summing part 413 reads the acoustic line signal partial subframe folded data dsc_1 corresponding to each of the plurality of partial transducer arrays 101a_1 from the data storage 107, and sums these on the basis of the position of the observation point on the orthogonal coordinate (s, j) having an absolute value of the identification number s and the depth (z) as two axes so as to generate acoustic line signal subframe folded data dsc (step S260).

Figure 21:
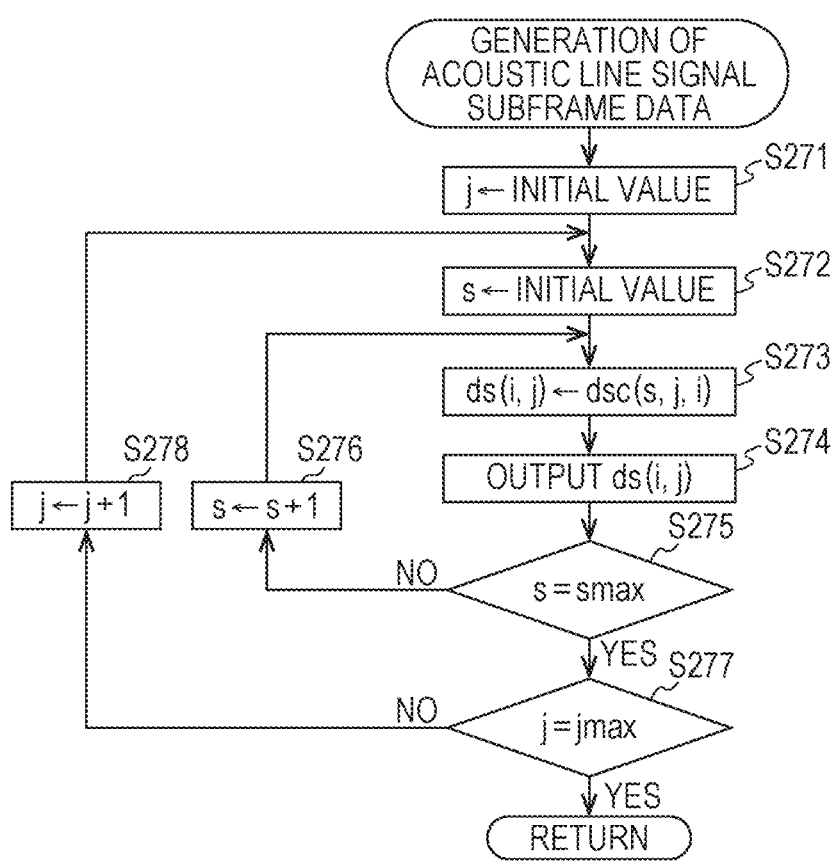
FIG. 21 is a flowchart illustrating details of step S270 in FIG. 17B.

Subsequently, the re-sequence part 414 re-sequences the acoustic line signal dsc (s, j, i) in the acoustic line signal subframe folded data dsc_sf onto the position of the on-line observation point PBxij in the ultrasound main irradiation region Ax to generate acoustic line signal subframe data ds_sf (step S270). FIG. 21 is a flowchart illustrating details of step S270 in FIG. 17B.

j and j indicating the position on the on-line observation point PBxij on the target line group Bx are initialized to the minimum value (steps S271 and S272). The re-sequence part 414 reads the acoustic line signal dsc (s, j, i) located on the coordinate (s, j) on the acoustic line signal subframe folded data dsc_sf from the data storage 107 and replaces the acoustic line signal dsc (s, j, i) to which the identification number s to identify the target line BL is added, by the acoustic line signal ds (i, j) (step S273), and outputs the signal in the data storage 107 (step S274). At this time, the re-sequence part 414 re-sequences the acoustic line signal dsc (s, j, i) to the position of the on-line observation point PBxij on the orthogonal coordinate (i, j), while interpolating the fixed value ds0 indicating zero to the portions other than the observation point PBxij.

Next, it is determined whether the processing has been completed for all s among identification number s and j indicating the position (step S275), and it is determined whether processing has been completed for all j in the ultrasound main irradiation region Ax (step S277). In a case where the processing is not completed, s and j are incremented (steps S276 and S277), and then, the acoustic line signal dsc (s, j, i) is replaced by the acoustic line signal ds (i, j) (step S273). In a case where the processing has been completed for all s and j, the processing proceeds to step S290 in FIG. 17B.

At this stage, the re-sequence part 414 uses the acoustic line signal subframe folded data dsc_sf as an input to generate the acoustic line signal subframe data ds_sf for the iteration related to the partial transducer array 101a_1.

Next, returning to FIG. 17, it is determined whether generation of the acoustic line signal subframe data ds_sf has been completed for all the transmission events (step S290). In a case where it is not completed, the processing returns to step S210, and the coordinate ij indicating the position of the observation point Pij is initialized to the minimum value on the target line group Bx obtained from the transmit aperture Tx at the subsequent transmission event (steps S221 and S222) and then, the receive aperture Rx is set (step S223). In a case where it is completed, the processing proceeds to step S301.

Next, in step S301, the summing processing unit 421 reads the plurality of pieces of acoustic line signal subframe data ds_sf held in the data storage 107 and sums a plurality of pieces of acoustic line signal subframe data ds_sf with the position of the observation point Pij as an index to generate a combined acoustic line signal for each of the observation points Pij to be combined as the acoustic line signal frame data ds_f. Next, the amplification processing unit 422 multiplies each of the combined acoustic line signals by an amplification factor determined in accordance with the number of times of summing of each of the combined acoustic line signals included in the acoustic line signal frame data ds_f (step S302), and outputs the amplified acoustic line signal frame data ds_f to the ultrasound image generator 105 and the data storage 107 (step S303), and the processing is finished.

5. Image Quality Evaluation

Image quality evaluation of a generated B-mode image was performed using an example in which the receive beamformer unit 104 according to the embodiment is applied and using a comparative example.

(1) Test Sample

Figure 22C:
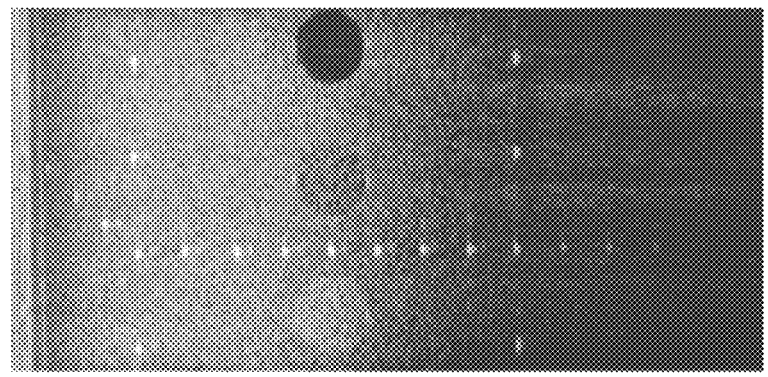
FIGS. 22A to 22C are ultrasound images obtained by receive beamforming of the example and comparative example 1.
Figure 22B:
Figure 22A:
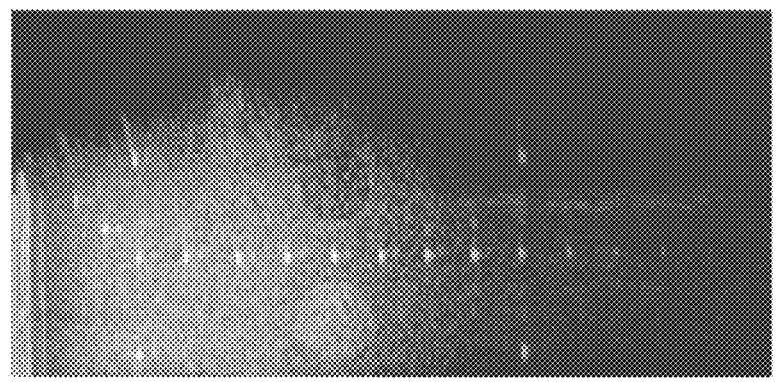

FIGS. 22A to 22C are ultrasound images obtained by receive beamforming of an example and comparative example 1. Specific sample specifications are as follows.

i) FIG. 22A

B-mode image based on the acoustic line signal partial subframe data ds_1 generated by the part delay-and-sum part 411_1, where the division number n of the partial transducer array 101a_1 is set to 2.

ii) FIG. 22B

B-mode image based on the acoustic line signal partial subframe data ds_2 generated by the part delay-and-sum part 411_2.

iii) FIG. 22C

This is a B-mode image based on the acoustic line signal subframe data ds_sf obtained by arithmetically summing the acoustic line signal partial subframe data ds_1 and acoustic line signal partial subframe data ds_2.

(2) Evaluation Result

An image is drawn in the left half in FIG. 22A, an image is drawn in the right half in FIG. 22B, and an image of good quality is drawn in FIG. 22C.

6. Effect of Receive Beamformer Unit 104

A configuration and function of the ultrasound diagnostic apparatus 100 according to examples according to the present embodiment, mainly of the receive beamformer unit 104, will be described. Note that the same configuration as that used for known ultrasound diagnostic apparatuses can be applied to the configuration other than the receive beamformer unit 104.

Example 1

Figure 23:
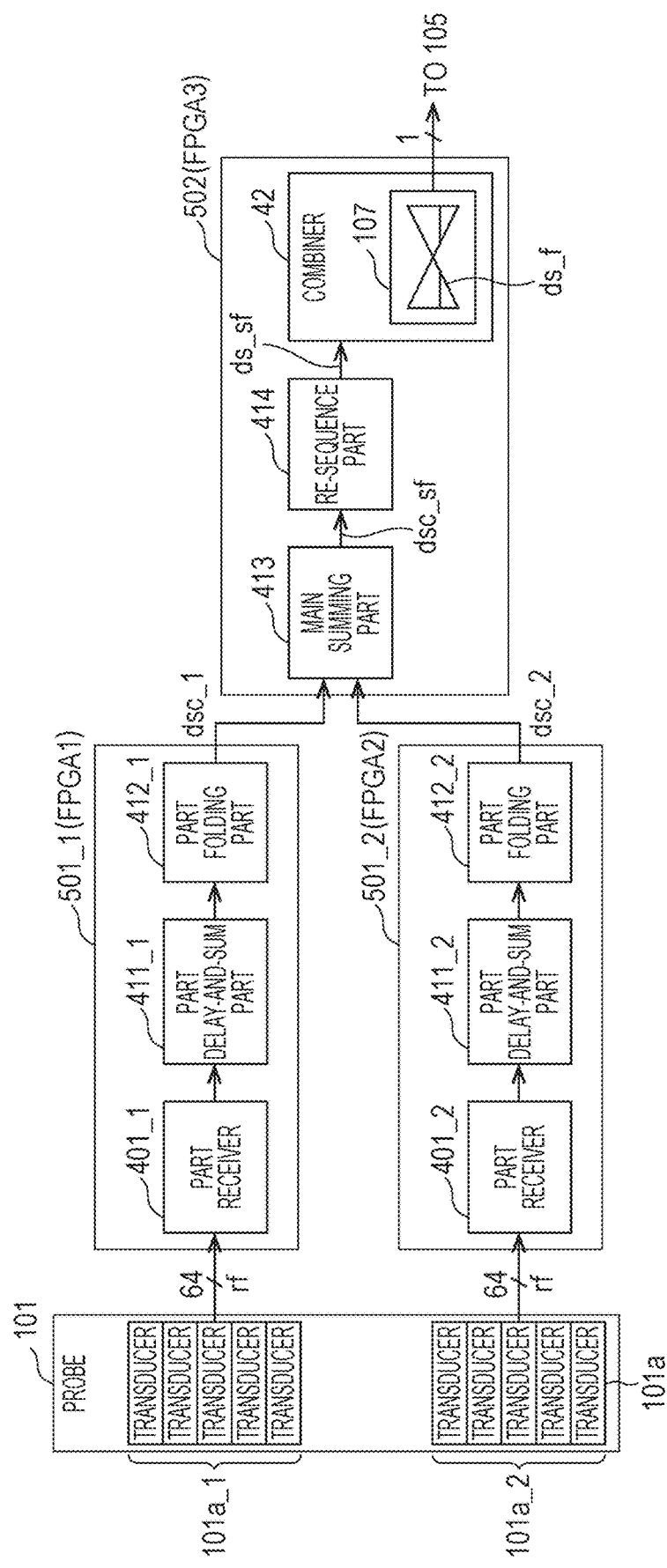
FIG. 23 is a schematic mounting view of the receive beamformer unit in the ultrasound diagnostic apparatus according to the embodiment.

FIG. 23 is a schematic mounting view of the receive beamformer unit 104 in an ultrasound diagnostic apparatus 100A according to an example of the present embodiment. The following is functional arrangement in the receiver 40, the delay-and-sum part 41, and the combiner 42 implemented in each of the plurality of integrated circuits constituting the receive beamformer unit 104 when the division number n of the partial transducer array 101a_1 is 2. As illustrated in FIG. 23, the ultrasound diagnostic apparatus 100A includes the partial transducer arrays 101a_1 and 101a_2 obtained by dividing the transmission transducer 101a array formed with 128 transducers into n (n=2), each including integrated circuits 501_1 and 501_2 connected to 64 transducers (64 channels), and an integrated circuit 501_3. Each of the plurality of part receivers 401_1 and 401_2, each of the plurality of part delay-and-sum parts 411_1 and 411_2, and each of the plurality of part folding parts 412_1 and 412_2 are included in each of the two integrated circuits 501_1 and 501_2, respectively. The main summing part 413 and the re-sequence part 414 are included in the integrated circuit 501_3. In this configuration, the acoustic line signal partial subframe folded data dsc_1 is transmitted from each of the two integrated circuits 501_1 and 501_2 to the integrated circuit 501_3. Furthermore, the ultrasound diagnostic apparatus 100A may be configured to include the combiner 42 in the integrated circuit 501_3.

As described above, the acoustic line signal partial subframe folded data dsc_1 is a sequence of the acoustic line signal ds (i, j) for the on-line observation point PBxij with reduced intervals between the target lines BL, making it possible to downscale the data amount to a range of 20% to 80% (in the above example, data amount is downscaled to $5/13$ (approximately 38.5%), compared with the acoustic line signal partial subframe data ds_1. In data transfer from the integrated circuits 501_1 and 501_2 to the integrated circuit 501_3, the data transfer is performed after the acoustic line signal partial subframe data ds_1 is converted to the acoustic line signal partial subframe folded data dsc_1 by the part folding parts 412_1 and 412_2, making it possible to downscale the data amount related to the transfer. This makes it possible to suppress the necessary internal memory capacity of the integrated circuits 501_1, 501_2, and 501_3 and the necessary data transmission capability between the integrated circuits 501_1 and 501_2 to the integrated circuit 501_3.

Moreover, the array of the reception transducer 101a is divided into n, and the delay-and-sum processing related to the reception transducer 101a is distributed to the plurality of integrated circuits 501_1, 501_2, and 501_3. This makes it possible to reduce the computation amount per arithmetic unit by distributing the delay-and-sum processing to a plurality of arithmetic units. With this configuration, it is possible to construct the hardware by employing a plurality of small-scale field programmable gate arrays (FPGAs) in each of the integrated circuits 501_1 and 501_2 performing the delay-and-sum processing and the folding processing as preceding-stage processing corresponding to each of the partial transducer arrays and in the integrated circuit 501_3 performing the main summing processing, rearrangement processing, the re-sequence processing, and the combining processing as succeeding-stage processing. This makes it possible to drastically reduce the cost of arithmetic units in hardware.

The combiner 42 is a circuit that obtains the acoustic line signal subframe data ds_sf generated in synchronization with the transmission event from the re-sequence part 414 to be combined into the acoustic line signal frame data ds_f, and outputs the frame data to the data storage 107. The ultrasound diagnostic apparatus 100A has a configuration in which the integrated circuit 501_3 includes the data storage 107 as an internal memory. The data storage 107 (internal memory) stores the acoustic line signal frame data ds_f combined in synchronization with the previous transmission event. The combiner 42 obtains new acoustic line signal subframe data ds_sf from the re-sequence part 414 for each of transmission events to be combined into a new acoustic line signal frame data ds_f and updates the acoustic line signal frame data ds_f stored in the data storage 107 to the newly created data. At the same time, the combiner 42 outputs the acoustic line signal ds corresponding to the difference between the acoustic line signal frame data ds_f created at the previous transmission event and the acoustic line signal frame data ds_f created at the current transmission event, to the ultrasound image generator 105. The acoustic line signal ds corresponding to the difference between transmission events is a sequence of the acoustic line signals ds extended in the depth direction corresponding to the width of one transducer 101a, being the data amount obtained by dividing the data amount of the acoustic line signal frame data ds_f by the number of transmission events. In this example, when the number of transmission events is defined as the total number 128 of transducers 10a, the data amount is 1/128 of the data amount of the acoustic line signal frame data ds_f.

With this configuration, the data to be transferred from the integrated circuit 501_3 for each of the transmission events can be reduced to the acoustic line signal ds corresponding to the difference between the transmission events out of the acoustic line signal frame data ds_f, making it possible to downscale the data transmission capability needed for data transmission to the succeeding stage of the integrated circuit 501_3.

Example 2

Figure 24:
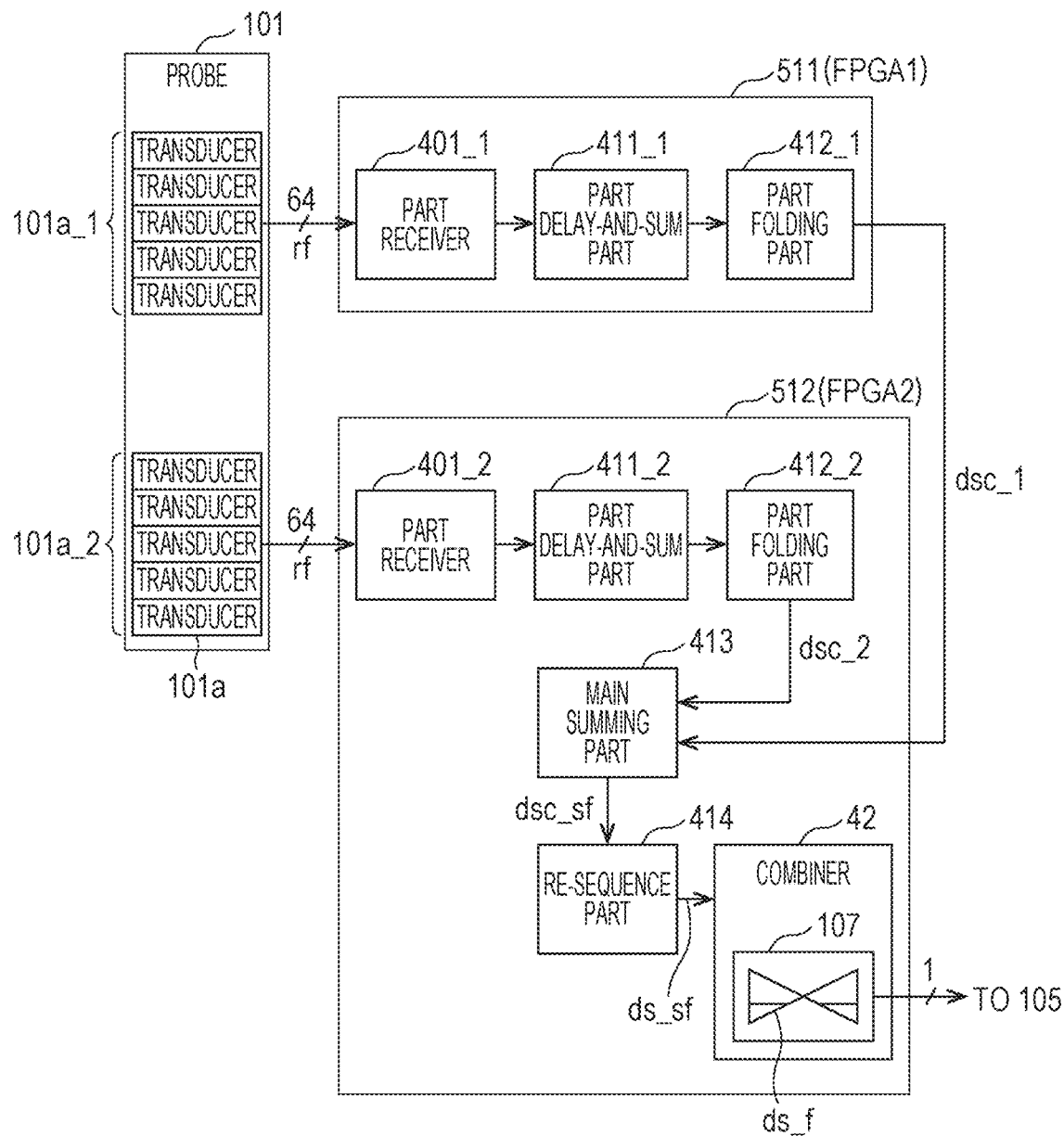
FIG. 24 is a schematic mounting view of the receive beamformer unit in an ultrasound diagnostic apparatus according to another example.

FIG. 24 is a schematic mounting view of the receive beamformer unit 104 in an ultrasound diagnostic apparatus 100B according to another example of the present embodiment. Again, the division number n of the partial transducer array 101a_1 is 2. As illustrated in FIG. 24, the ultrasound diagnostic apparatus 100B has the following configuration. The partial transducer arrays 101a_1 and 101a_2 obtained by dividing the array of the reception transducer 101a into n (n=2) includes n integrated circuits 511 and 512. Each of the plurality of part receivers 401_1 and 401_2, each of the plurality of part delay-and-sum parts 411_1 and 411_2, and each of the plurality of part folding parts 412_1 and 412_2 are included in each of the n integrated circuits 511 and 512, respectively. The summing part 413 and the re-sequence part 414 are included in any of the n integrated circuits 511 and 512. The acoustic line signal partial subframe folded data dsc_1 is transmitted to the integrated circuit including the main summing part 413 and the re-sequence part 414 from each of the other integrated circuits. Furthermore, the ultrasound diagnostic apparatus 100B may be configured to include the combiner 42 in the integrated circuit including the main summing part 413 and the re-sequence part 414.

With the ultrasound diagnostic apparatus 100B, the following effects can be further obtained in addition to the effects indicated by the above-described ultrasound diagnostic apparatus 100A. The ultrasound diagnostic apparatus 100A has a configuration of dividing an array of a plurality of transducers arranged in an ultrasound probe into a plurality of partial transducer arrays, performing delay-and-sum processing and folding processing at a preceding stage on the basis of a reception signal obtained for each of the partial transducer arrays, and performing main summing processing, re-sequence processing, and combining processing on combining acoustic line signals generated from each of the delay-and-sum processing, at a succeeding stage. Among them, the main summing processing, the re-sequence processing, and the combining processing performed at the succeeding stage in the integrated circuit 501_3 need a smaller computation amount than the delay-and-sum processing and the folding processing performed at the preceding stage in the integrated circuits 501_1 and 501_2, and may be performed by any of the integrated circuits 501_1 and 501_2. The ultrasound diagnostic apparatus 100B is configured in such a way that the main summing processing, re-sequence processing, and the combining processing of the succeeding stage are performed by one of the integrated circuits 511 and 512 that perform the delay-and-sum processing and the folding processing of the preceding stage. With this configuration, the ultrasound diagnostic apparatus 100B can eliminate the integrated circuits 501_3, making it possible to further reduce the cost of the arithmetic unit in the hardware.

While, for the sake of simplicity, FIG. 24 illustrates an exemplary case where the transducer array (101a) is divided into two partial transducer arrays 101a_1 and 10a_2, and the delay-and-sum part 41 is formed with two part delay-and-sum parts 411_1 and 411_2, the division number n is of course not limited to 2.

7. Modification

While the ultrasound signal processing apparatus according to the embodiments has been described above, the present invention is not limited to the above embodiment at all, except for substantial characteristic constituents of the apparatus. For example, other embodiments implemented by those skilled in the art by applying various modifications to the embodiment and combining any constituent elements and functions according to the embodiment without departing from the scope and spirit of this invention are included in the present invention. Hereinafter, as an example of such embodiments, an ultrasound signal processing apparatus according to a modification will be described.

(1) The ultrasound diagnostic apparatus 100 according to the first embodiment has a configuration in which the receive aperture setting unit 4113 selects the receive aperture Rx such that the array center matches the transducer spatially closest to the on-line observation point PBxij. Alternatively, the configuration of the receive aperture Rx can be modified as appropriate.

A first modification differs from the first embodiment in that there is provided a transmission synchronous receive aperture setting unit (hereinafter referred to as a "Tx receive aperture setting unit") that selects a receive aperture Rx transducer array in which the array center matches the array center of the transmit aperture Tx transducer array. The configuration other than the Tx receive aperture setting unit is the same as individual elements illustrated in the first embodiment, and thus, the description of the same portions will be omitted.

Figure 25:
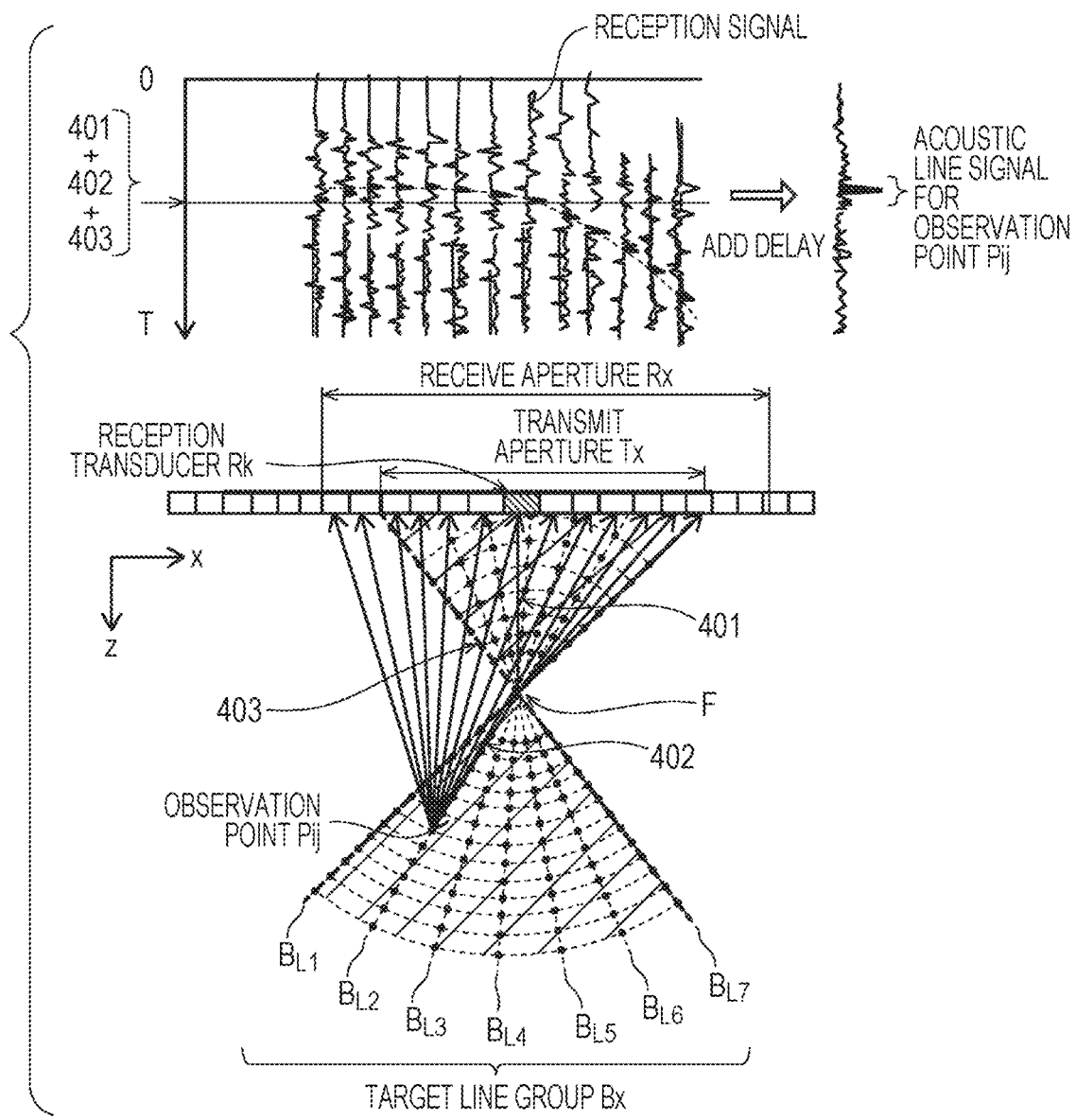
FIG. 25 is a schematic diagram illustrating acoustic line signal generating operation on the observation point Pij in the receive beamformer unit according to a comparative example.

FIG. 25 is a schematic diagram illustrating a relationship between the receive aperture Rx and the transmit aperture Tx set by the Tx receive aperture setting unit. In the first modification, the receive aperture Rx transducer array is selected such that the array center of the receive aperture Rx transducer array matches the array center of the transmit aperture Tx transducer array. The position of the central axis of the receive aperture Rx is the same as the position of the central axis of the transmit aperture Tx, and the receive aperture Rx is an aperture symmetric about the transmission focal point F Accordingly, the position of the receive aperture Rx also moves in synchronization with the position change of the transmit aperture Tx moving in the array direction for each of transmission events.

The weighted numerical sequence (reception apodization) for each of the reception transducers Rk of the receive aperture Rx is calculated so as to maximize the weight for the transducer located on the central axis of the receive aperture Rx and the central axis of the transmit aperture Tx. The weighted numerical sequence has a symmetric distribution around the transducer Xk. The shape of the distribution of the weighted numerical sequence may be a hamming window, a hanning window, a rectangular window or the like, and the shape of the distribution is not particularly limited.

In the ultrasound diagnostic apparatus according to the first modification, the following effects can be obtained, instead of the effects except for the observation point synchronous type receive aperture, among the effects described in the first embodiment. That is, in the first modification, the Tx receive aperture setting unit selects the transducer array having the array center matching the array center of the transducer array included in the transmit aperture Tx corresponding to the transmission event, as the reception transducer to set the receive aperture Rx. Accordingly, the position of the central axis of the receive aperture Rx is the same as the position of the central axis of the transmit aperture Tx, and the position of the receive aperture Rx also changes (moves) in synchronization with the position change of the transmit aperture Tx moving in the array direction for each of transmission events. This makes it possible to perform the delay-and-sum at mutually different receive apertures in synchronization with each of transmission events, and while the reception time points mutually differ over the plurality of transmission events, enabling acquisition of an effect of the reception processing using a wider receive aperture, and acquisition of uniform spatial resolution in a wide observation region.

(2) While the embodiment is a case where the target line group Bx has arranged seven target lines at equal angles, the number of target lines of the target line group Bx may be three or more. The positional relationship of the target line is not limited to the case where the two adjacent target lines form a fixed angle. For example, it is possible to set the intervals between the observation points on the target line to be equal at a same depth. Here, a straight line L is a straight line parallel to the direction in which the transducers are arranged, and the interval of the intersections of the straight line L and each of the target lines is fixed.

Note that the target line group Bx is not limited to the above-described example and may have any form as long as: the target line group Bx includes a plurality of target lines passing through the transmission focal point F; and the distance between two observation points located on two adjacent target lines and present at equal distances from the focal point F or at the same depth is longer than the distance between two adjacent observation points on a same target line. Still, as described above, since it is preferable that the directions of the target lines are not similar to each other, it is preferable to be uniform in angles or in the direction in which the transducers are arranged. Moreover, it is preferable to obtain the maximum value of the angle formed by the two target lines, and it is preferable that the two target lines match the outline of the ultrasound main irradiation region Ax. Moreover, it is preferable that one target line is on the transmit aperture central axis. This is because an acoustic line signal having the highest signal intensity can be obtained.

(3) The ultrasound diagnostic apparatus 100 according to the present embodiment is not limited to the ultrasound diagnostic apparatus having the configuration illustrated in FIG. 1. For example, there is no need to provide the multiplexer unit 102, and the transmit beamformer unit 103 and the receive beamformer unit 104 may be directly connected to each of the transducers 101a of the probe 101. Moreover, all or portion of the transmit beamformer unit 103, the receive beamformer unit 104, etc. may be incorporated in the probe 101. This also applies to other ultrasound diagnostic apparatuses according to other embodiments and modifications described below in addition to the ultrasound diagnostic apparatus 100 according to the present embodiment.

(4) While the present disclosure has been described on the basis of the above embodiments, the present invention is not limited to the above embodiments, and the following cases are also included in the present invention.

For example, the present invention may be a computer system including a microprocessor and a memory, in which the memory stores a computer program, and the microprocessor operates in accordance with the computer program. For example, the present invention may be a computer system having a computer program of a diagnostic method of the ultrasound diagnostic apparatus of the present invention and configured to operate in accordance with the program (or directing operation to connected parts).

Moreover, cases where the whole or a part of the ultrasound diagnostic apparatus, or the whole or a part of functions of beamforming is implemented by a computer system including a recording medium such as a microprocessor, a ROM, a RAM, a hard disk unit, are also included in the present invention. The RAM or the hard disk unit stores a computer program capable of achieving operation similar to the operation of each of the above-described apparatus. When the microprocessor operates according to the computer program, functions of the apparatus are implemented.

A portion or all of the constituents of each of the above apparatuses may be constituted by one system large scale integration (LSI). The system LSI is a super multifunctional LSI manufactured by integrating a plurality of constituent parts on one chip, specifically, it is a computer system including a microprocessor, a ROM, a RAM. These may be separately formed into one chip, or may be integrated into one chip so as to include some or all of them. Note that the LSI may be referred to as an IC, a system LSI, a super LSI, or an ultra LSI depending on the degree of integration. The RAM stores a computer program capable of achieving operation similar to the operation of each of the above-described apparatus. When the microprocessor operates according to the computer program, functions of the system LSI are implemented. For example, the present invention includes a case where the beamforming method of the present invention is stored as a program of the LSI, and this LSI is inserted in the computer to execute the predetermined program (beamforming method).

Note that the method of circuit integration is not limited to LSI, and may be implemented by a dedicated circuit or a general-purpose processor. It is allowable to employ a field programmable gate array (FPGA) that can be programmed after LSI fabrication, and a reconfigurable processor capable of reconfiguring connection and setting of circuit cells inside the LSI.

Furthermore, in a case where an integrated circuit technology to replace the LSI emerges with advances in semiconductor technology or another derivative technology, functional block integration may of course be performed using the technology.

In addition, part or all of the functions of the ultrasound diagnostic apparatus according to each of the embodiments may be implemented by execution of a program by a processor such as a CPU. The present invention may be a non-transitory computer readable recording medium storing a program for implementing a diagnostic method or the beamforming method of the above-described ultrasound diagnostic apparatus. Programs and signals may be recorded on a recording medium and transported to allow the program to be executed by another independent computer system, and the program may of course be distributed via a transmission medium such as the Internet.

Each of constituents of the ultrasound diagnostic apparatus according to the above embodiment may be implemented by a programmable device such as a central processing unit (CPU), a graphics processing unit (GPU), and a processor, together with software. The latter configuration is also referred to as a general-purpose computing on graphics processing unit (GPGPU). These constituents can be formed with a single circuit component or an aggregate of a plurality of circuit components. In addition, a plurality of constituents can be combined into a single circuit component, or a plurality of circuit components as an aggregate.

While the ultrasound diagnostic apparatus according to the above-described embodiment has a configuration in which the ultrasound diagnostic apparatus includes a data storage as a storage device, the storage apparatus is not limited to this configuration, and may be configured to allow a semiconductor memory, a hard disk drive, an optical disk drive, a magnetic storage device, or the like, to be externally connected to the ultrasound diagnostic apparatus.

The division of functional blocks in the block diagram is illustrative, and it is allowable to configure such that a plurality of functional blocks serves as one functional block, one functional block is divided into a plurality of blocks, or some functions are transferred to another functional block. In addition, it is allowable to cause a single hardware or software unit to process functions of a plurality of functional blocks having similar functions in parallel or in time division.

Moreover, the execution order of the above-described steps is given as an example to specifically illustrate the present invention, and the order may be another order other than the example described above. In addition, a portion of the above-described steps may be executed simultaneously (in parallel) with other steps.

Moreover, while the ultrasound diagnostic apparatus has a configuration to be externally connected with the probe and the display unit, the probe and the display unit may be integrally provided in the ultrasound diagnostic apparatus.

The probe may include a portion of the functions of the transmitter/receiver in the probe. For example, the probe may generate inside the probe a transmission electric signal on the basis of a control signal to generate a transmission electric signal, output from the transmitter/receiver and may convert the transmission electric signal into an ultrasound wave. In addition, it is possible to adopt a configuration of converting the received reflected ultrasound wave into a reception electric signal, and generating a reception signal inside the probe on the basis of the received electric signal.

In addition, at least a portion of the functions of the ultrasound diagnostic apparatus according to individual embodiments and modifications may be combined with each other. Furthermore, the numbers used above are all examples for specifically illustrating the present invention, and the present invention is not limited to the exemplified numbers.

Moreover, the present invention includes various modifications to the present embodiment, obtained by modifying the embodiment within the scope conceivable by those skilled in the art.

<<Summing-Up>>

An ultrasound diagnostic apparatus according to an embodiment is an ultrasound diagnostic apparatus that transmits an ultrasound beam to a subject using an ultrasound probe including a plurality of transducers and generates acoustic line signal subframe data on the basis of a reflected wave obtained from the subject, the ultrasound signal processing apparatus including: a transmitter that sets a focal point defining a converging point of an ultrasound beam in the subject and causes a plurality of transmission transducer arrays selected from the plurality of transducers to transmit the ultrasound beam to converge at the converging point; a receiver that generates a reception signal sequence for each of the transducers of the ultrasound probe on the basis of the reflected wave received by the ultrasound probe from the subject; and a delay-and-sum part that performs delay-and-sum operation on the reception signal sequence based on the reflected wave obtained within an ultrasound beam main irradiation region to generate acoustic line signal subframe data for a plurality of on-line observation points present in a target line group passing through the focal point among a plurality of intra-region observation points corresponding to the position within the main irradiation region, in which the receiver includes a plurality of part receivers that generates the reception signal sequence on the basis of the reflected wave received by each of the transducers included in a partial transducer array from the subject for each of a plurality of the partial transducer arrays obtained by dividing the transmission transducer array, the delay-and-sum part includes: a plurality of part delay-and-sum parts that performs delay-and-sum on the reception signal sequence corresponding to the plurality of partial transducer arrays to generate an acoustic line signal for the plurality of on-line observation points so as to generate acoustic line signal partial subframe data corresponding to each of the plurality of partial transducer arrays; a plurality of part folding parts that extracts an acoustic line signal sequence corresponding to the plurality of on-line observation points from the acoustic line signal partial subframe data corresponding to each of the plurality of partial transducer arrays, and that arranges the acoustic line signals with reduced intervals between the target lines included in the target line group so as to generate acoustic line signal partial subframe folded data; a main summing part that sums the acoustic line signal partial subframe folded data corresponding to each of the plurality of partial transducer arrays on the basis of the positions of the arranged observation points to generate acoustic line signal subframe folded data; and a re-sequence part that re-sequences the acoustic line signals in the acoustic line signal subframe folded data to the positions of the on-line observation points in the main irradiation region to generate the acoustic line signal subframe data.

With this configuration, it is possible to reduce the computation amount of the delay-and-sum and the data amount of the acoustic line signal to be generated while suppressing the degradation of the spatial resolution and the S/N ratio, leading to downscaling of the necessary internal memory capacity and data transmission capability in a receive beamformer of the ultrasound diagnostic apparatus.

In another aspect, it is allowable to have a configuration in any of the above-described aspects, in which each of the target lines included in the target line group is a straight line, and a distance between one observation point on one target line having a distance from the focal point being a predetermined distance or more and a closest observation point on the one target line is shorter than a distance between the one observation point and a closest observation point present on a target line adjacent to the one target line.

With such a configuration, it is possible to reduce the computation amount of the delay-and-sum and the data amount of the acoustic line signal to be generated while suppressing degradation in the spatial resolution and the S/N ratio.

In another aspect, it is allowable to have a configuration in any of the above-described aspects, further including a combiner that combines a plurality of pieces of the acoustic line signal subframe data to generate acoustic line signal frame data, in which the transmitter performs a transmission event of transmitting the ultrasound beam a plurality of times while changing the focal point, the receiver generates the reception signal sequence in synchronization with each of the transmission events, the delay-and-sum part generates a plurality of pieces of the acoustic line signal subframe data in synchronization with each of the transmission events, and the combiner combines the plurality of pieces of acoustic line signal subframe data generated in synchronization with each of the transmission events to generate a plurality of pieces of acoustic line signal frame data on the basis of a position of the observation point.

With this configuration, it is possible to suppress degradation in the spatial resolution and the S/N ratio by using the synthetic aperture method.

In another aspect, it is allowable to have a configuration in any of the above-described aspects, in which the partial transducer array is obtained by dividing the transmission transducer array into n, n first integrated circuits and second integrated circuits are provided, each of the plurality of part receivers, each of the plurality of part delay-and-sum parts, and each of the plurality of part folding parts are included in each of the n first integrated circuits, the main summing part and the re-sequence part are included in the second integrated circuit, and the acoustic line signal partial subframe folded data is transmitted from each of the n integrated circuits to the second integrated circuit.

With this configuration, in the data transfer of from the integrated circuits 501_1 and 501_2 to the integrated circuit 501_3, it is possible to downscale the data amount related to the transfer, and possible to suppress the necessary internal memory capacity of the integrated circuits 501_1, 501_2, and 501_3 and the necessary data transmission capability between the integrated circuits 501_1 and 501_2 to the integrated circuit 501_3.

Moreover, the line of the reception transducer 101a is divided into n, the delay-and-sum processing related to the reception transducer 101a is distributed to the plurality of integrated circuits 501_1, 501_2, and 501_3, the delay-and-sum processing is distributed to a plurality of arithmetic units It is possible to reduce the computation amount per arithmetic unit. With this configuration, it is possible to construct the hardware by employing a plurality of small-scale field programmable gate arrays (FPGAs) in each of the integrated circuits 501_1 and 501_2 performing the delay-and-sum processing and the folding processing as preceding-stage processing corresponding to each of the partial transducer arrays and in the integrated circuit 501_3 performing the main summing processing, rearrangement processing, the re-sequence processing, and the combining processing as succeeding-stage processing. This makes it possible to drastically reduce the cost of arithmetic units in hardware.

In another aspect, it is allowable to have a configuration in any of the above-described aspects, in which the partial transducer array is obtained by dividing the transmission transducer array into n, n integrated circuits are provided, each of the plurality of part receivers, each of the plurality of part delay-and-sum parts, and each of the plurality of part folding parts are included in each of the n integrated circuits, the main summing part and the re-sequence part are included in any of the n integrated circuits, and the acoustic line signal partial subframe folded data is transmitted to the integrated circuit including the main summing part and the re-sequence part from each of the other integrated circuits.

With this configuration, in the ultrasound diagnostic apparatus 100B, it is possible to reduce the number of integrated circuits, and it is possible to further reduce the cost of the arithmetic unit in the hardware.

In another aspect, it is allowable to have a configuration in any of the above-described aspects, further including a sequence determination part that determines sequence information to define a sequence method of the acoustic line signals on the target line in the acoustic line signal partial subframe folded data on the basis of various types of ultrasound measurement conditions, in which the part folding part sequences the acoustic signal sequences for each of the target lines to generate the acoustic line signal partial subframe folded data on the basis of the sequence information.

This configuration makes it possible to sequence the acoustic line signal sequences for each of the target lines in such an aspect as to conform to the ultrasound measurement conditions, making it possible to reduce the computation amount in the delay-and-sum and the data amount of the generated acoustic line signal in accordance with the ultrasound measurement conditions while suppressing degradation in the spatial resolution and the S/N ratio.

In another aspect, it is allowable to have a configuration in any of the above-described aspects, in which the combiner calculates a difference between the acoustic line signal frame data combined in synchronization with each of the transmission events and outputs an acoustic line signal corresponding to the difference in synchronization with each of the transmission events.

The acoustic line signal ds corresponding to the difference between transmission events is a sequence of the acoustic line signals ds extended in the depth direction corresponding to the width of one transducer 101a, being the data amount obtained by dividing the data amount of the acoustic line signal frame data ds_f by the number of transmission events.

With this configuration, the data to be transferred from the integrated circuit 501_3 for each of the transmission events can be reduced to the acoustic line signal ds corresponding to the difference between the transmission events out of the acoustic line signal frame data ds_f, making it possible to downscale the data transmission capability needed for data transmission to the succeeding stage of the integrated circuit 501_3.

An ultrasound signal processing method according to the present embodiment is an ultrasound signal processing method of transmitting an ultrasound beam to a subject using an ultrasound probe including a plurality of transducers and generating acoustic line signal subframe data on the basis of a reflected wave obtained from the subject, the ultrasound signal processing method including: a transmitting step of setting a focal point defining a converging point of an ultrasound beam in a subject and causing a plurality of transmission transducer arrays selected from the plurality of transducers to transmit the ultrasound beam to converge at the converging point; a receiving step of generating the reception signal sequence for each of the transducers of the ultrasound probe on the basis of the reflected wave received by the ultrasound probe from the subject; and a delay-and-sum step of performing delay-and-sum operation on the reception signal sequence based on the reflected wave obtained within an ultrasound beam main irradiation region to generate acoustic line signal subframe data for a plurality of on-line observation points present in a target line group passing through the focal point among a plurality of intra-region observation points corresponding to the position within the ultrasound beam main irradiation region, in which the receiving step includes a plurality of part receiving substeps of generating the reception signal sequence on the basis of the reflected wave received by each of the transducers included in a partial transducer array from the subject for each of a plurality of the partial transducer arrays obtained by dividing the transmission transducer array, the delay-and-sum step includes: a plurality of part delay-and-sum substeps of performing delay-and-sum on a reception signal sequence corresponding to the plurality of partial transducer arrays to generate an acoustic line signal for the plurality of on-line observation points so as to generate acoustic line signal partial subframe data corresponding to each of the plurality of partial transducer arrays; a plurality of part folding substeps of extracting an acoustic line signal sequence corresponding to the plurality of on-line observation points from the acoustic line signal partial subframe data corresponding to each of the plurality of partial transducer arrays, and arranging the acoustic line signals with reduced intervals between the target lines included in the target line group to generate acoustic line signal partial subframe folded data; a main summing substep of summing the acoustic line signal partial subframe folded data corresponding to each of the plurality of partial transducer arrays on the basis of the positions of the arranged observation points to generate acoustic line signal subframe folded data; and a re-sequence substep of re-sequencing the acoustic line signals in the acoustic line signal subframe folded data to the positions of the on-line observation points in the main irradiation region to generate the acoustic line signal subframe data.

In another aspect, it is allowable to have a configuration in any of the above-described aspects, in which each of the target lines included in the target line group is a straight line, and a distance between one observation point on one target line having a distance from the focal point being a predetermined distance or more and a closest observation point on the one target line is shorter than a distance between the one observation point and a closest observation point present on a target line adjacent to the one target line.

With such a configuration, it is possible to provide an ultrasound signal processing method capable of downscaling necessary internal memory capacity and data transmission capability of a receive beamformer of an ultrasound diagnostic apparatus, and an ultrasound diagnostic apparatus using this method.

With such a configuration, it is possible to reduce the computation amount of the delay-and-sum and the data amount of the acoustic line signal to be generated while suppressing degradation in the spatial resolution and the S/N ratio.

In another aspect, it is allowable to have a configuration in any of the above-described aspects, further including a combining step of combining a plurality of pieces of the acoustic line signal subframe data to generate acoustic line signal frame data, in which the transmitting step performs a transmission event of transmitting the ultrasound beam a plurality of times while changing the focal point, the receiving step generates the reception signal sequence in synchronization with each of the transmission events, the delay-and-sum step generates a plurality of pieces of the acoustic line signal subframe data in synchronization with each of the transmission events, and the combining step combines the plurality of pieces of acoustic line signal subframe data generated in synchronization with each of the transmission events to generate a plurality of pieces of acoustic line signal frame data on the basis of a position of the observation point.

With this configuration, it is possible to suppress degradation in the spatial resolution and the S/N ratio by using the synthetic aperture method.

<<Addendum>>

Each of the above-described embodiments illustrates a preferable specific example of the present invention. Numerical values, shapes, materials, constituents elements, arrangement positions and connection modes of constituents, steps and order of steps, or the like, illustrated in the embodiments are illustrative and are not intended to limit the present invention. Moreover, among the constituents in the embodiments, steps not described in the independent claims illustrating the top level concept of the present invention are described as optional constituents enabling a more preferable form.

Moreover, the execution order of the above-described steps is given as an example to specifically illustrate the present invention, and the order may be another order other than the example described above. Moreover, a part of the above steps may be executed simultaneously (in parallel) with the other steps.

Note that the scales of the constituents in each of the figures described in the above embodiments are different from the actual scale in some cases to facilitate understanding of the invention. Moreover, the present invention is not limited by the description of each of the above-described embodiments, and can be appropriately modified without departing from the scope and spirits of the present invention.

The ultrasound signal processing method and ultrasound diagnostic apparatus according to the present disclosure are useful in enhancement of performance of a conventional ultrasound diagnostic apparatus, in particular, enhancement of the framerate by reduced cost of a computing apparatus and reduced computational load, and downscaling of memory capacity and data transmission capability. Moreover, the present disclosure can also be applied to other devices such as a sensor using a plurality of array elements, in addition to ultrasound applications.

Although embodiments of the present invention have been described and illustrated in detail, the disclosed embodiments are made for purposes of illustration and example only and not limitation. The scope of the present invention should be interpreted by terms of the appended claims.

What is claimed is:

1. An ultrasound diagnostic apparatus that transmits an ultrasound beam to a subject using an ultrasound probe including a plurality of transducers and generates acoustic line signal subframe data on the basis of a reflected wave obtained from the subject, the ultrasound diagnostic apparatus comprising:
a transmitter that sets a focal point defining a converging point of an ultrasound beam in the subject and causes a plurality of transmission transducer arrays selected from the plurality of transducers to transmit the ultrasound beam to converge at the converging point;
a receiver that generates a reception signal sequence for each of the transducers of the ultrasound probe on the basis of the reflected wave received by the ultrasound probe from the subject; and
a delay-and-sum part that performs delay-and-sum operation on the reception signal sequence based on the reflected wave obtained within an ultrasound beam main irradiation region to generate acoustic line signal subframe data for a plurality of on-line observation points present in a target line group passing through the focal point among a plurality of intra-region observation points corresponding to the position within the ultrasound beam main irradiation region, wherein the receiver includes a plurality of part receivers that generates the reception signal sequence on the basis of the reflected wave received by each of the transducers included in a partial transducer array from the subject for each of a plurality of the partial transducer arrays obtained by dividing the transmission transducer array, the delay-and-sum part includes:
a plurality of part delay-and-sum parts that performs delay-and-sum on the reception signal sequence corresponding to the plurality of partial transducer arrays to generate an acoustic line signal for the plurality of on-line observation points so as to generate acoustic line signal partial subframe data corresponding to each of the plurality of partial transducer arrays;
a plurality of part folding parts that extracts an acoustic line signal sequence corresponding to the plurality of on-line observation points from the acoustic line signal partial subframe data corresponding to each of the plurality of partial transducer arrays, and that arranges the acoustic line signals with reduced intervals between the target lines included in the target line group to generate acoustic line signal partial subframe folded data;
a main summing part that sums the acoustic line signal partial subframe folded data corresponding to each of the plurality of partial transducer arrays on the basis of the positions of the arranged observation points to generate acoustic line signal subframe folded data; and
a re-sequence part that re-sequences the acoustic line signals in the acoustic line signal subframe folded data to the positions of the on-line observation points in the main irradiation region to generate the acoustic line signal subframe data.

2. The ultrasound diagnostic apparatus according to claim 1,
wherein each of the target lines included in the target line group is a straight line, and a distance between one observation point on one target line having a distance from the focal point being a predetermined distance or more and the closest observation point on the one target line is shorter than a distance between the one observation point and a closest observation point present on a target line adjacent to the one target line.

3. The ultrasound diagnostic apparatus according to claim 1, further comprising
a combiner that combines a plurality of pieces of the acoustic line signal subframe data to generate acoustic line signal frame data,
wherein the transmitter performs a transmission event of transmitting the ultrasound beam a plurality of times while changing the focal point,
the receiver generates the reception signal sequence in synchronization with each of the transmission events,
the delay-and-sum part generates a plurality of pieces of the acoustic line signal subframe data in synchronization with each of the transmission events, and
the combiner combines the plurality of pieces of acoustic line signal subframe data generated in synchronization with each of the transmission events to generate a plurality of pieces of acoustic line signal frame data on the basis of a position of the observation point.

4. The ultrasound diagnostic apparatus according to claim 1,
wherein the partial transducer array is obtained by dividing the transmission transducer array into n (n is a natural number larger than one),
n first integrated circuits and second integrated circuits are provided,
each of the plurality of part receivers, each of the plurality of part delay-and-sum parts, and each of the plurality of part folding parts are included in each of the n first integrated circuits,
the main summing part and the re-sequence part are included in the second integrated circuit, and
the acoustic line signal partial subframe folded data is transmitted from each of the n integrated circuits to the second integrated circuit.

5. The ultrasound diagnostic apparatus according to claim 1,
wherein the partial transducer array is obtained by dividing the transmission transducer array into n (n is a natural number larger than 1),
n integrated circuits are provided,
each of the plurality of part receivers, each of the plurality of part delay-and-sum parts, and each of the plurality of part folding parts are included in each of the n integrated circuits,
the main summing part and the re-sequence part are included in any of the n integrated circuits, and
the acoustic line signal partial subframe folded data is transmitted to the integrated circuit including the main sunning part and the re-sequence part from each of the other integrated circuits.

6. The ultrasound diagnostic apparatus according to claim 1, further comprising
a sequence determination part that determines sequence information to define a sequence method of the acoustic line signals on the target line in the acoustic line signal partial subframe folded data on the basis of various types of ultrasound measurement conditions,
wherein the part folding part sequences the acoustic line signal sequences for each of the target lines to generate the acoustic line signal partial subframe folded data on the basis of the sequence information.

7. The ultrasound diagnostic apparatus according to claim 4,
wherein the combiner calculates a difference between the acoustic line signal frame data combined in synchronization with each of the transmission events and outputs an acoustic line signal corresponding to the difference in synchronization with each of the transmission events.

8. An ultrasound signal processing method of transmitting an ultrasound beam to a subject using an ultrasound probe including a plurality of transducers and generating acoustic line signal subframe data on the basis of a reflected wave obtained from the subject, the ultrasound signal processing method comprising:
setting a focal point defining a converging point of an ultrasound beam in a subject and causing a plurality of transmission transducer arrays selected from the plurality of transducers to transmit the ultrasound beam to converge at the converging point;
generating the reception signal sequence for each of the transducers of the ultrasound probe on the basis of the reflected wave received by the ultrasound probe from the subject; and
performing delay-and-sum operation on the reception signal sequence based on the reflected wave obtained within an ultrasound beam main irradiation region to generate acoustic line signal subframe data for a plurality of on-line observation points present in a target line group passing through the focal point among a plurality of intra-region observation points corresponding to the position within the ultrasound beam main irradiation region, wherein the setting includes generating the reception signal sequence on the basis of the reflected wave received by each of the transducers included in a partial transducer array from the subject for each of a plurality of the partial transducer arrays obtained by dividing the transmission transducer array, the performing includes:

performing delay-and-sum on a reception signal sequence corresponding to the plurality of partial transducer arrays to generate an acoustic line signal for the plurality of on-line observation points so as to generate acoustic line signal partial subframe data corresponding to each of the plurality of partial transducer arrays;

extracting an acoustic line signal sequence corresponding to the plurality of on-line observation points from the acoustic line signal partial subframe data corresponding to each of the plurality of partial transducer arrays, and arranging the acoustic line signals with reduced intervals between the target lines included in the target line group to generate acoustic line signal partial subframe folded data;

summing the acoustic line signal partial subframe folded data corresponding to each of the plurality of partial transducer arrays on the basis of the positions of the arranged observation points to generate acoustic line signal subframe folded data; and re-sequencing the acoustic line signals in the acoustic line signal subframe folded data to the positions of the on-line observation points in the main irradiation region to generate the acoustic line signal subframe data.

9. The ultrasound signal processing method according to claim 8, wherein each of the target lines included in the target line group is a straight line, and a distance between one observation point on one target line having a distance from the focal point being a predetermined distance or more and the closest observation point on the one target line is shorter than a distance between the one observation point and a closest observation point present on a target line adjacent to the one target line.

10. The ultrasound signal processing method according to claim 8, further comprising combining a plurality of pieces of the acoustic line signal subframe data to generate acoustic line signal frame data, wherein the setting performs a transmission event of transmitting the ultrasound beam a plurality of times while changing the focal point, the generating generates the reception signal sequence in synchronization with each of the transmission events, the performing generates a plurality of pieces of the acoustic line signal subframe data in synchronization with each of the transmission events, and the combining combines the plurality of pieces of acoustic line signal subframe data generated in synchronization with each of the transmission events to generate a plurality of pieces of acoustic line signal frame data on the basis of a position of the observation point.

* * * * *